(12) United States Patent
Galgalikar

(10) Patent No.: US 11,058,314 B1
(45) Date of Patent: Jul. 13, 2021

(54) REMOTE INDIVIDUAL MONITORING, TRAINING AND RECORDING SYSTEM

(71) Applicant: Mahesh M. Galgalikar, San Jose, CA (US)

(72) Inventor: Mahesh M. Galgalikar, San Jose, CA (US)

( * ) Notice: Subject to any disclaimer, the term of this patent is extended or adjusted under 35 U.S.C. 154(b) by 123 days.

(21) Appl. No.: 15/720,704

(22) Filed: Sep. 29, 2017

Related U.S. Application Data

(63) Continuation-in-part of application No. 15/207,503, filed on Jul. 12, 2016.

(60) Provisional application No. 62/401,460, filed on Sep. 29, 2016, provisional application No. 62/401,465, filed on Sep. 29, 2016, provisional application No.
(Continued)

(51) Int. Cl.
| | | |
|---|---|---|
| *A61B 5/04* | (2006.01) | |
| *A61B 5/0408* | (2006.01) | |
| *A63B 24/00* | (2006.01) | |
| *A61B 5/00* | (2006.01) | |
| *A61B 5/0205* | (2006.01) | |
| *A61B 5/145* | (2006.01) | |

(Continued)

(52) U.S. Cl.
CPC .......... *A61B 5/04085* (2013.01); *A41D 1/002* (2013.01); *A61B 5/02055* (2013.01); *A61B 5/04012* (2013.01); *A61B 5/14542* (2013.01); *A61B 5/6804* (2013.01); *A63B 24/0062* (2013.01); *A61B 5/02416* (2013.01); *A61B 2503/10* (2013.01); *A61B 2562/0219* (2013.01); *A61B 2562/04* (2013.01); *A63B 2220/12* (2013.01); *A63B 2220/803* (2013.01); *A63B 2220/836* (2013.01); *A63B 2225/50* (2013.01); *A63B 2230/04* (2013.01); *A63B 2230/06* (2013.01); *A63B 2230/30* (2013.01); *A63B 2230/42* (2013.01); *A63B 2230/50* (2013.01)

(58) Field of Classification Search
CPC ............ A61B 5/04085; A61B 5/02055; A61B 5/04012; A61B 5/6804; A61B 5/02416; A61B 5/14542; A61B 2503/10; A61B 2562/0219; A61B 2562/04; A41D 1/002; A63B 24/0062; A63B 2220/12; A63B 2220/803; A63B 2220/836; A63B 2225/50; A63B 2230/04; A63B 2230/06; A63B 2230/30; A63B 2230/42; A63B 2230/50

See application file for complete search history.

(56) References Cited

U.S. PATENT DOCUMENTS

| 4,622,979 A | 11/1986 | Katehis et al. |
| 5,730,143 A | 3/1998 | Schwarzberg |

(Continued)

*Primary Examiner* — Catherine M Voorhees
*Assistant Examiner* — Roland Dinga

(57) ABSTRACT

The invention provides a wearable multi-modal body sensor and network for continuous health monitoring, selective recording, and transmission of various body vitals such as BPM, ECG, EEG, temperature, blood pressure, $O_2$ saturation, body balance, etc. The selective recording can be timed and centered on the occurrence of clinically significant events detected by the monitoring system, A continuous log of all body vitals can also be stored in the system according to various scenarios. In certain embodiments, the system includes a patch wearable by the individual and including a number of sensors, A sensor module is releasably secured to the patch in connection with the sensors in order to receive the signals obtained by the sensors for ECG and EEG analysis, for example.

2 Claims, 41 Drawing Sheets

Related U.S. Application Data

62/407,621, filed on Oct. 13, 2016, provisional application No. 62/412,642, filed on Oct. 25, 2016, provisional application No. 62/464,794, filed on Feb. 28, 2017.

(51) Int. Cl.
*A41D 1/00* (2018.01)
*A61B 5/024* (2006.01)

(56) References Cited

U.S. PATENT DOCUMENTS

| | | | |
|---|---|---|---|
| 6,225,901 B1 | 5/2001 | Kail, IV | |
| 6,665,385 B2 | 12/2003 | Rogers et al. | |
| 6,694,177 B2 | 2/2004 | Eggers et al. | |
| 7,222,054 B2 | 5/2007 | Geva et al. | |
| 7,651,638 B2 | 1/2010 | Segall et al. | |
| 7,713,447 B2 | 5/2010 | Segall et al. | |
| 7,867,511 B2 | 1/2011 | Segall et al. | |
| 7,998,574 B2 | 8/2011 | Segall et al. | |
| 8,673,184 B2 | 3/2014 | Burnham et al. | |
| 8,788,009 B2 | 7/2014 | Greene et al. | |
| 8,792,957 B2 | 7/2014 | Greene et al. | |
| 9,597,004 B2 | 3/2017 | Hughes et al. | |
| 2006/0282021 A1* | 12/2006 | DeVaul | A61B 5/0024 600/595 |
| 2010/0063365 A1 | 3/2010 | Pisani et al. | |
| 2010/0081913 A1* | 4/2010 | Cross | A61B 5/04085 600/386 |
| 2010/0249625 A1 | 9/2010 | Lin | |
| 2011/0009711 A1* | 1/2011 | Nanikashvili | A61B 5/0002 600/301 |
| 2014/0058680 A1 | 2/2014 | Geva et al. | |
| 2016/0007916 A1* | 1/2016 | Iwawaki | A61B 5/02055 600/301 |

* cited by examiner

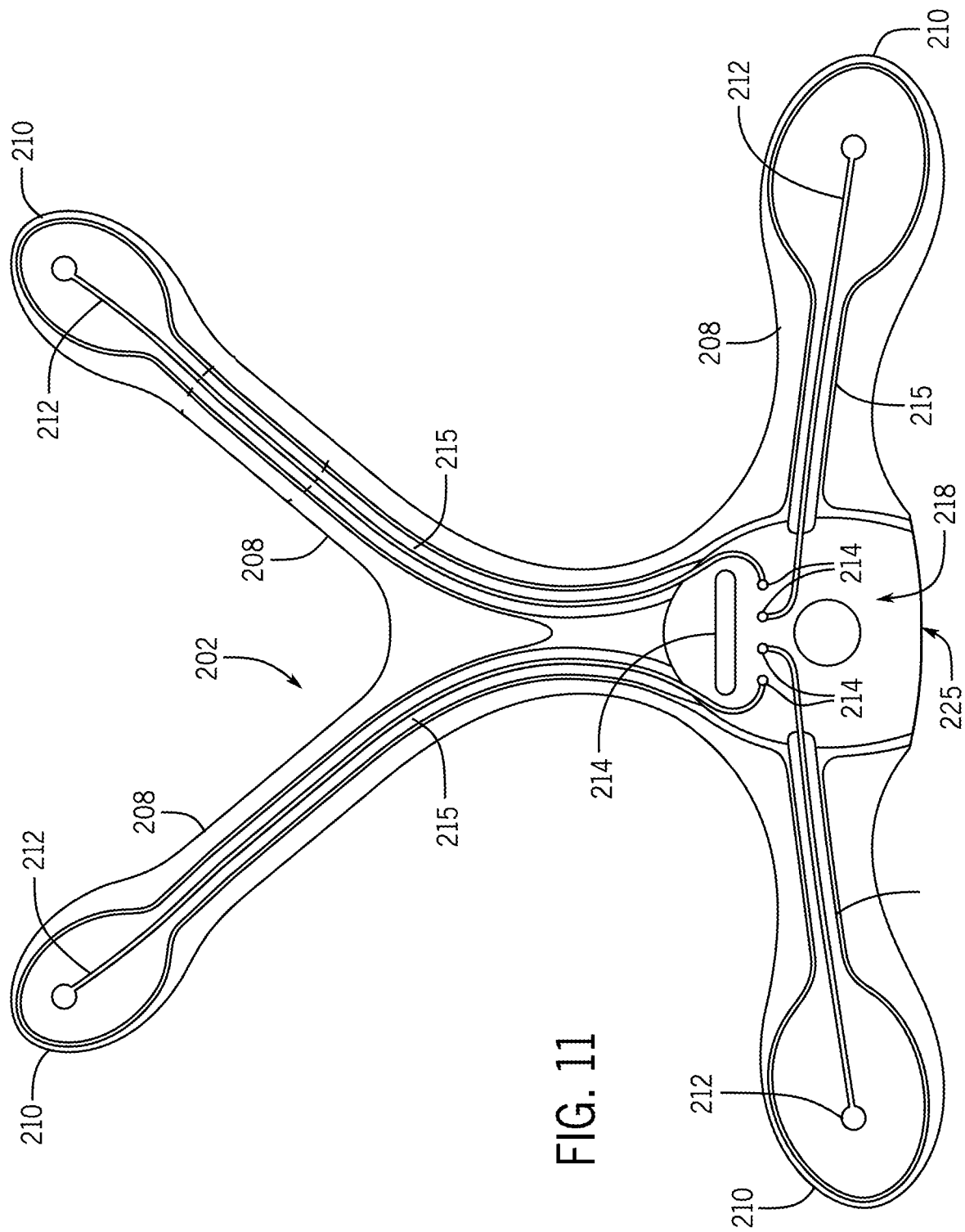

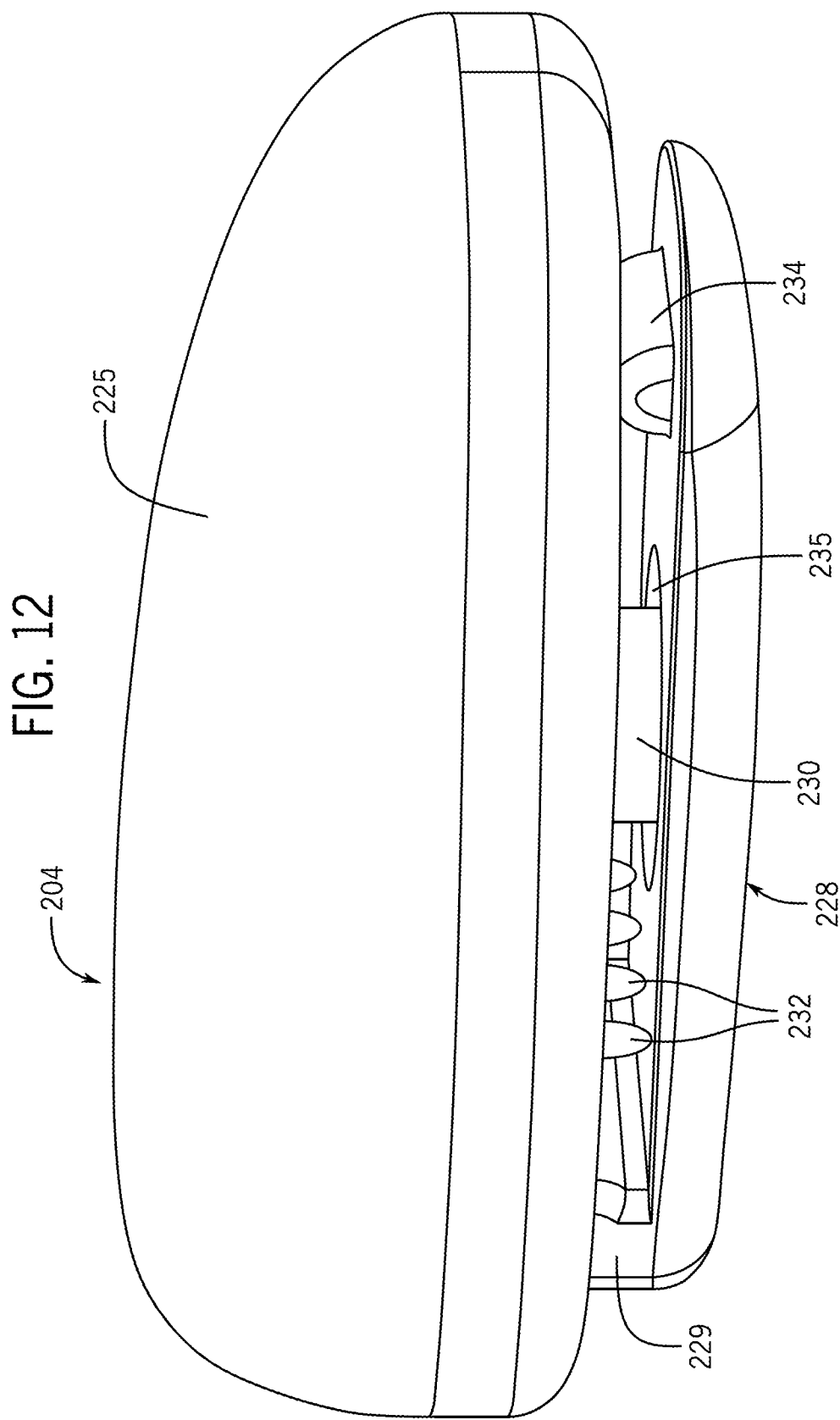

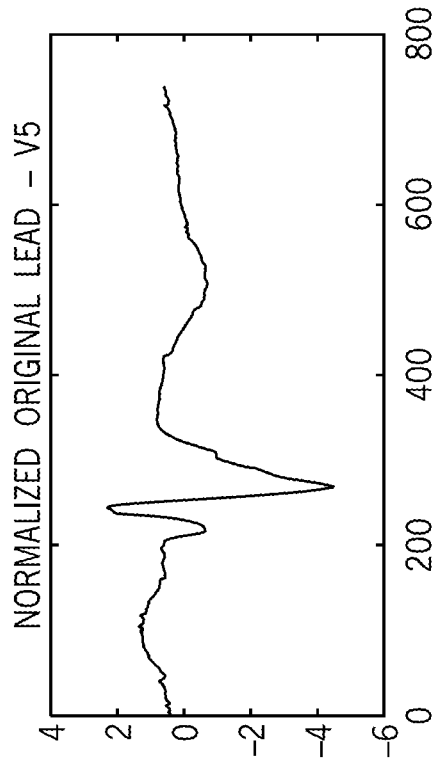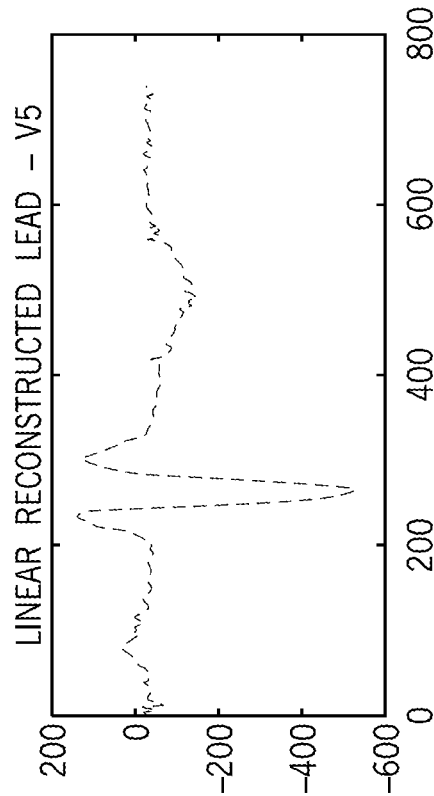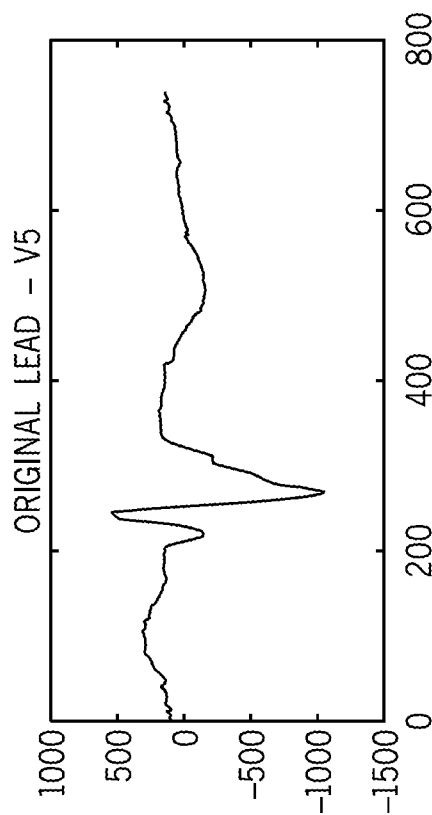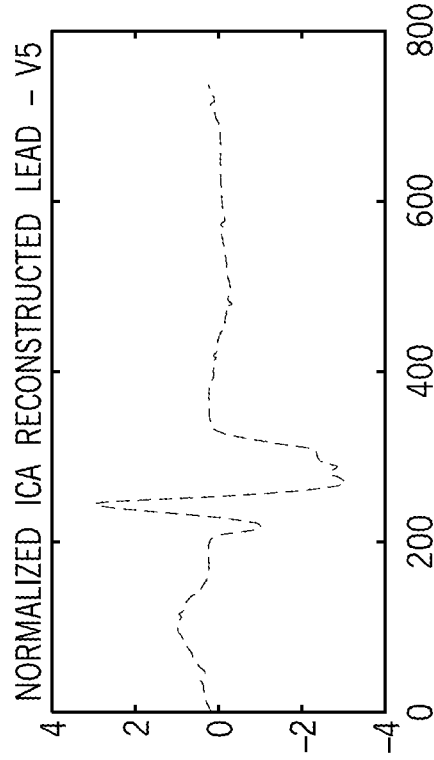

REMOTE INDIVIDUAL MONITORING, TRAINING AND RECORDING SYSTEM

CROSS-REFERENCE TO RELATED APPLICATIONS

The present application claims priority as a continuation-in-part of U.S. Non-Provisional application Ser. No. 15/207,503, filed on Jul. 12, 2016, as well as from U.S. Provisional Patent Application Ser. No. 62/401,460, filed Sep. 29, 2016, U.S. Provisional Patent Application Ser. No. 62/401,465, filed Sep. 29, 2016, U.S. Provisional Patent Application Ser. No. 62/407,621, filed Oct. 13, 2016, U.S. Provisional Patent Application Ser. No. 62/412,642, filed Oct. 25, 2016, and U.S. Provisional Patent Application Ser. No. 62/464,794, filed Feb. 28, 2017, the entirety of which are each expressly incorporated by reference herein for all purposes.

FIELD OF THE INVENTION

This disclosure relates to the field of medical device multi-modal health monitoring. And more specifically to continuous monitoring of specific body functions and potential defects.

BACKGROUND OF THE INVENTION

Biological signals from the body like heart rate, electro-cardiograms, body temperature, pulse and other body data give medical professionals and athletes invaluable data about their bodies. By interpreting this data, much valuable information can be gleaned about an individual's health, and even instruct corrective behavior when needed. Devices already exist on the market to get this data, but they are usually complicated, leading to installation errors, and thus possibly giving false data. There is a need to develop an "idiot-proof" solution that easily attaches to the body and gives good data without requiring overly complicated installation skills. Most Electrocardiogram devices require large and expensive computers to read data and log data from the sensors, however such equipment is expensive and cumbersome for personal use. Furthermore these expensive devices are usually housed in medical facilities. However medical facilities are becoming increasingly expensive and crowded. Data monitoring of an individual's vital signs should not have to require someone incurring this expense or crowding of a medical facility. There is then a need to develop a portable and affordable body monitoring device that can freely broadcast vital sign information to a data cloud service, allowing powerful server-based computations and broadcast of that information to desired mobile or stationary devices allowing maximum freedom and mobility.

For many years, wearable medical devices have focused on monitoring and recording electro-cardiogram (ECG) information. Cardiac patients have been evaluated with a device known as a "Holter" monitor. The patient wears a series of small sensors which pick up various signals from the heart. These signals are recorded on a paper tape which is sent to a central station for evaluation. A computer may be used to search for irregularities which might have occurred during recording of up to 24 hours or more. These devices have limitations in that a patient may not have been symptomatic during the monitoring period, thus the recorded arrhythmias may have little or no significance. Transmission time and subsequent analysis of the data may cause unacceptable delays in critical diagnosis. Overall, the Holter device has many limitations restricting its efficiency.

With advances in technology, medical event monitoring devices have been developed for specific cardiac monitoring. These devices worn by patients record ECG information when triggered by the patient or the occurrence of a significant event. The recording usually lasts for one to five minutes and can be transmitted by telephone. The advantage of such a device is the capability for extended monitoring as the device does not have to be continuously operational. A major disadvantage is the availability of limited data to physicians for analysis. They are accustomed to extended monitoring information at hospitals.

Another type of device illustrated in U.S. Pat. No. 4,622,979 (to Katehis et al.) defines an ECG monitoring device which continuously monitors and digitally stores information in memory. When memory becomes full new data overwrites the old data. Upon occurrence of an event the patient may halt the overwriting of data. Data may then be downloaded via smart phone to a central location for analysis. The device may be programmed to retain a defined time frame of data before and after activation. This device also has a major disadvantage in that it does not have the capability to provide extensive data and/or an extended monitoring period as do Holter type devices. Another major disadvantage is that the device relies on patients to trigger recording. A clinically significant event may occur without the patient being symptomatic (e.g. the patient feels no pain while an event is occurring). Thus no event is recorded.

In an attempt to resolve the above issues, another device U.S. Pat. No. 5,730,143 (to Schwarzberg et al,) was introduced. It was an EGG monitor (Holter type device) and recording device including long-term recording and selective event recording. The selective recording permits real-time evaluation of the incoming data for evaluation of a clinically significant event. The parameters of what constitutes a clinically significant event are adjustable. The device may be remotely programmed in accordance with a physicians orders, based on the patient's medical history. Upon meeting the required parameters the data is stored in an evaluation buffer and the patient is alerted. The patient can manually transfer data to a holding buffer. Data can also be transmitted to a doctor or a central monitoring station. The device also includes long-term data recording like a "Holter" monitor. However, one of the major disadvantages of all of the above inventions is that all of the devices are monitoring and transmitting only EGG data, whereas other vitals such as $O_2$ saturation, blood pressure, and heartbeats/minute (BPM) are not addressed. These and other parameters are all important for proper diagnostic measures. Another disadvantage is that these devices are good for only arrhythmia detection wherein the patient may suffer from other clinically significant events triggered by congenital defects. Even if a patient stops breathing, the device won't detect the event as it monitors only the electrical activity of the heart.

Advancements in the field of telemedicine have brought a revolution in health care monitors. Multiple embedded sensors now monitor various vitals. A device illustrated in U.S. Pat. No. 7,222,054 (to Geva et al.) is directed to personal ambulatory wireless health monitoring for mobile patients. The device contacts a central station to record the patient's physiological data and the patient's location. It can also provide two-way voice communication between the patient and the central station. This device monitors ECG, 02 saturation, blood glucose, body temperature, blood pressure and includes an air flow sensor which measures spirometry. Monitoring may be initiated by the patient with or without a periodic reminder or it may be initiated by programming the device. However, these devices have been found to be less than satisfactory as the patient may not have been symptomatic during the monitoring period. Thus, the recorded data may have no significant value. It also lacks subsequent relative analysis of the data for any clinically significant event monitoring and recording. And slow transmission of data may cause unacceptable delays. Another major disadvantage is that it does not provide acoustic analysis of the heart, which could be very helpful for detecting any congenital heart defect, any stenosis or physical injury to the heart resulting from an accident.

In addition, many types of individual monitoring devices are currently available to provide the individual with information about the health of the individual. The devices can monitor the activity of the individual, such as the steps taken by the individual, in order to provide certain correlating information on the health of the individual.

Many of these devices can additionally measure and pride information on the heart rate of the individual. To do so, the device includes sensors capable of monitoring the electric activity of the heart to produce an electrocardiogram (ECG) for the individual. This ECG can be analyzed by the device to provide the heart rate of the individual, as well as comparative information with regard to the acceptable ranges for the heart rate based on various parameters of the individual using the device, i.e., height, weight, age, etc.

Further, the data obtained by the device can be utilized to diagnose or determine whether the individual is undergoing a clinically relevant event, such as cardiac arrest, and can alert appropriate medical personnel.

However, in these devices the signals obtained by the device are mainly focused on ECG recording and analysis, with all of the analytics regarding the ECG signal being based off of this single signal or variable. Thus, with only the single variable being sensed and analyzed it is often the case where a device can provide a false diagnosis of the condition of the individual. For example, when sensing only the ECG signal, an elevated signal (tachycardia) can be diagnosed by the device as cardiac arrest, while it can simply be the result of a normal reaction of the individual to hyperactivity of body, such as during a strenuous workout.

In the prior art there are few devices or diagnostic patches which record multiple vital statistics of the individual on which the device is placed, but these devices either focus on same single variable (ECG) analytical system or are simply recording the data on the multiple sensed variables/vital parameters or statistics for later analysis. Further, no prior art devices record any acoustic data from the individual for analysis.

In one specific prior art device disclosed in U.S. Pat. No. 9,597,004, entitled Wearable Monitor, the entirety of which is expressly incorporated by reference herein for all purposes, the device can be utilized to obtain information on the heartbeat of an individual, but is otherwise limited in the types and analysis of the information obtained from the individual.

As a result, it is desirable to develop a medical monitoring device that is capable of recording and analyzing data on multiple parameters of the individual, including acoustic data, to provide better diagnostic results while helping to significantly reduce the possibility of a false diagnosis.

In addition, the invention presented herein is directed to overcome the shortcomings of the "Holter" type devices, event type cardiac monitors, and personal ambulatory wireless health monitors.

SUMMARY OF THE INVENTION

The invention is a body sensor system comprised of a sensor pad with multiple sensor regions, a conductive element that traverses the sensor pad and delivers all signals to at least one sensor area, a modular sensor hub, and a mechanical feature that helps secure the sensor hub attach to the sensor pad. This feature may include raised contours and a hole to help it lock into place.

In an exemplary embodiment, the sensor hub has a protrusion that passes through a hole of the sensor pad and rotates to a locking closed position, thereby securing it to the pad and also forcing a mechanical contact with electrically conductive elements on or in the sensor pad that carry signal data from the sensing regions of the pad and into the sensor hub. The sensor hub then broadcasts data wirelessly.

In an exemplary embodiment, the data obtained by the sensors/patches of the sensor system is sent to a wireless device like a IoT gateway or a smart phone which can give live feedback to the user and/or send data to a cloud-type data service. The sensor system can directly send the data, or can utilize a smart IoT bridge, that operates to effectively connect the hub to a network in order to enable the hub to transmit the data to a remote location from the sensor system. The smart IoT bridge can be formed integrally with or separately from the sensor system and is capable of communicating with our medical device over Bluetooth® protocols, such as a Bluetooth® Low Energy (BLE) protocol, and push the data received over Wi-Fi using an Internet of Things (IoT) network protocols, for example. In one embodiment, the smart IoT bridge includes BLE and Wi-Fi chips which communicate with each other of protocol stack level to establish communication between two different communication protocols, i.e., BLE and Wi-FI. Data from or to the sensor system is pushed over/through/into a cloud network here it is captured and processed by a suitable software system.

In another exemplary embodiment of the invention, the sensor system includes a hub having a microcontroller disposed therein that is operably connected to the sensors/patches and that includes a set of pre-programmed instructions utilized for the collection and transmission of the signals obtained from the sensors operably connected to the hub. The hub or a computing device located remotely from the hub can subsequently receive the sensor data, such as 3 lead ECG data, and can reconstruct a full 12 lead ECG signal set from the data received by the three (3) lead ECG sensors forming a part of the sensor system. In addition, to the ECG sensor signals the hub is capable of capturing PPG, Oxygen saturation, Surface skin temperature, 9-axis inertial sensor, the hub/microcontroller or other remote computing device can employ a noise reduction operation on the sensor signals in order to provide more accurate signals for review and analysis.

In accordance with an exemplary embodiment of the invention, an efficient and low cost multi-modal health monitoring system including real time analysis of various human body vitals is provided.

The proposed medical device system is a multi-modal monitoring and recording system that includes a body-attached device or network that includes or communicated with a unique and optionally disposable sensor/patch for continuous long-term recording with real time analysis of various body vitals. Data is recorded and stored in a buffer memory to capture evidence of a clinically significant event. Occurrence of such an event which meets pre-programmed parameters causes the data to be stored in memory and subsequently transmitted to a remote monitoring site triggering an immediate response alert. The patient, along with others, is made aware of the necessity for follow up. The monitor system includes long term memory, multiple sensors to gather body vitals and a sophisticated low power communications link for transmitting the data to a central monitoring site where data is analyzed for specific events.

Various embodiments of the disclosed subject matter provide a system to sense various body parameters, continually monitor, selectively record data, transmit various body vitals and provide analysis in real time of that data. The data is transmitted via a sophisticated low power communication link through the wireless cellular telephone network or a smart IoT bridge or other suitable transmission system. One embodiment of the enclosed subject provides a wearable acoustic patch device with the capability to identify twenty-one different heart abnormalities. This Acoustical Pattern Recognition (APR) system is based on a wearable sensor acquiring heart sounds and through complex signal processing detecting and differentiating various heart defects. An alternative embodiment of the disclosed subject matter provides a more comprehensive multi-modal sensor system capable of monitoring and recording data related to body vital functions such as, but not limited to, BPM (heart rate), ECG, blood pressure, $O_2$ saturation, and body balance and gait, body temperature.

In accordance with one exemplary embodiment of the present invention a multi-modal monitoring and recording apparatus includes a portable body-attached network/patch including at least one physiological data sensor node to gather patient physiological data. The patch also includes onboard GPS modality to capture the exact location of the patient or athlete in the field. The device may communicate via Bluetooth, Zigbee or any RF protocols or IoT protocols for communication with the central processing hub. The digital circuitry for processing signals associated with any physiological data from sensor nodes is thereby transmitted to the processing hub.

Further in accordance with another exemplary embodiment the system can utilize the ECG data obtained in order to derive multiple physiological parameters (up to 27 different physiological parameters) concerning the individual from whom the ECG data was obtained. This acoustic ECG data and derived parameter information enables diagnoses to be made much more accurately than in prior art single parameter monitoring devices. In addition, the acoustic ECG data can be utilized in conjunction with various algorithms and historical data stored on the individual in order to more accurately determine the present condition of the monitored individual.

In accordance with another exemplary embodiment of the invention, co-relative analysis of PPG and ECG data can be performed an analysis of blood pressure based on relative analysis of ECG and photoplethysmography. Including these determinations in a single system provides versatility in that co-relating different body vitals allows the system to determine the emotional and physical state of a person by forming a unique base line for every individual which can be very helpful in profiling a patient as each patient has their own normal state, e.g. a BP of 145/100 is normal for one person but may be representative of hypertension for another person. Further, in assessing physical performance, such as for the training of athletes, the co-relation of these parameters can be very effective in understanding a players physiology while he is "on the field" and performing in a game, or practice situation. Such player profiling can prevent lot of on field injuries in elite athletes. The system utilized for this and other purposes can also include GPS capability which will also help the coach to monitor the player and overall team activity on field and can improve the strategic planning for the team.

Further in accordance with another exemplary embodiment of the present invention at least one physiological data sensor node is assembled within the patch.

Still further in accordance with an exemplary embodiment of the present invention at least one physiological data sensor node is connected external to the patch.

Additionally, in accordance with another exemplary embodiment of the present invention the external portion of at least one physiological data sensor node is connected to the patch via a connector.

Further in accordance with an exemplary embodiment of the present invention the personal status monitor onboard the patch operates by polling the sensor nodes.

Further in accordance with another exemplary embodiment of the present invention at least one physiological data sensor node operates continuously.

Additionally, in accordance with an exemplary embodiment of the present invention the multimodal patch/system/module includes memory, either local or remotely accessible by the patch/system/module for storing any of the physiological data. Moreover, the multi-modal patch memory may include a standard reference database for comparison with the physiological data recorded by the sensor nodes.

Additionally, in accordance with another exemplary embodiment of the present invention the multimodal patch the system can contact a twenty-four hour emergency service, central hub, or a patient's relative when physiological data appears to be outside of normal parameters.

In accordance with another aspect of an exemplary embodiment of the invention, a body sensor system is designed that includes a patch or body-worn portion that includes a number of sensors disposed with the patch. A module is separably attached to the patch and is operably connectable to the sensors disposed in the patch. The module can obtain the information from the sensors in the patch and from additional sensors located directly within the module to ascertain different physiological signals regarding the health of the individual wearing the body sensor system. The information obtained via system can include ECG data and EEG data which can then be downloaded or otherwise transferred from the module for use by a physician or other individual in determining the physical state of the individual wearing the body sensor system.

These and other advantages of the disclosed subject matter, as well as additional novel features, will be apparent from the description provided herein. The intent of this summary is not to be a comprehensive description of the claimed subject matter, but rather to provide a short overview of some of the subject matter's functionality. Other system, methods, features and advantages here provided will become apparent to one with skill in the art upon examination of the following Figures and detailed description. It is intended that all such additional systems, methods, features and advantages be included within this description, and be within the scope of the accompanying claims.

BRIEF DESCRIPTION OF THE DRAWINGS

The drawings illustrate the best mode currently contemplated of practicing the present invention.

In the drawings:

FIG. 11 is an isometric view of a patch for the body sensor system according to another exemplary embodiment of the invention.

FIG. 12 is an isometric view of a sensor module for the body sensor system according to another exemplary embodiment of the invention.

FIGS. 33A-33D are graphs of the signals of original lead V5, normalized original lead V5, normalized ICA reconstructed lead V5 and linear reconstructed lead V5 obtained according to an exemplary embodiment of the invention.

DETAILED DESCRIPTION OF THE DRAWINGS

Figure 1:
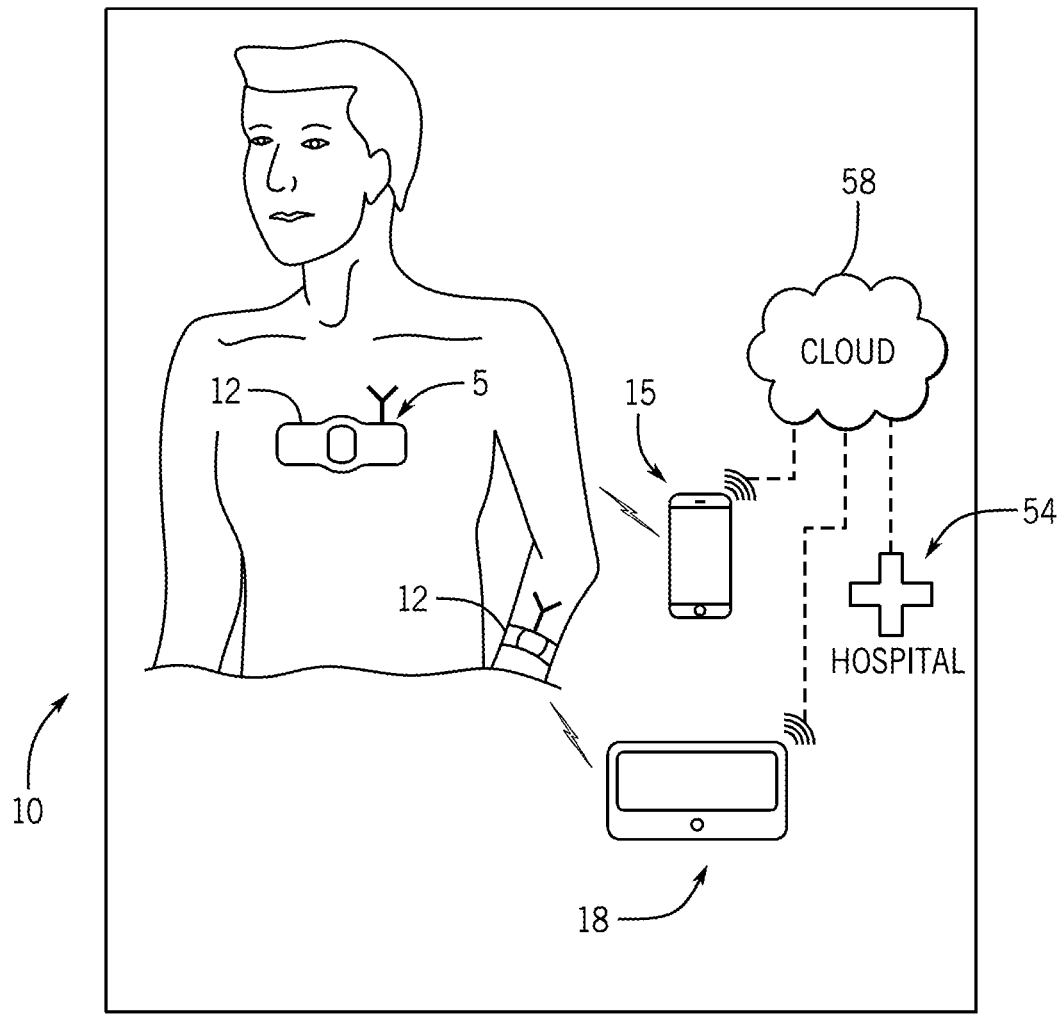
FIG. 1 is a schematic view of the monitoring system according to one exemplary embodiment of the invention.

The following description is not to be taken in a limiting sense, but is made for the purpose of describing the general principles of the present disclosure. The scope of the present disclosure should be determined with reference to the claims. Exemplary embodiments of the present disclosures are illustrated in the drawings, like numbers being used to refer to like and corresponding parts of the various drawings.

In operation, the disclosed subject matter provides examples of a multi-modal wireless medical device monitoring system comprised of a sensor system which collects vital signs and other data related to the human condition and transmits that data wirelessly to a central station for analysis.

With reference now to FIG. 1, one exemplary embodiment of a multi-modal monitoring and recording system for collecting clinical health data of a person is illustrated generally at 10. The system 10 can be applied to track individuals or multiple persons simultaneously, such as monitoring and/or profiling performance of a team of players during team training sessions and during actual game play. The system 10 includes a body sensor network 12, such as an acoustical patch, that is positioned on an individual 14 in any suitable manner, such as by an adhesive, a strap, or other suitable structure, that can be provided with a firmware that enables it to fetch the data from a number of sensor nodes 16 operably connected to the body sensor network 12. The body sensor network 12 is also configured to process and transmit the sensor data to a central hub 18 through the use of communication hardware within the body sensor network 12 such as processors and other network topologies. The central hub 18 can be formed as any personal computer, cloud server, personal data accessories, cellular phones, or combination thereof.

Figure 2:
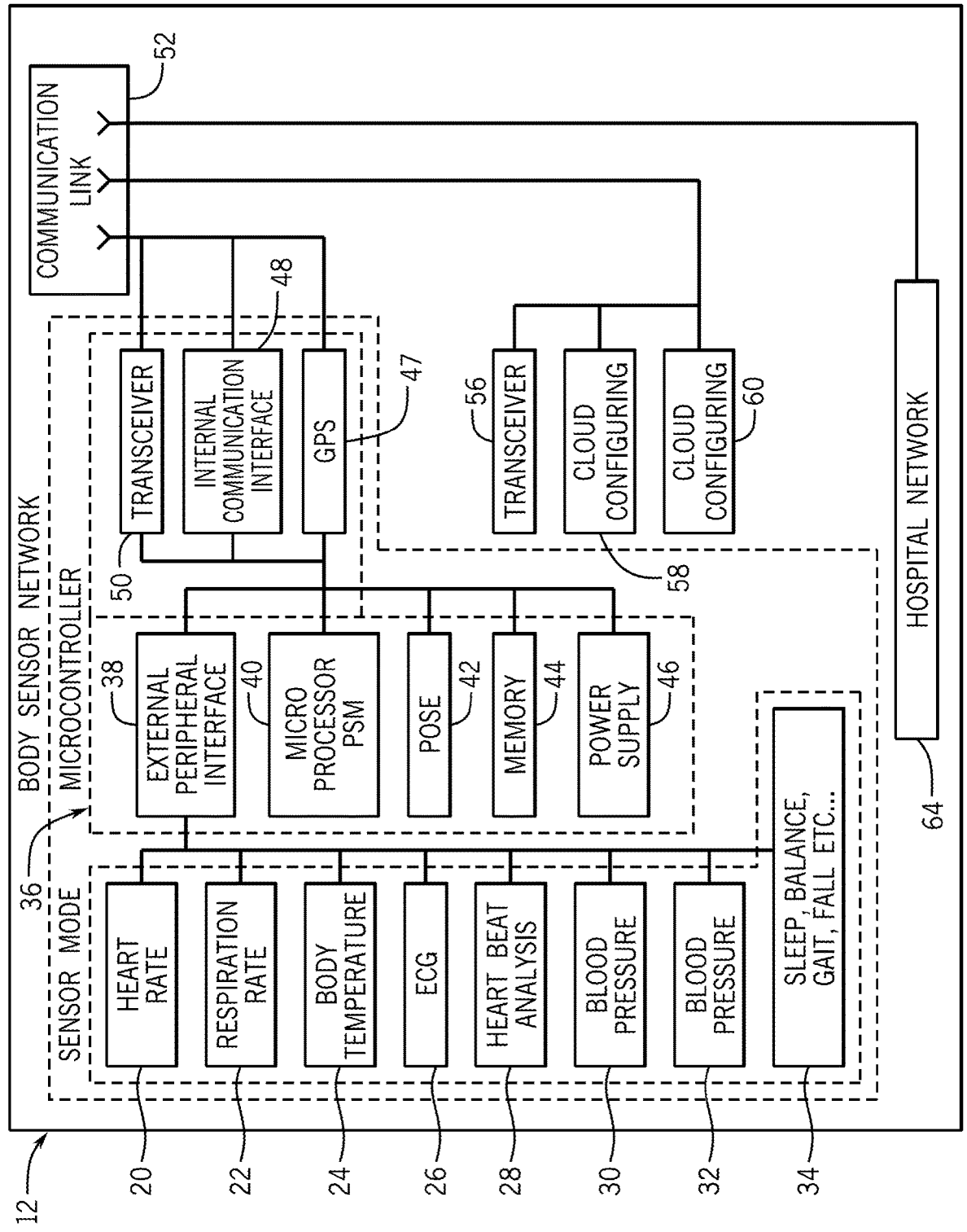
FIG. 2 is a schematic view of a body sensor network according to an exemplary embodiment of the invention.

Referring now to FIG. 2, in one exemplary embodiment, the body sensor network 12 includes sensors and/or dedicated modules or systems including sensors configured to sense one or more physiological signals of the individual, including but not limited to, heart rate 20, respiration 22, temperature 24, ECG 26, heart beat analysis 28, blood oxygen levels 30, blood pressure 32, and sleep, balance and/or gait 34 and any combinations thereof. The systems/sensors 20-34 can be disposed within a housing (not shown) for the body sensor network 12, or can be connected to the network 12 as exterior systems/components. Further, the systems/sensors 20-34 can be selected from one or more conductive fabric sensors, dry ECG sensors, traditional ECG electrodes, optical module sensors, 9-axis inertial sensors and combinations thereof, among any other suitable types of sensors for obtaining body parameter/physiological signal data from a patient or individual. The network 12 and/or the individual sensor modules 20-34 can include a microcontroller 36 having one or more of an external peripheral interface 38, a port 40, a microprocessor/personal status monitor 42, memory 44 and a power supply 46. The microprocessor 42 can be operably connected to one or more of a GPS 47, an internal communication interface 48 and a transceiver 50. One or more of these devices can operably connected the network 12 via a communication link 52 to a separate transceiver 56, a cloud computing system 58, a data analysis network 60 and/or a hospital network 64.

Figure 3:
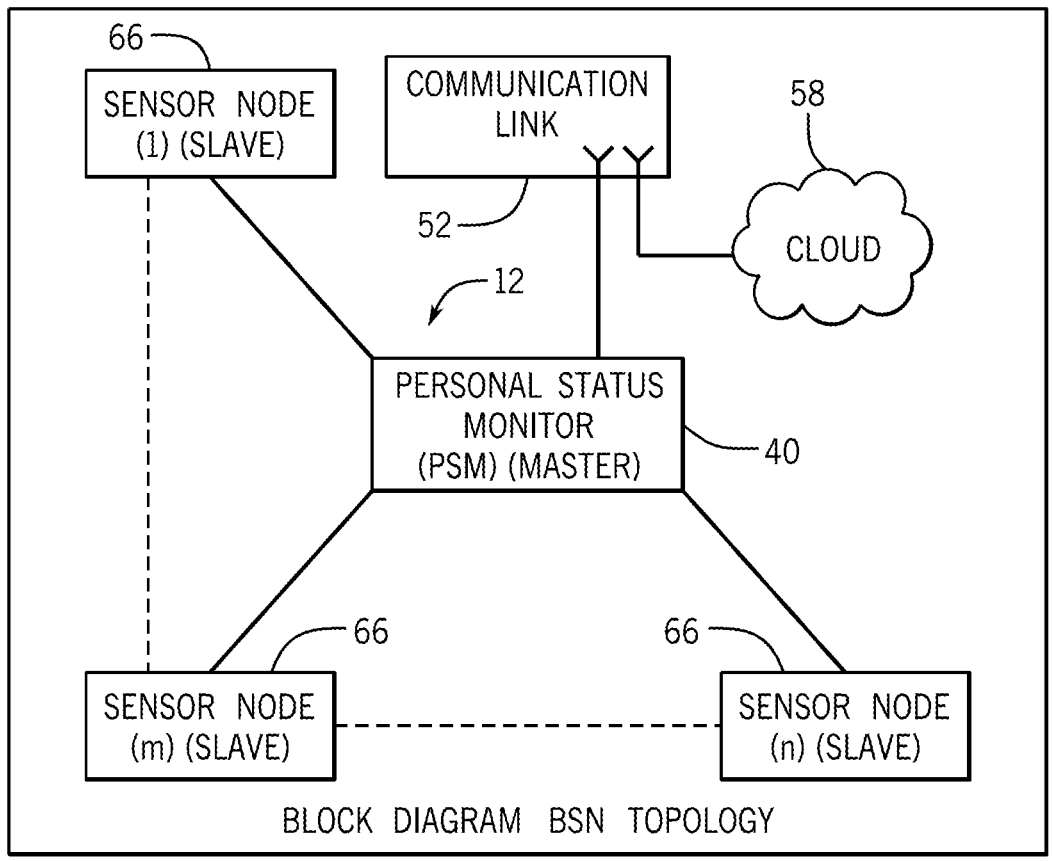
FIG. 3 is a schematic view of a body sensor network according to another exemplary embodiment of the invention.
Figure 4:
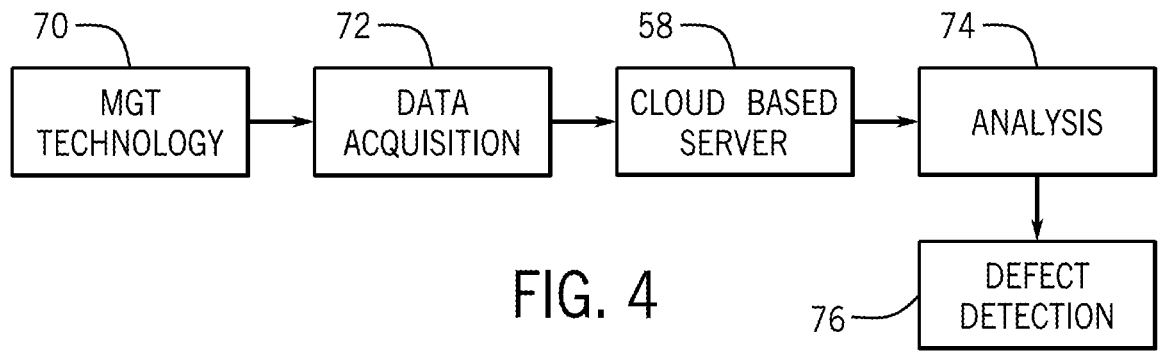
FIG. 4 is a schematic view of an operating process of the monitoring system according to an exemplary embodiment of the invention.

FIG. 3 illustrates another exemplary embodiment of a multi-modal sensor monitoring and recording system 10 in which the network 12 includes a personal status monitor 42 to which are connected a number of slave sensor nodes 66 that transmit signal data to the monitor 42 for transmission to another location, such as a cloud computing network/system 58.

Looking now at FIGS. 4-7, the various functions of the system 10 are illustrated according to one embodiment of the invention. The functions provided and/or performed by the system 10 include the initialization or individualization function 70 of the network 12 for a person, the data acquisition function 72 by the network 12, the transmission of the acquired data from the network 12 to a remote server or network, and the analysis function 74 of the data, including defect or condition detection 76 from the data.

Figure 5:
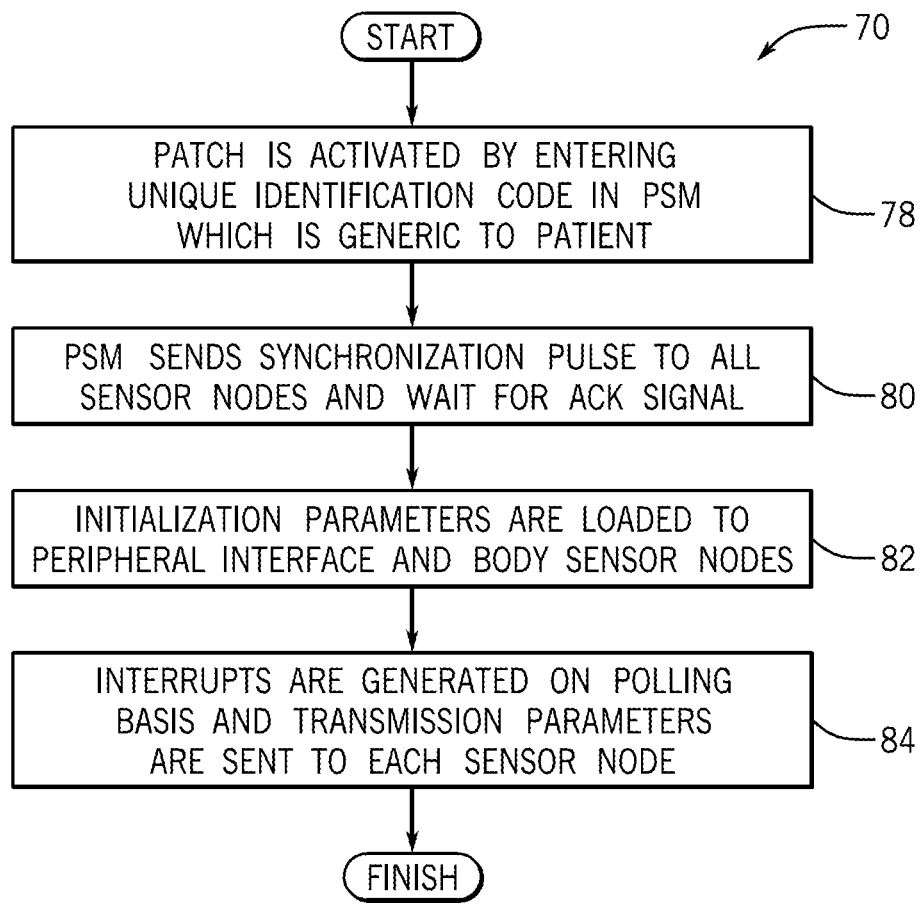
FIG. 5 is a flowchart illustrating an initiation function of the body sensor network according to an exemplary embodiment of the invention.

In the exemplary illustrated embodiment of FIG. 5, the initialization function 70 includes an initial step in block 78 of activating a code into the PSM 44 in the network/patch 12 that is unique to the individual. In block 80, the network/patch 12 then receives a synchronization pulse from the associated sensors/systems 20-34, and the initialization parameters are transmitted/loaded onto the nodes 20-34 and to the peripheral interface 38 in block 82. In block 84, data transmission parameters are sent to the sensors/systems 20-34 and the network/patch 12 is ready to obtain data on the individual.

Figure 6:
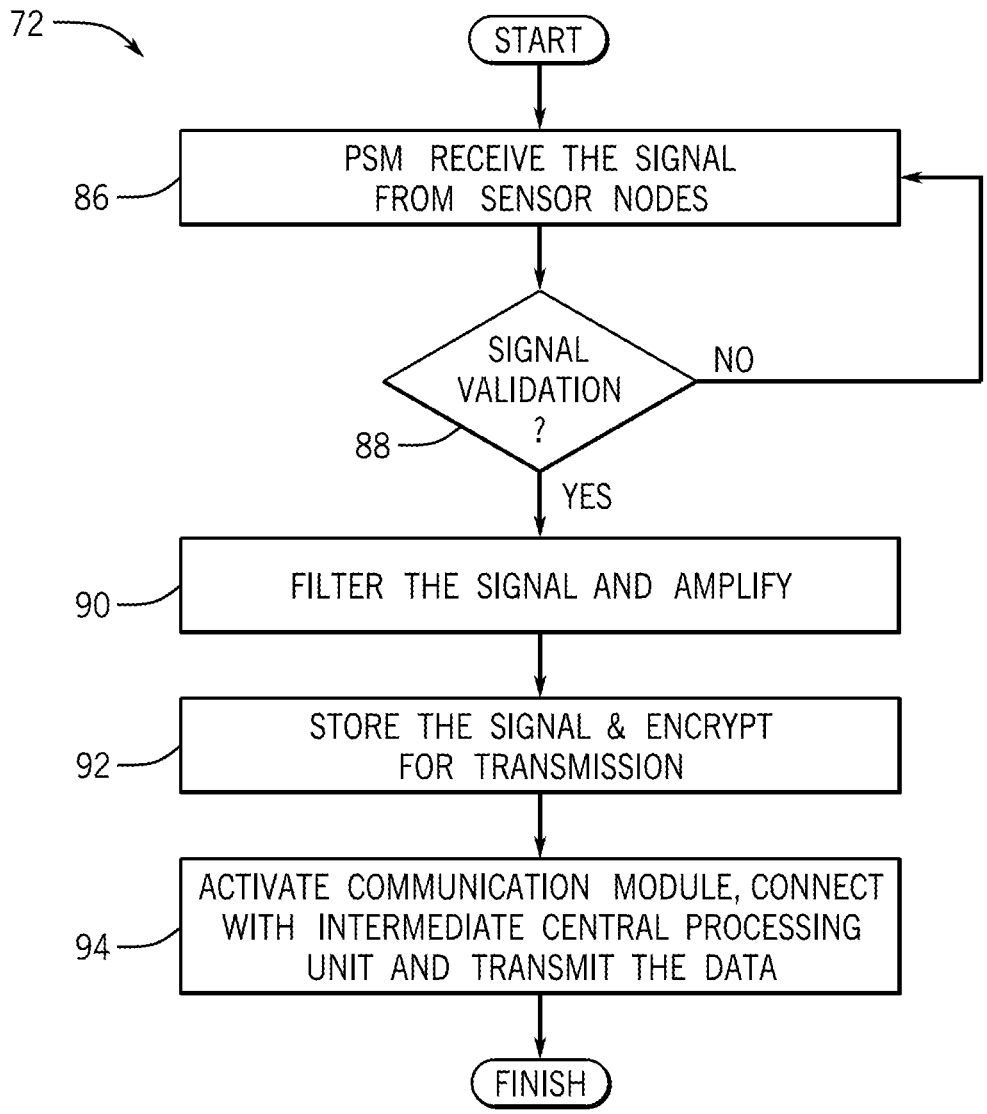
FIG. 6 is a flowchart illustrating a signal obtaining and transmission function of the body sensor network according to an exemplary embodiment of the invention.

Looking now at the exemplary illustrated embodiment of the data acquisition function 72 in FIG. 6, in block 86 initially the PSM 44 receives signals from the nodes 20-34. If these signals do not include the code provided in the initialization function 70 and cannot be validated in block 88, the signals are disregarded. However, if the signals are validated with the appropriate code, in block 90 the signal is filtered for clarity and amplified. In block 92, the filtered and amplified signals are encrypted and stored, with the encrypted signals transmitted via the communication module associated with the network/patch in block 94 to a remote server or network.

Figure 7:
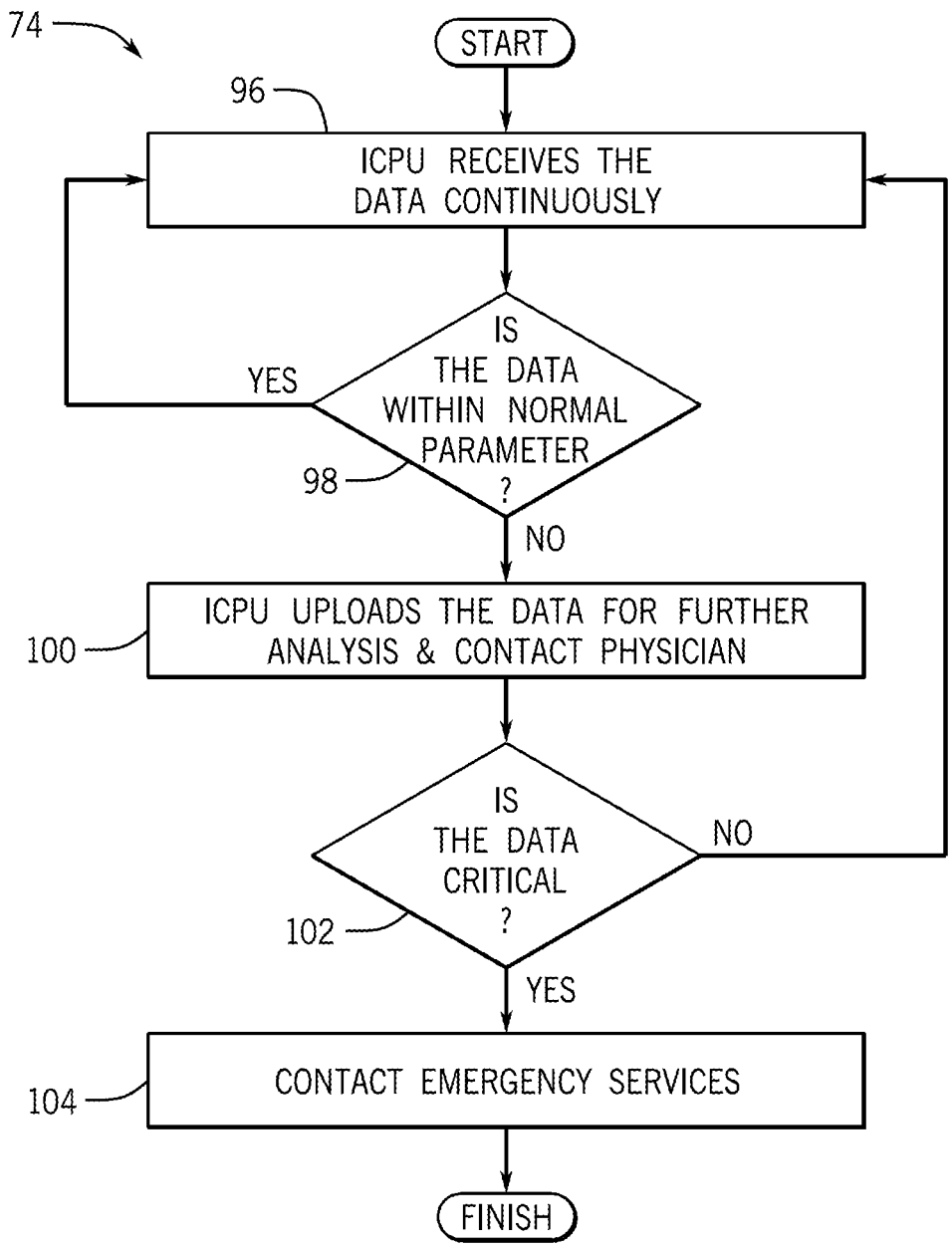
FIG. 7 is a flowchart illustrating the signal analysis function of the body sensor network according to an exemplary embodiment of the invention.

Referring to the exemplary embodiment illustrated in FIG. 7 for the analysis function 74, in block 96, the data from one or more networks/patches 12 is continuously received by the remote network, such as hospital network 62, and in step 98 the data is compared with the normal parameters for that data. If so, the data is disregarded, but if not, the data is uploaded into the network 62 and a physician is contacted in block 100. If the data, upon review by the physician, is determined to be critical in block 102, then emergency services are contacted in block 104. If the data is not deemed to be critical, the data is disregarded.

According to another exemplary embodiment of the invention, the sensor network 12 can be formed to be readily positioned on the body of the individual to be monitored. For example, the sensor network 12 can be affixed to the body of the individual using straps, adhesives or other suitable structures, such as mechanical mechanisms, including hook and loop fasteners. Further, the network 12 may be formed as a multicomponent unit, with various items being located in a base unit that is designed to be secured to the individual and disposed of after use, while other re-usable component can be located in a module unit that can be releasably engaged with the base unit for use, and then removed, re-initialized and re-used with another base unit on another individual. Additionally, the sensor nodes/systems 20-34 can take the form of individual patches that can be placed on various portions of the body of the individual to transmit data in a wired or wireless manner back to the network/module unit 12. These sensor nodes can be activated by the individual pressing or touching the nodes, or can be activated by a signal from the network/module unit 12 or other suitable controller. In this manner, the sensor nodes/systems 20-34 can be operated to measure various parameters of the individual at various times, such as during certain strenuous situation in a game or practice, in order to analyze the body position, stress level and other aspects of the individual during those situations, such as during a swing or other athletic movement being analyzed. Using the multi-modal data collected by the sensor nodes/systems 20-34, it is possible to provide a much more detailed and in depth review of the condition and/or performance of the individual for medical monitoring and/or sports performance enhancement purposes. Further, with the enhancement provided by the multi-modal data obtained by the system 10, the accuracy of the results provided by the system 10 can be up to 97%-99%, well above the 85% accuracy ceiling of prior art monitoring devices.

Further, in the ECG recording and analysis using the sensor/system/module 26, the network 12 can also obtain acoustic cardiographic data using suitable acoustic sensor, such as sensors 28. The combination acoustic data from sensors 28 and the ECG data from sensors 26 can be utilized in an analysis to employ multiple variables in determination of a physical state or diagnosis of the individual which results in a much more accurate diagnosis of the individual. For example, if a tachycardia is observed in an ECG signal there could be two possible diagnosis if we consider only ECG signal. However, using the system 10 and network 12, the additional data point(s) provided by the acoustic sensors 28 and other data can give a definitive and accurate result.

This multi-modal analysis using various parametric data obtained from the network/patches 12 can be utilized to measure and coach athletes using the system 10. For example, if an athlete has various cardiac data recorded during a training session or during actual game play along with the capture of additional motion sensor data, optionally in conjunction with other data, such as GPS data, can be used to determine the level of performance of the athlete from a physical perspective. This data can also be used to correlate the performance of the athlete from an emotional perspective by comparison of the data with data recorded from previous sessions in to ascertain the stress level of the athlete, e.g., was the performance in an actual game situation lessened based on increased stress as compared to a practice session, which can be used to provide indications of how to coach or treat the athlete in subsequent sessions in order to lessen the stress and increase performance and/or reduce injuries, if data was recorded by the network 12 during a session in which an injury was sustained.

Further, the ECG data obtained from the sensors/system 26 can by itself be analyzed to derive multiple physiological parameters for the individual. Such analysis includes the analysis of Heart Rate Variability (HRV). Prior art mentioned here consider R—R interval in time domain as a means to determine HRV, The given sensors/system 10,26 analyzes ECG data obtained from sensors/system 10,26 in time domain, frequency domain, linear domain and non-linear domain to extract twenty-seven (27) different parameters of HRV including:

1. SDNN: Standard deviation of all NN intervals
2. SDANN Standard deviation of the averages of NN intervals in all 5 min segments of the entire recording.
3. RMSSD The square root of the mean of the sum of the squares of differences between adjacent NN intervals.
4. SDNN index Mean of the standard deviations of all NN intervals for all 5 min segments of the entire recording.
5. SDSD Standard deviation of differences between adjacent NN intervals.
6. NN50 count Number of pairs of adjacent NN intervals differing by more than 50 ms in the entire recording.
7. Three variants are possible counting all such NN intervals pairs or only pairs in which the first or
8. the second interval is longer.
9. pNN50: NN50 count divided by the total number of all NN intervals.
10. Geometric measures
11. HRV triangular index Total number of all NN intervals divided by the height of the histogram of all NN intervals measured on a discrete scale with bins of 7·8125 ms (1/128 s).
12. TINN: Baseline width of the minimum square difference triangular interpolation of the highest peak of the
13. histogram of all NN intervals
14. VLF Power in very low frequency range |0·04 Hz
15. LF Power in low frequency range 0·04-0·15 Hz
16. LF norm. LF power in normalized units
17. LF/(Total Power−VLF)#100
18. HF: Power in high frequency range 0·15-0·4 Hz
19. HF norm: HF power in normalized units
20. HF/(Total Power−VLF)*100
21. LF/HF Ratio LF [ms2]/HF [ms2]
22. Total power: Variance of all NN intervals approximately |0·4 Hz
23. ULF: Power in the ultra low frequency range |0·003 Hz
24. VLF: Power in the very low frequency range 0·003-0·04 Hz
25. LF: Power in the low frequency range 0·04-0·15 Hz
26. HF: Power in the high frequency range 0·15-0·4 Hz
27. á: Slope of the linear interpolation of the approximately |0·04 Hz These 27 parameters are unique to individuals and dependent analysis of these parameters can lead to even more accurate diagnoses of the individual. These parameters can be used to further determine the physical and emotional state of the individual, and can be accomplished with only the ECG signals from sensors/system 26. As such, the network 12 can be used with the ECG sensors/system 26 alone, or with other sensors/sensor modules 20-24, 28-34 in order to improve the data points available for the resulting analysis of the performance or condition of the individual, depending upon the situation.

Figure 16:
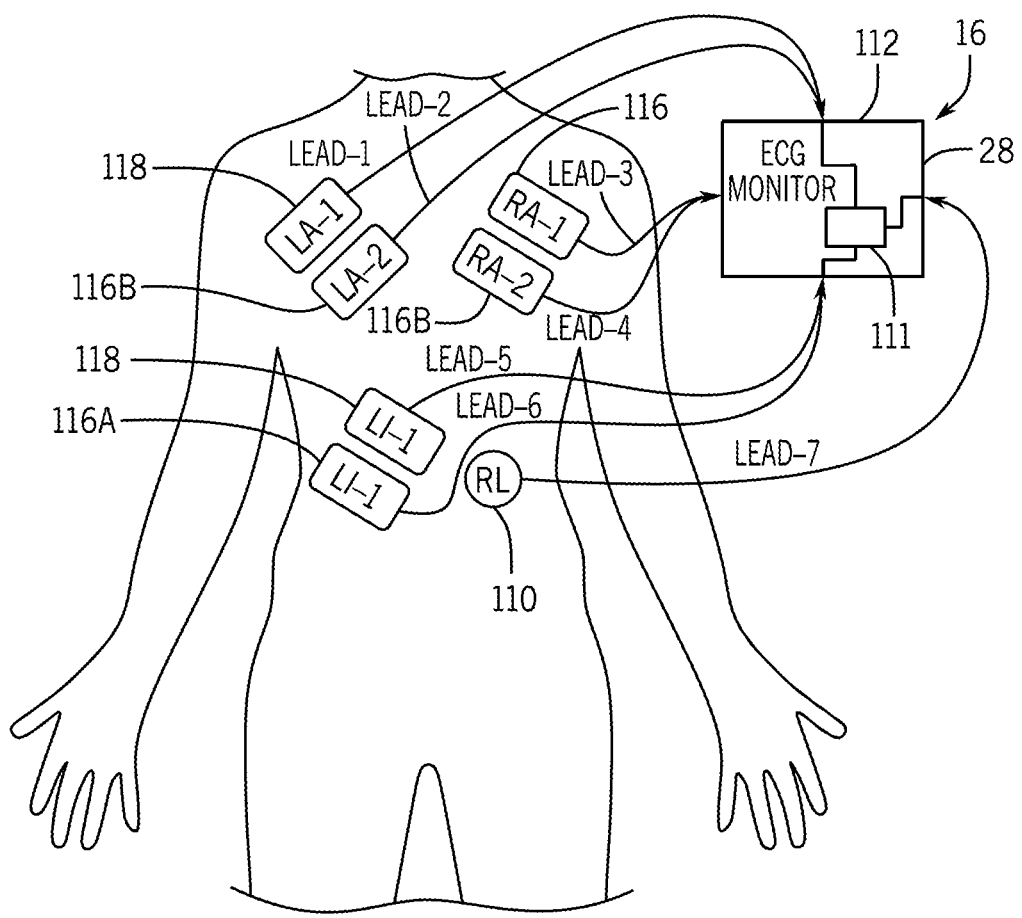
FIG. 16 is a schematic view of an ECG test set up according to one exemplary embodiment of the invention.

To enable the ECG recording sensors/system/module 26 to obtain signals for analysis with a reduction in the noise within the measured signals, according to one exemplary aspect of the invention illustrated in FIG. 16, the ECG sensor/system 26, as well as other sensors/sensor modules 20-24,28-34, is formed with and/or as a monitoring device 112 that includes a central processing unit 111 and three sets of paired or double leads/electrodes 114,114A, 116,116A and 118,118A, as well as lead 120, which are positioned on or adjacent the left arm, right arm, left leg and right leg, respectively, of the individual/patient 122 being monitored.

The monitor 112 is operated in a known manner to obtain ECG signals from the patient 122 via the leads 114-120. The placement of the leads 114-120 can be varied on the patient 122, and added leads 114A, 116A and 118A each provide an additional data point to isolate noise from the signals obtained at leads 114, 116 and 118. The equations which describe the signals obtained from a lead 114 are:

$$\text{ECG\_Lead }114(t)=\text{ECG\_LA}(t)+\text{Noise}(t)$$

Where,

ECG_Lead 114 represents the time variant signal obtained at lead 114 at time (t).

ECG_LA represents the true ECG Left Arm signal at time (t)

Noise represents any non-ECG component in the system at time (t) Similarly, the signal at lead 114A is, $$ECG\_Lead\ 114A(t) = ECG\_LA(t+t_d) + Noise(t)$$

where:

ECG_Lead 114A represents the time variant signal obtained at lead 114A

ECG_LA represents the true ECG Left Arm signal

Noise represents any non-ECG component in the system $t_d$ represents a time delay taken by the signal to propagate from Lead 114 to Lead 114A.

(these equations are also applicable to the pairs of signals obtained at leads 116,116A and 118,118A as well as for use in noise reduction of other types of signals obtained by the system 10/module, such as PPG signals, among others, or to any signal obtained from the body provided it is obtained in pairs and the measurements are taken at a particular distance from each other)

Figure 17:
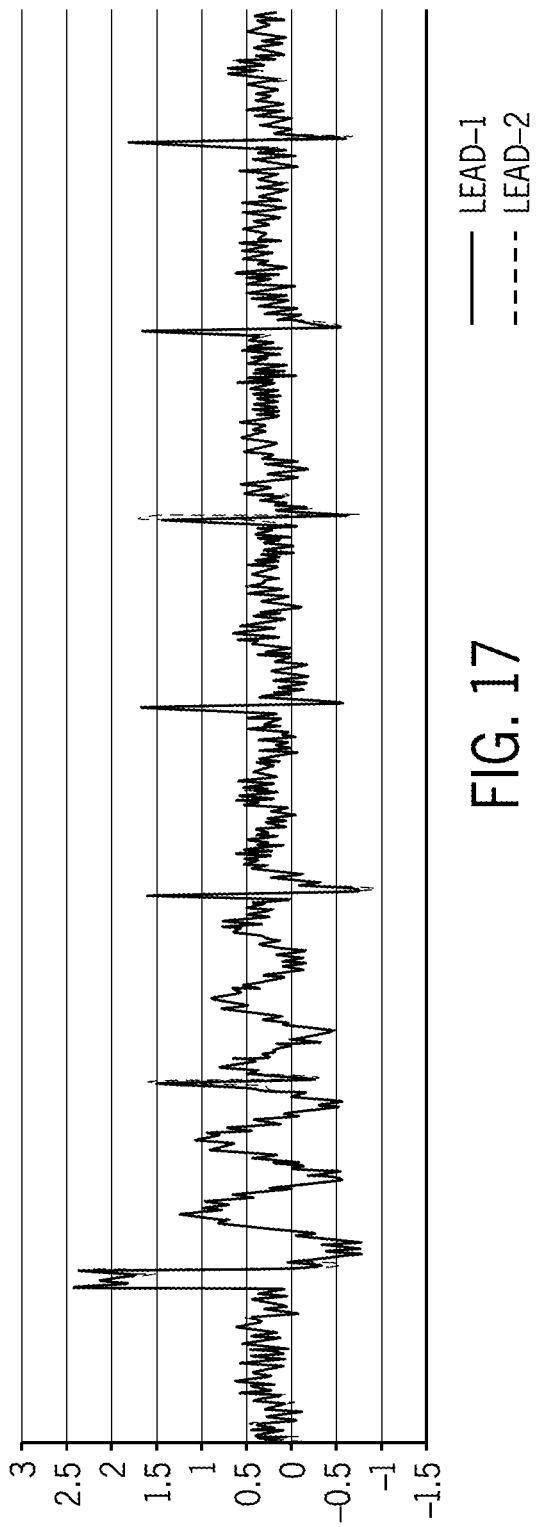
FIG. 17 is a graph of ECG data with Lead-1, Lead-2 with noise and motion artefact from the set up of FIG. 18.
Figure 18:
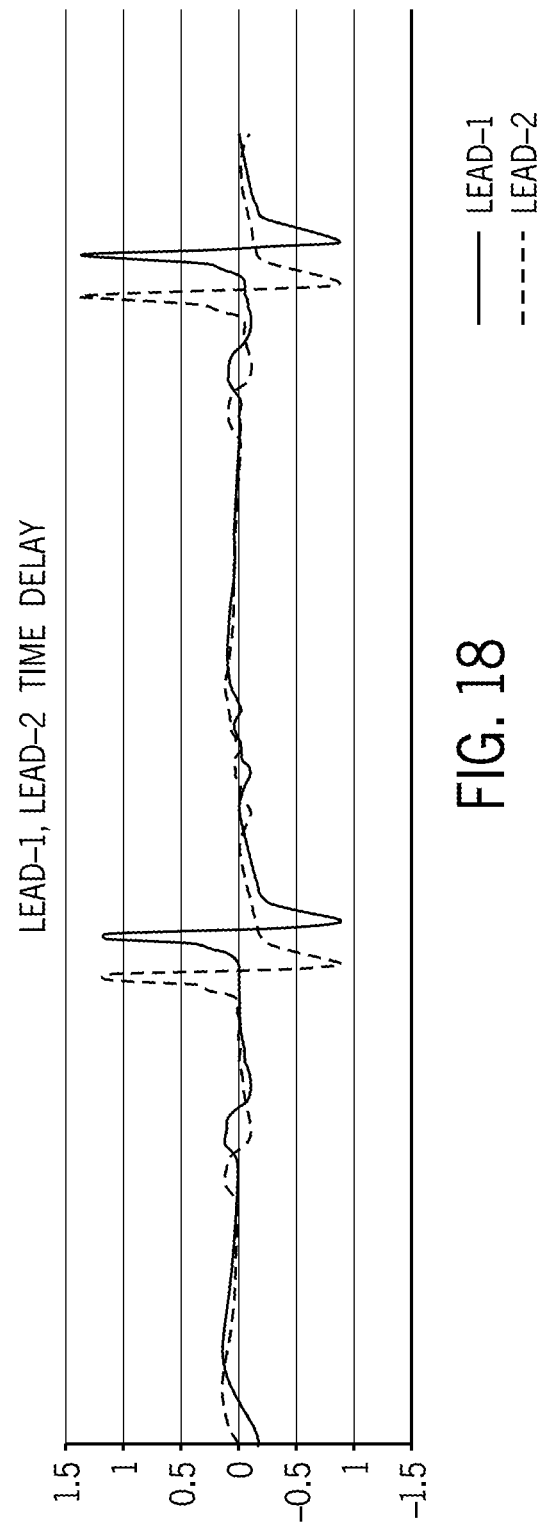
FIG. 18 is a graph of the delay provided in the ECG data of FIG. 17 obtained from Lead-1 and Lead 2.

The advantage of the extra lead 114A is the clear non-zero delayed noise correlation between the signals obtained at the two similarly placed leads 114,114A and the ability to reject the ECG signal in its entirety due to the availability of a fixed time delay based signal available from the signal obtained from the second ECG lead 114A, as shown in FIGS. 17 and 18. Further, the above equations can be utilized with respect to signals from any of the pairs of leads provided in this or any other embodiment of the system 10.

Figure 19:
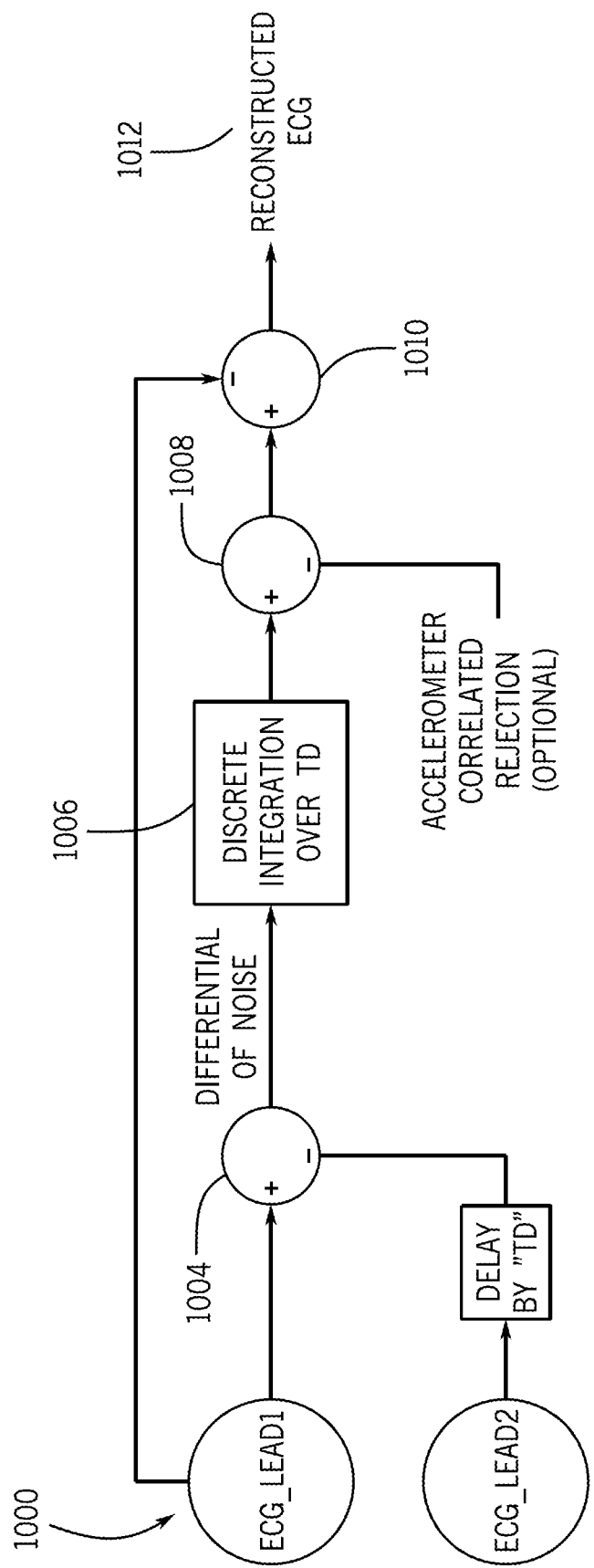
FIG. 19 is a schematic view of the signal extraction procedure according to one exemplary embodiment of the invention.

The main idea of this exemplary embodiment is to gain an idea of the variability of time delay $t_d$ from both a physiological perspective and a signal processing standpoint. Once this time delay is known, the noise signal will be extracted through an integration over the same delay of the ECG and then be removed from the actual noise. This approach also allows for other independent noise sources (i.e., accelerometer) to be identified and rejected easily. As illustrated in the exemplary embodiment of the extraction process shown in FIG. 19, in step 1000 lead 114 (lead-1) obtains an ECG signal from the patient 122. In step 1002, lead 114A (lead-2) obtains the same signal but with a time delay $t_d$ as a result of the time it takes for the signal to reach the position of lead 114A from the position of lead 114. The signals are combined in step 1004 and a discrete integration of the combined signals is performed in block 1006. In block 1008 an optional rejection of motion/accelerometer signals can be performed. In step 1010, the noise signal resulting from the extraction is removed from the corrupted ECG signal obtained in step 1000, resulting in a reconstituted and true ECG signal 1012 that can be analyzed.

Figure 20:
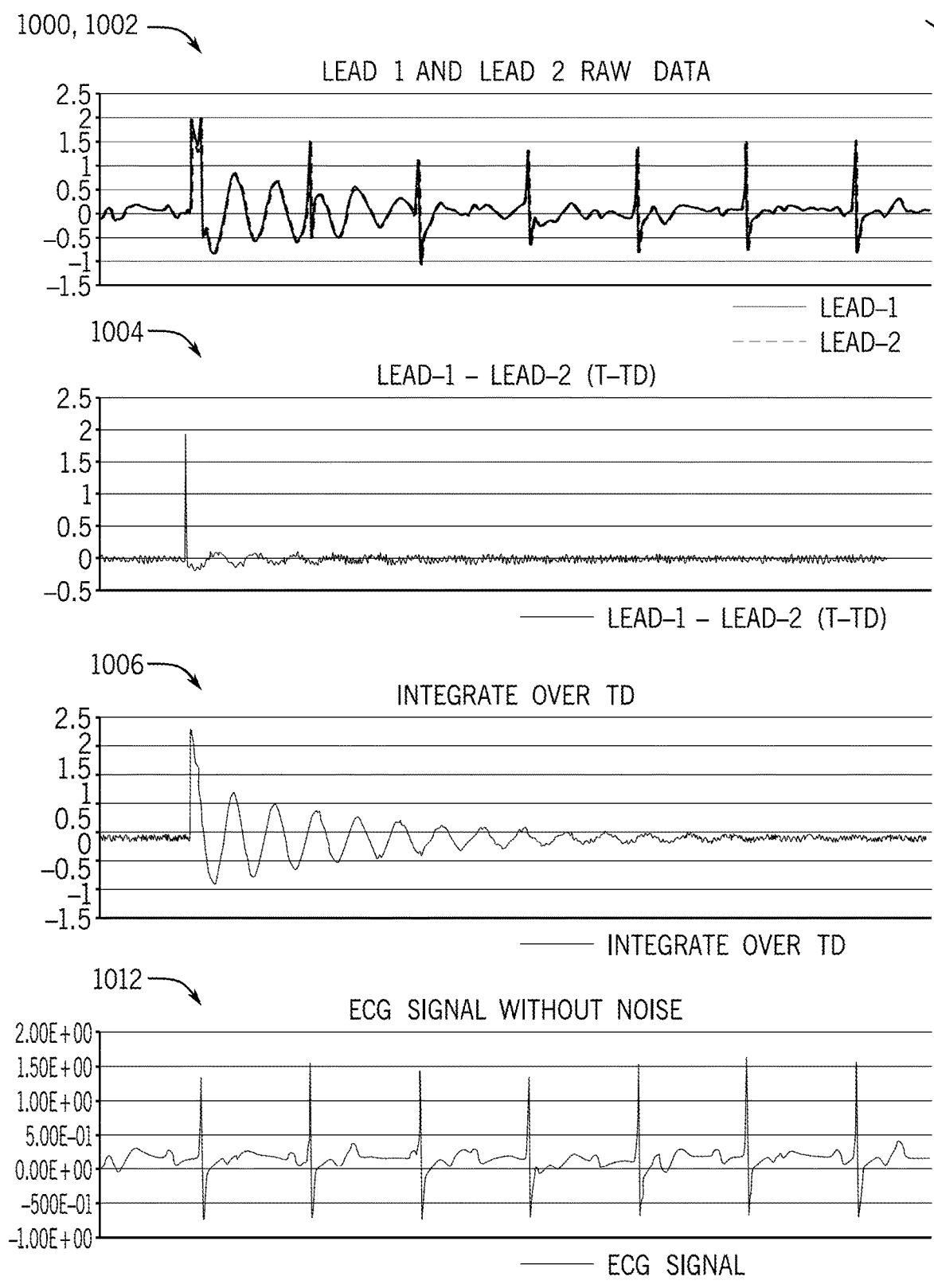
FIG. 20 is a graph of the ECG data of FIG. 17 during the steps of the extraction procedure of FIG. 19.
Figure 21:
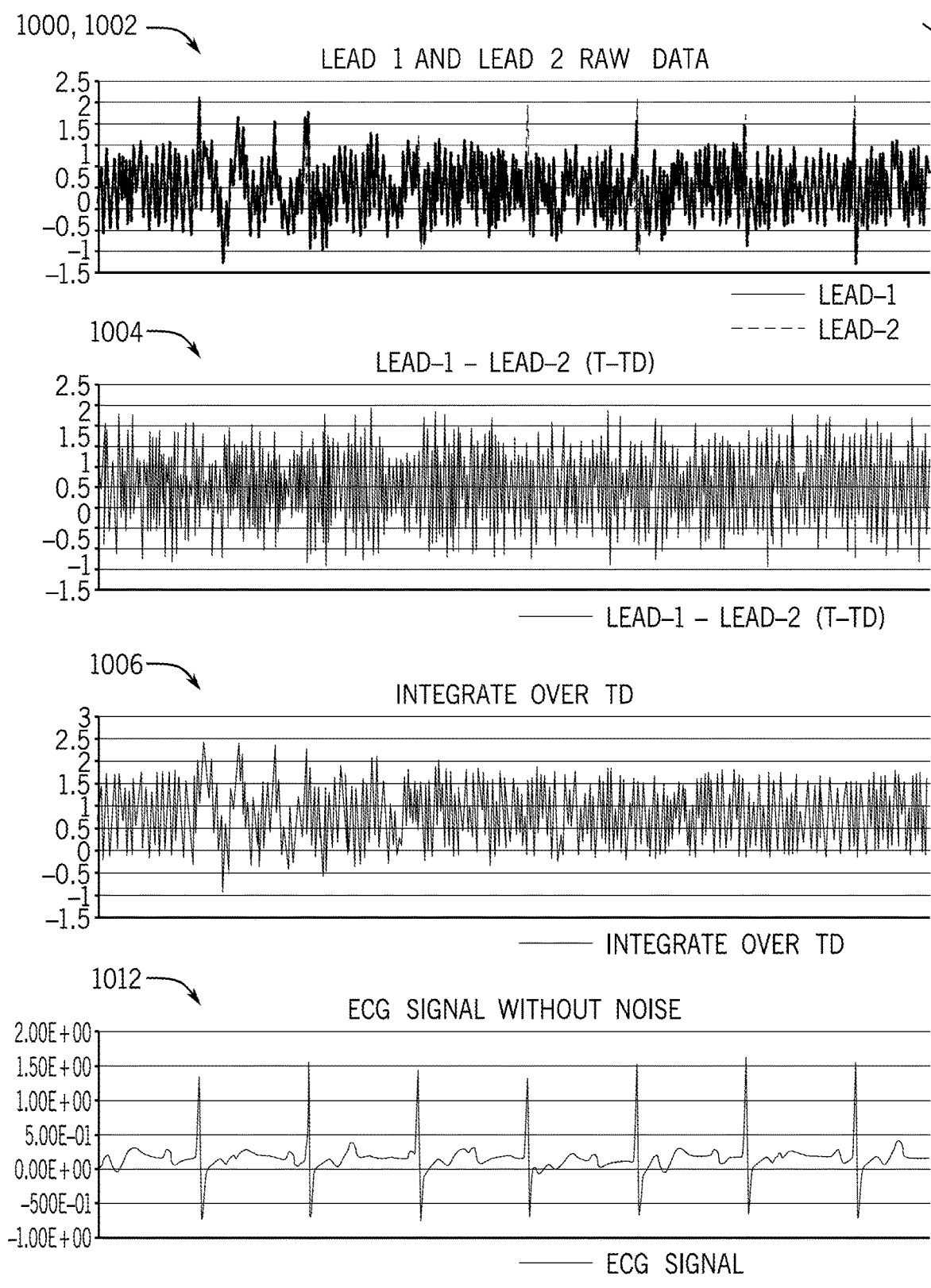
FIG. 21 is a graph of high noise ECG data during the steps of the extraction procedure of FIG. 19.

Examples of the extraction process are illustrated in FIG. 20 on an ECG signal with a low frequency motion artefact component and in FIG. 21 on an extremely high noise and motion artefact corrupted ECG signal. In each case, the resulting reconstituted ECG signal can readily be analyzed to determine the condition of the patient 122.

In certain situations, the ECG sensor/system 26 is formed as a three (3) lead ECG system to provide physiological data on an individual. However, with the advent of improved twelve (12) lead ECG systems, three (3) lead ECG systems are used sparingly due to the reduced amount of data provided on the individual.

To attempt to address this shortcoming, different approaches have been taken to try and reconstruct the signals that would be obtained from a 12 lead/sensor ECG system utilizing only the signals obtained from a 3 lead/sensor ECG system.

The use of a universal matrix is inappropriate for reconstruction of missing leads with a reduced lead system. Dawson's et. al [1] recent work provides a marginal improvement to Dower's [3] developments over the past 40 years. The newly developed transformation matrix derived from regressions of linear affine transformations still lacks in modifying waveform morphology. Charzal and Celler's [10] research also states that the use of universal matrix is inappropriate. Their research showed that some use cases of the universal transform worked perfectly with a 1.00 correlation while some applications failed with a negative correlation of −0.63. Matching transformation matrix to patient using individual adjustments or by placing patients in a predefined set of population with a population-specific coefficient is the new future of transformation matrices as performed by Man et al [11].

One of the primary reasons for the use of a 12-lead ECG system is the redundant information produced by the 12-lead ECG system helps to offset the effect of electrode misplacement. Even if one lead is misplaced which can happen quite frequently according to Schijvenaars [4] and other references, the cardiologist can make a diagnosis based on the information collected from the other leads, since the information contained by that lead was also present in the other leads.

Conversely, if we consider the 3-lead ECG system, the misplacement of one lead can result in invalidation of the entire set of measurements. The reduced lead system lacks reliability and redundancy is a problem with 3-lead ECG system. Compensating the misplacement of lead with a monolithic sensor patch, dynamic co-relation and noise cancellation technique can provide reliable set of 3-lead ECG for re-construction purpose. FICA (Fast independent component analysis) can further help to solve this problem. FICA can provide the underlying independent biosignal sources independent of the electrode placement. Considering a simple model, heart's electrical activity is a single dipole, comprising of 3 statistically independent, orthogonal sources. Gulrajani [24] gives an elaborate description of different types of models that can be used. However the single dipole model is the simplest and an effective method which needs 3 leads minimum to unmix to the original source. The three (3) orthogonal directions of the heart dipole and noise source can be found using four lead with FICA. In short the sino-atrial and sino-ventricular nodes, which are original sources for producing the synchronization pulse for the heart called ECG, are traced.

However the given method lacks precision in the sense, the transform matrix is calculated considering patient is in same position throughout the measurement. The model fails to reconstruct accurate ECG if the patients move or relative position of the reduced set of leads changes with respect to heart.

As of now FICA is not used to compensate for misplacement of the electrodes but this might be the near future of ECG monitoring. Only 1 or 2 electrodes need to be positioned correctly by performing constrained FICA. The electrodes will provide 2 out of 3 signals sources of the single dipole model and will be used as references. The other subsequent sources can be generated by hazardously positioned electrodes. The 12-lead ECG reconstruction can be done considering that the position of the initial electrodes is known and assuming that patient-specific transform coefficient are known to the patient. Thus reconstruction can be done in its entirety from a set of minimum leads without fearing misdiagnosis from the main source of intra-individual variability electrode placement. However, the independent components of the ECG system need to be generated reliably with high level of spatial and temporal independence, also it is important to overcome the sorting problem.

As a result, 3-lead to 12-lead ECG reconstruction has been a hot topic of research and many methodologies have been proposed till now, majority of being revolving around the Universal transform method. Our initial tests showed that reproducing 12-lead ECG from a reduced set of stationary ECG leads using static universal transform was not effective. The major reason for failure for this technology lies in the fact that Universal Transform adopted a flawed model that assumed all patients to be similar [2]. In fact, every individual has their own characteristic set of body vitals and consequently the base line drastically varies from person to person.

Figure 22:
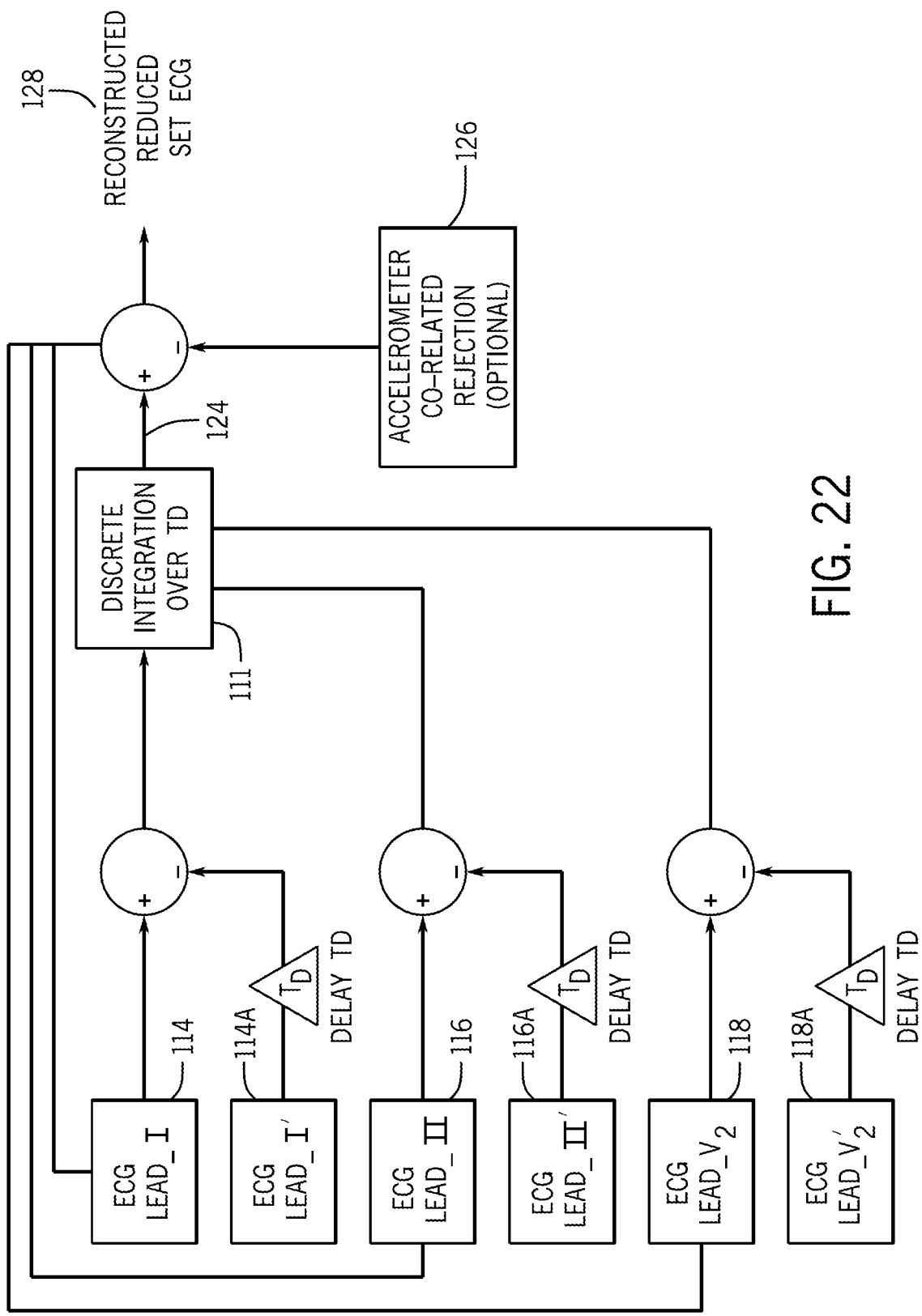
FIG. 22 is a schematic view of a reduced lead ECG system according to an exemplary embodiment of the invention.

Various studies have showed that patient specific transforms can produce more promising results. Patient specific transform method is majorly based on the technique called ICA (Independent component analysis). The system and technique described in this exemplary embodiment of the invention and results illustrated in FIGS. 22-34D is based on dynamic Independent component analysis (ICA) performed in a central processing unit (not shown) disposed within or operably connected to the within the system 26 that is configured to which takes into consideration the co-related reduced set of ECG to re-construct 12-lead ECG, such as using the system 10 as illustrated in the exemplary and non-limiting embodiment of FIG. 22 in which the system 10 includes the ECG monitoring sensors/system 26 including leads 114,114A,116,116A,118,118, as well as lead 120 (though not shown in FIG. 22). Signals from each of pairs of leads 114-118A are combined and processed in CPU 111 using a discrete integration technique. This discrete integration output 124 from CPU 111 is subsequently combined with signals from leads 114, 116 and 118 and an optional accelerometer co-related rejection 126, to arrive at the reconstructed ECG signal set 128.

Our results have shown that the given methodology has significant merit over any other existing method for 3-lead to 12-lead ECG reconstruction with construction efficiency lying in the higher order of 96% accuracy. Patient-specific transform thus reduces the error that may be caused due to misplacement of leads in both residential and clinical environment by providing accurate reproduced ECG from different set of leads and same underlying sources of ECG. The initial experiments gave a representation of case with misplaced set of electrodes, these experiments used different sets of leads for generating independent sources derived from standard set of precordial leads.

Figure 23:
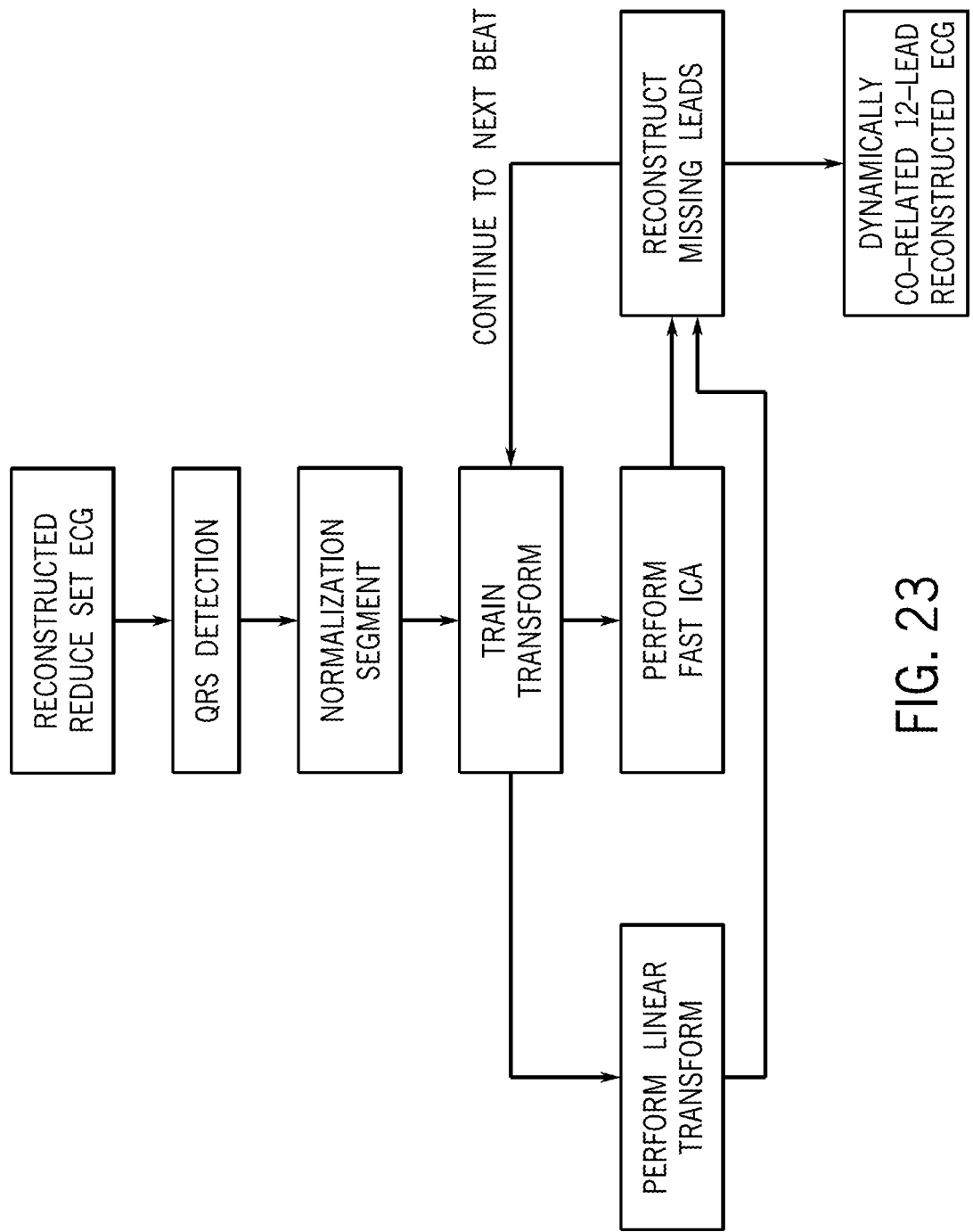
FIG. 23 is a schematic view of a method of operation of the reduced lead ECG system according to an exemplary embodiment of the invention.
Figure 24A:
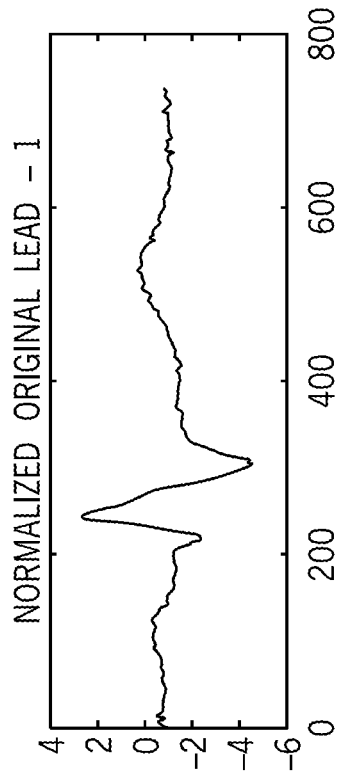
FIGS. 24A-24D are graphs of the signals of original lead 1, normalized original lead 1, normalized ICA reconstructed lead 1 and linear reconstructed lead 1 obtained according to an exemplary embodiment of the invention.
Figure 24B:
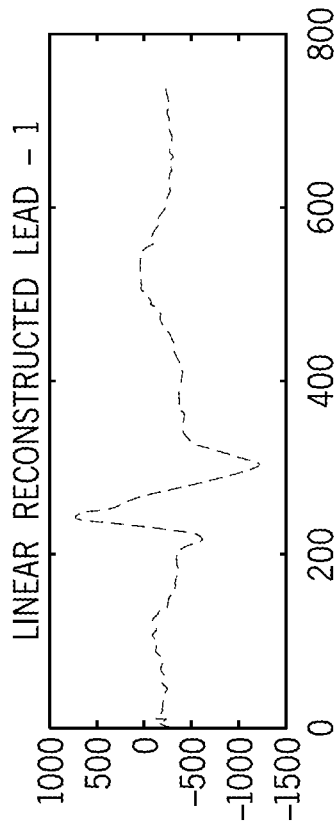
Figure 24C:
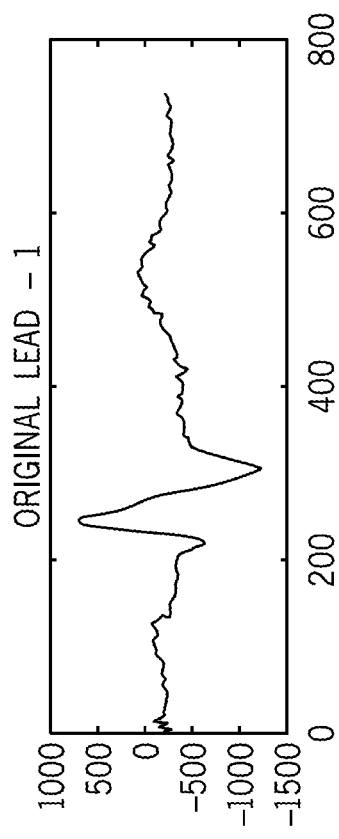
Figure 24D:
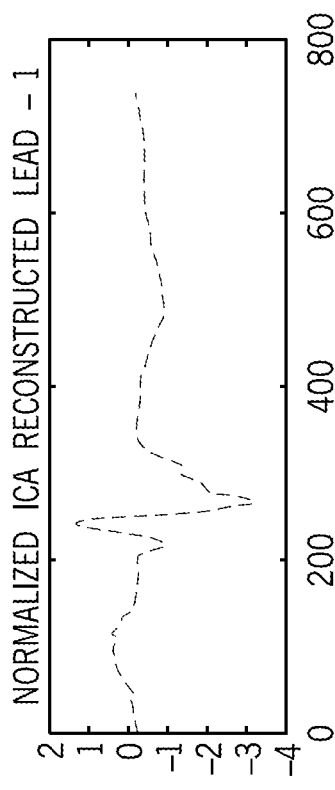
Figure 25A:
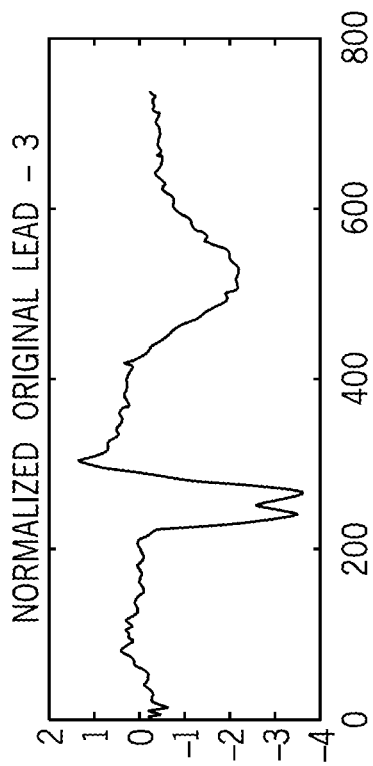
FIGS. 25A-25D are graphs of the signals of original lead 3, normalized original lead 3, normalized ICA reconstructed lead 3 and linear reconstructed lead 3 obtained according to an exemplary embodiment of the invention.
Figure 25B:
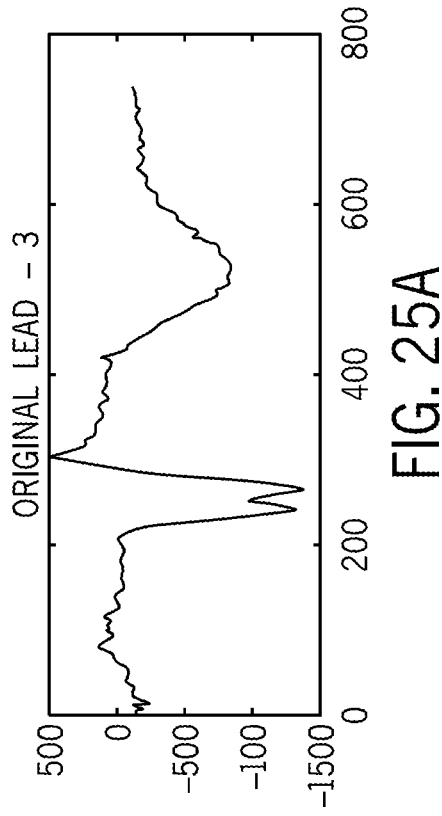
Figure 25C:
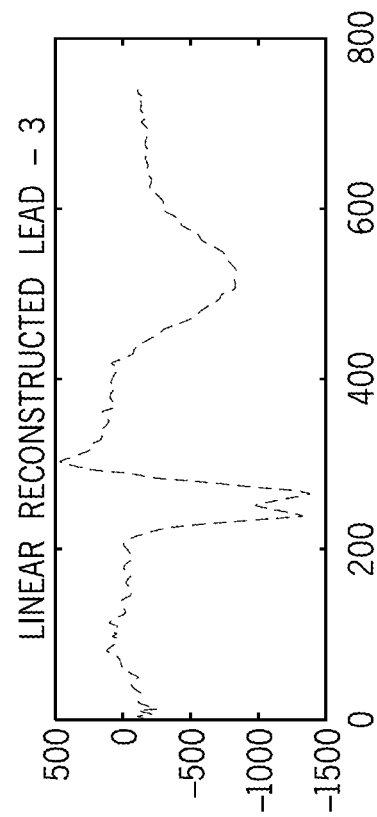
Figure 25D:
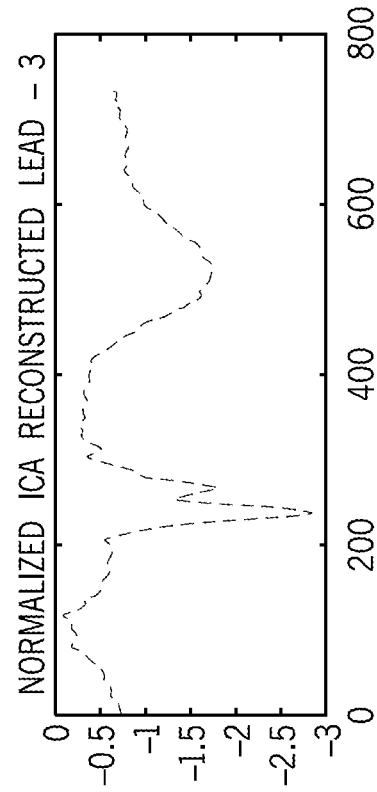
Figure 26B:
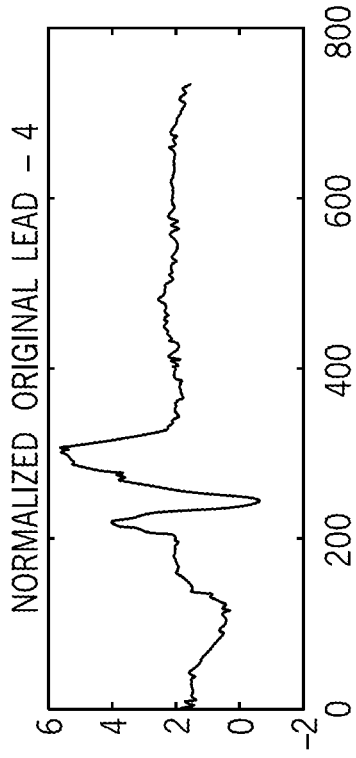
FIGS. 26A-26D are graphs of the signals of original lead 4, normalized original lead 4, normalized ICA reconstructed lead 4 and linear reconstructed lead 5 obtained according to an exemplary embodiment of the invention.
Figure 26D:
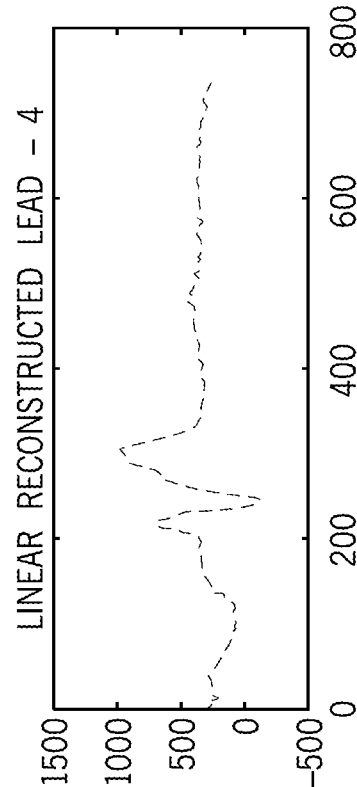
Figure 26A:
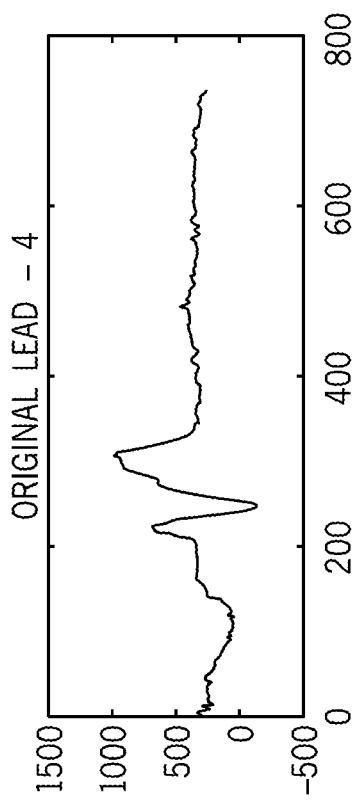
Figure 26C:
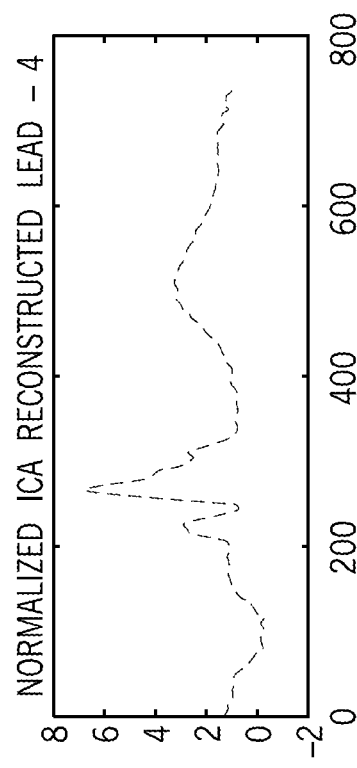
Figure 27B:
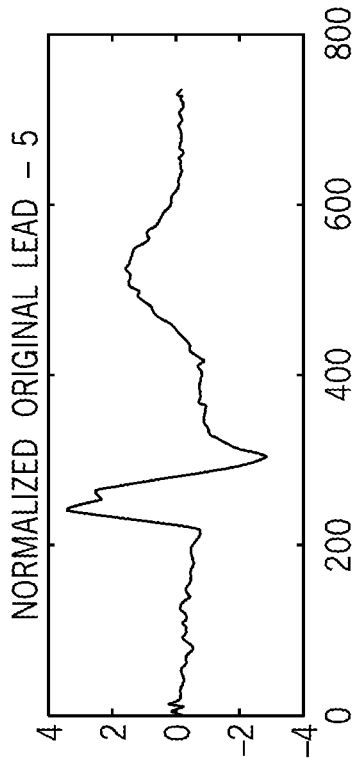
FIGS. 27A-27D are graphs of the signals of original lead 5, normalized original lead 5, normalized ICA reconstructed lead 5 and linear reconstructed lead 5 obtained according to an exemplary embodiment of the invention.
Figure 27D:
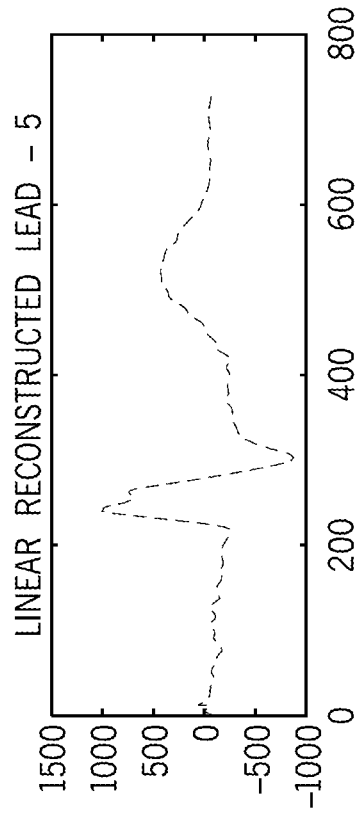
Figure 27A:
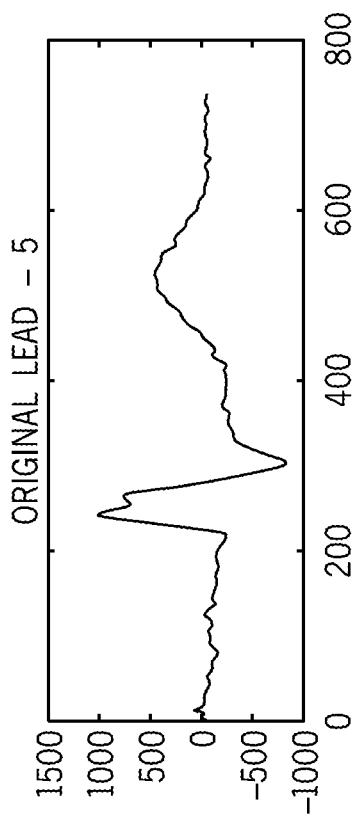
Figure 27C:
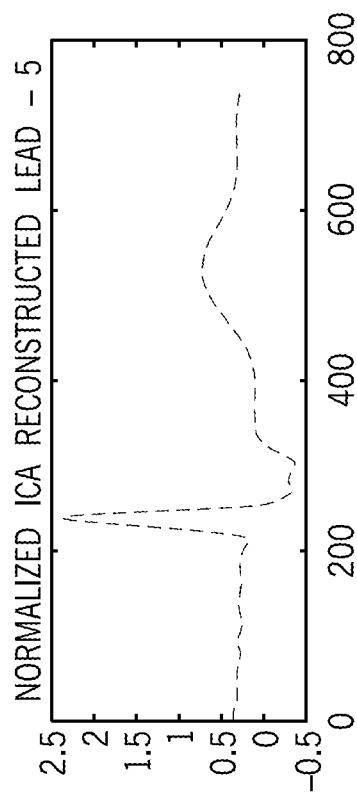
Figure 28B:
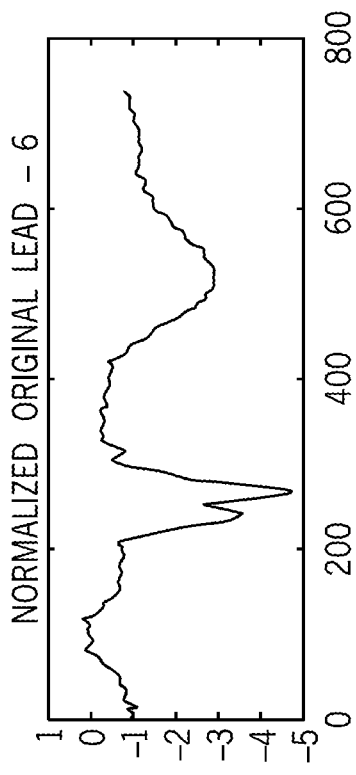
FIGS. 28A-28D are graphs of the signals of original lead 6, normalized original lead 6, normalized ICA reconstructed lead 6 and linear reconstructed lead 6 obtained according to an exemplary embodiment of the invention.
Figure 28D:
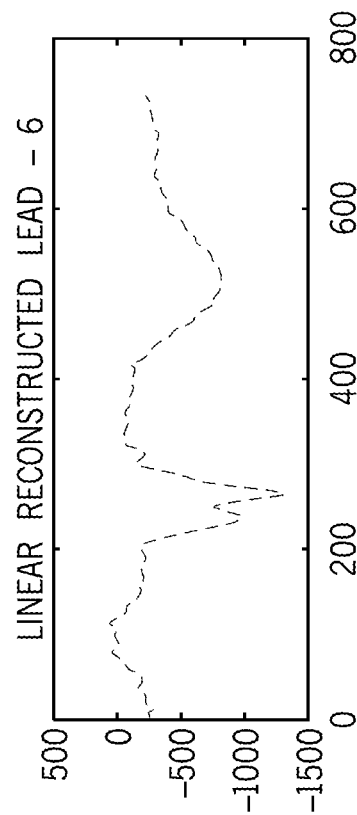
Figure 28A:
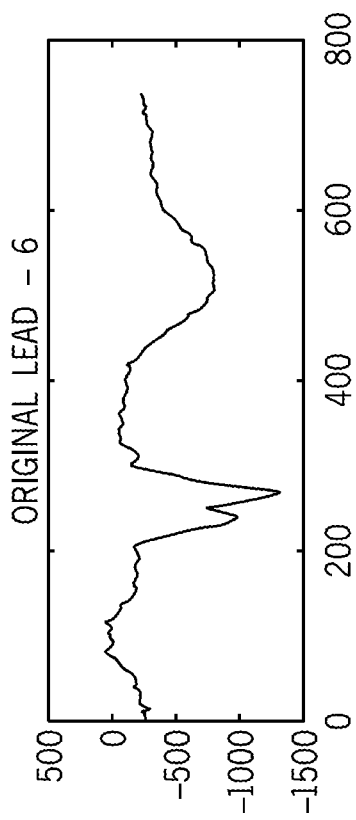
Figure 28C:
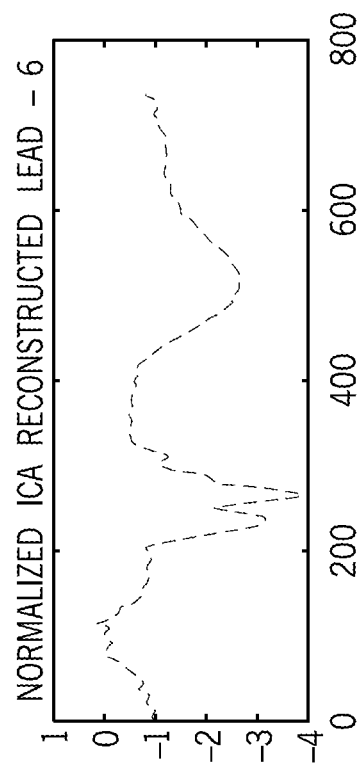
Figure 29B:
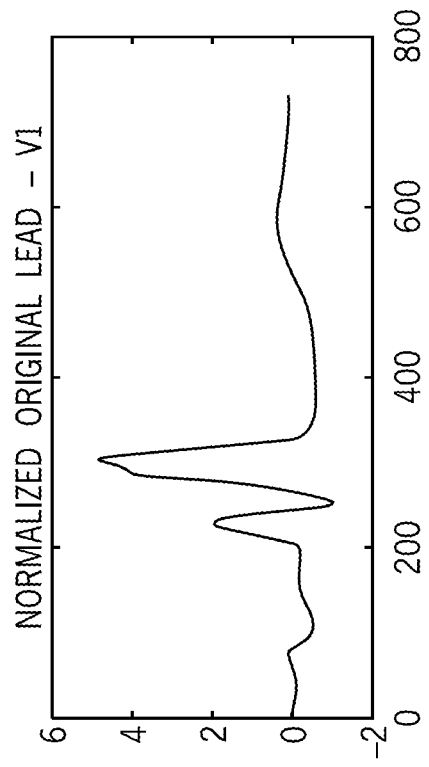
FIGS. 29A-29D are graphs of the signals of original lead V1, normalized original lead V1, normalized ICA reconstructed lead V1 and linear reconstructed lead V1 obtained according to an exemplary embodiment of the invention.
Figure 29D:
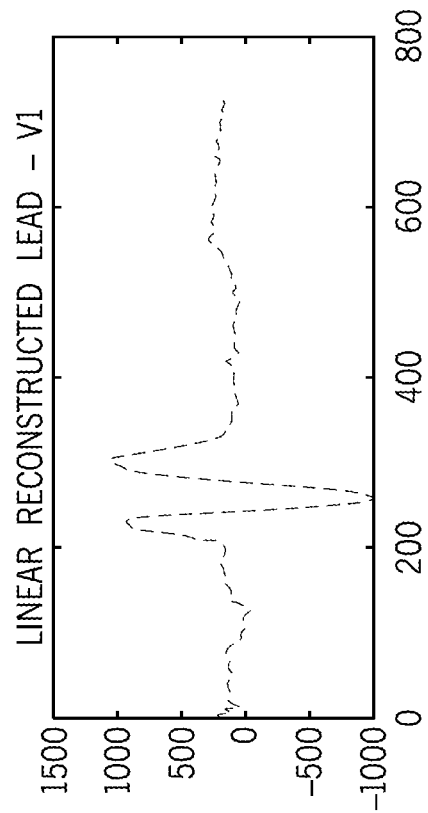
Figure 29A:
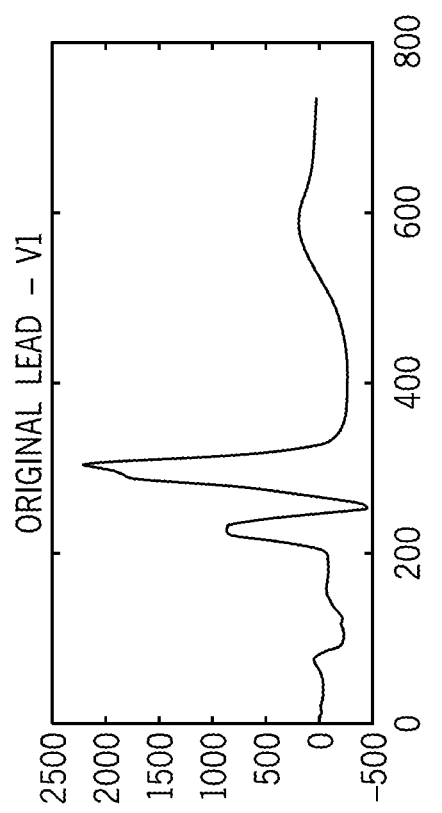
Figure 29C:
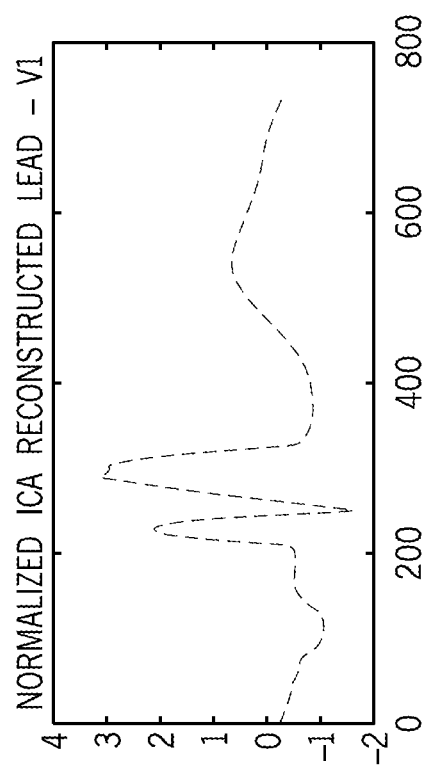
Figure 30A:
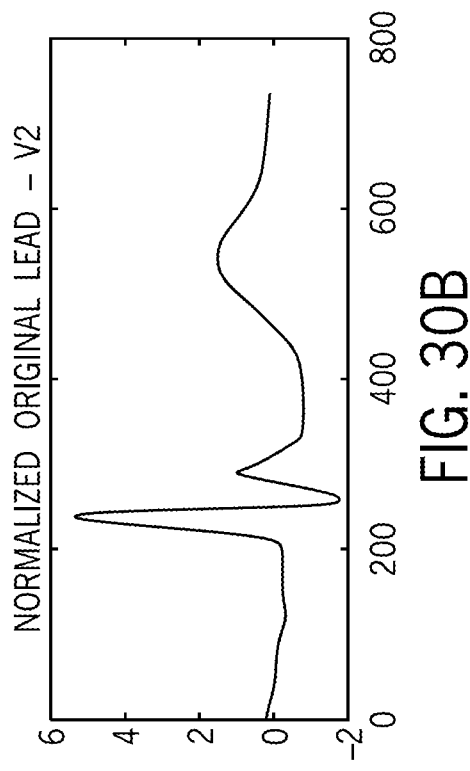
FIGS. 30A-30D are graphs of the signals of original lead V2, normalized original lead V2, normalized ICA reconstructed lead V2 and linear reconstructed lead V2 obtained according to an exemplary embodiment of the invention.
Figure 30B:
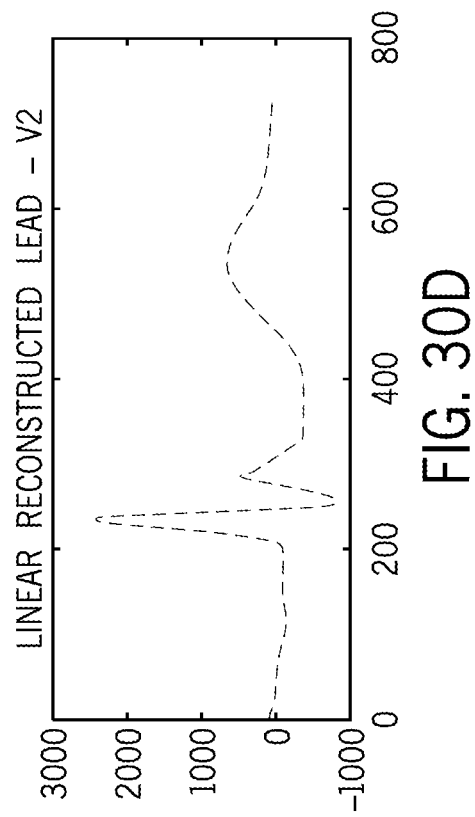
Figure 30C:
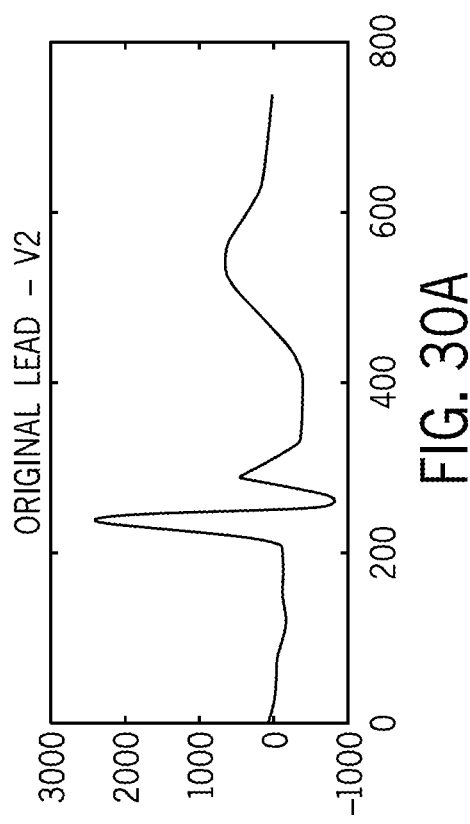
Figure 30D:
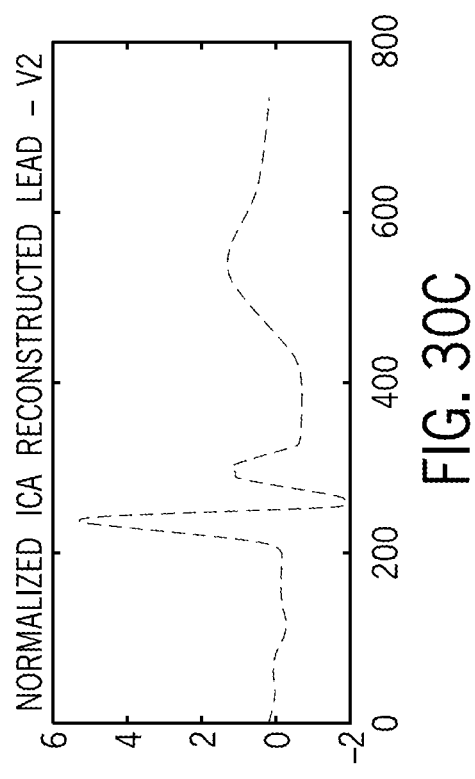
Figure 31B:
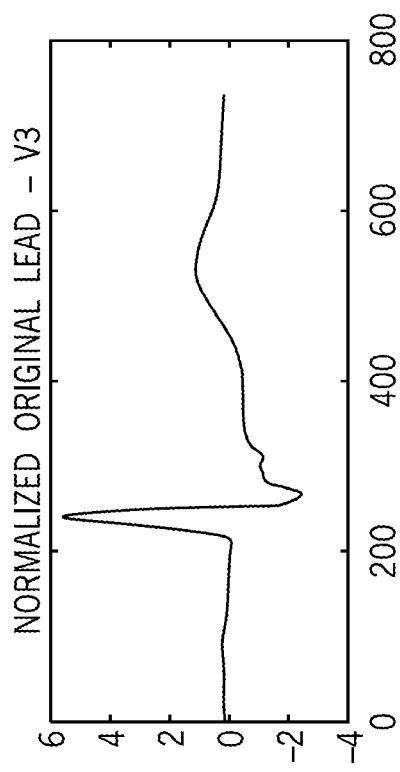
FIGS. 31A-31D are graphs of the signals of original lead V3, normalized original lead V3, normalized ICA reconstructed lead V3 and linear reconstructed lead V3 obtained according to an exemplary embodiment of the invention.
Figure 31D:
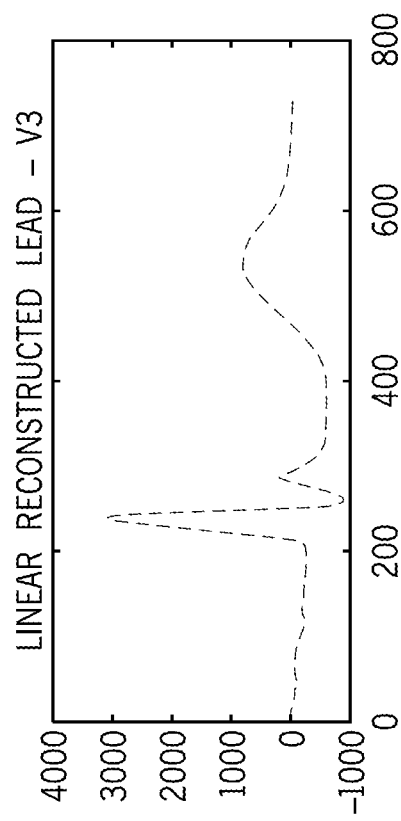
Figure 31A:
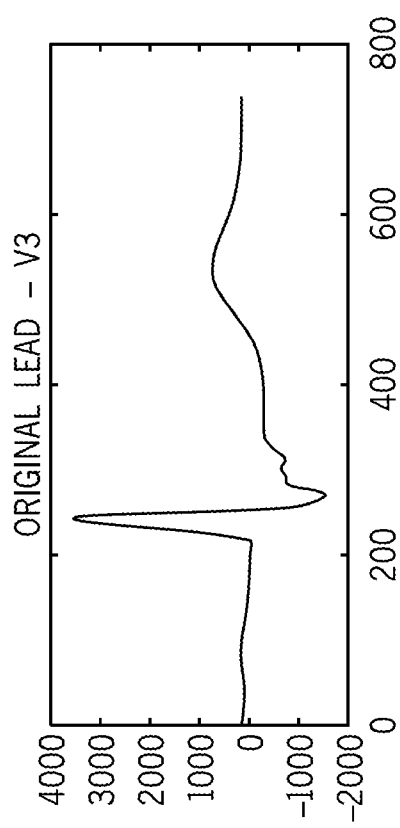
Figure 31C:
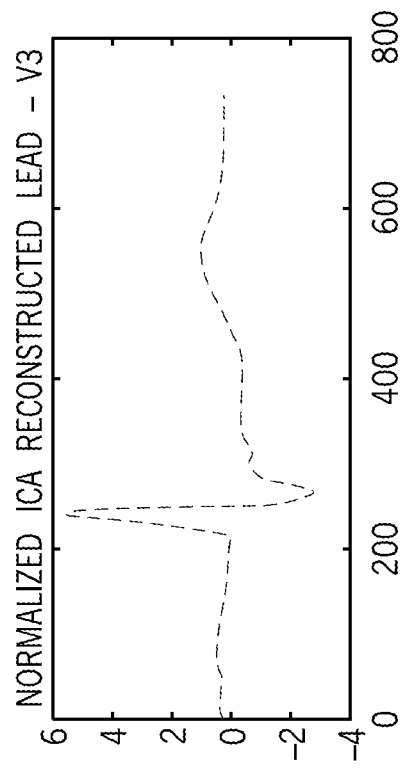
Figure 32A:
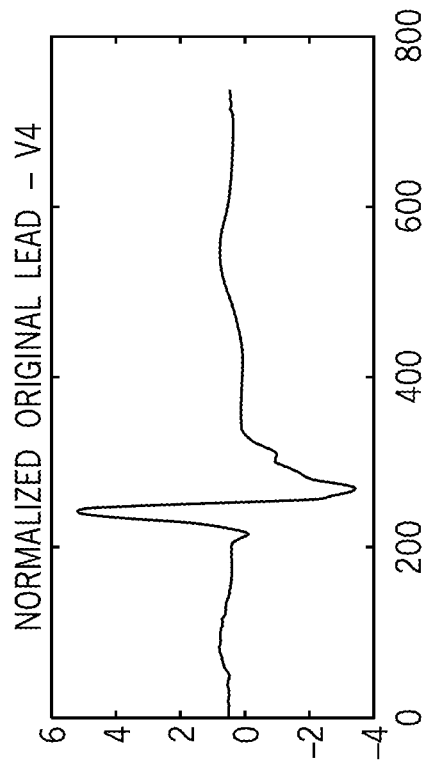
FIGS. 32A-32D are graphs of the signals of original lead V4, normalized original lead V4, normalized ICA reconstructed lead V4 and linear reconstructed lead V4 obtained according to an exemplary embodiment of the invention.
Figure 32B:
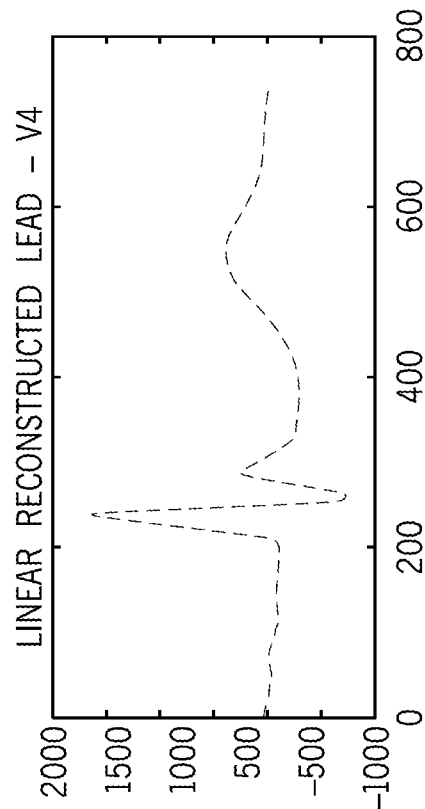
Figure 32C:
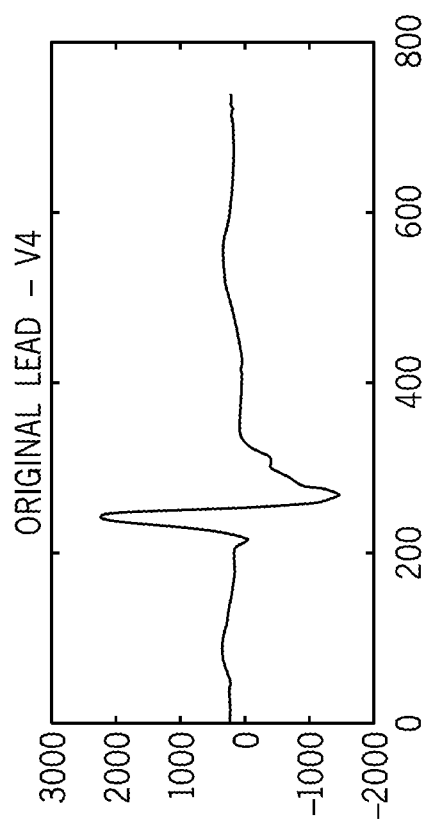
Figure 32D:
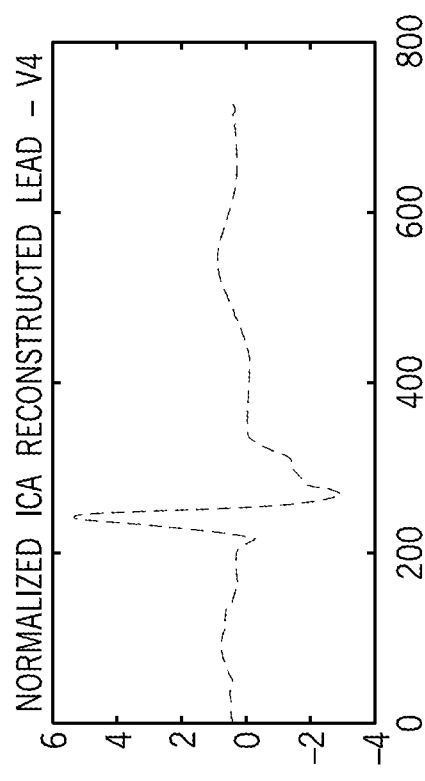
Figure 34A:
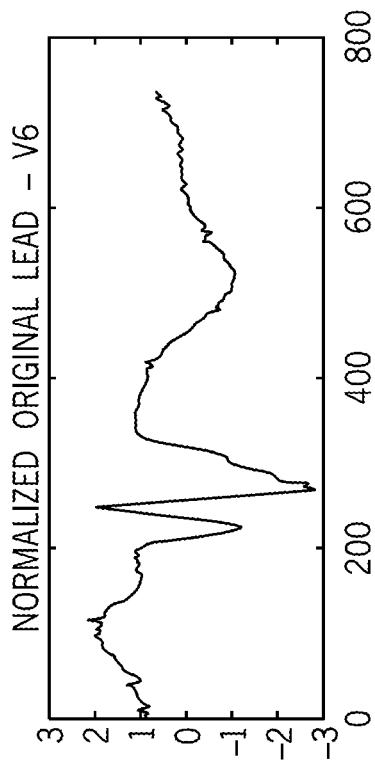
FIGS. 34A-34D are graphs of the signals of original lead V6, normalized original lead V6, normalized ICA reconstructed lead V6 and linear reconstructed lead V6 obtained according to an exemplary embodiment of the invention.
Figure 34B:
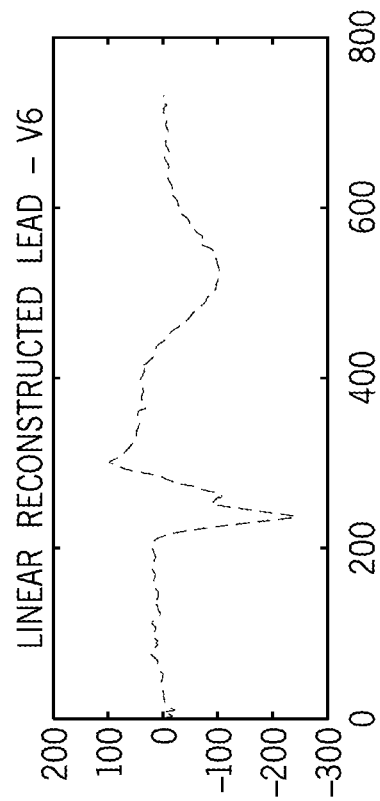
Figure 34C:
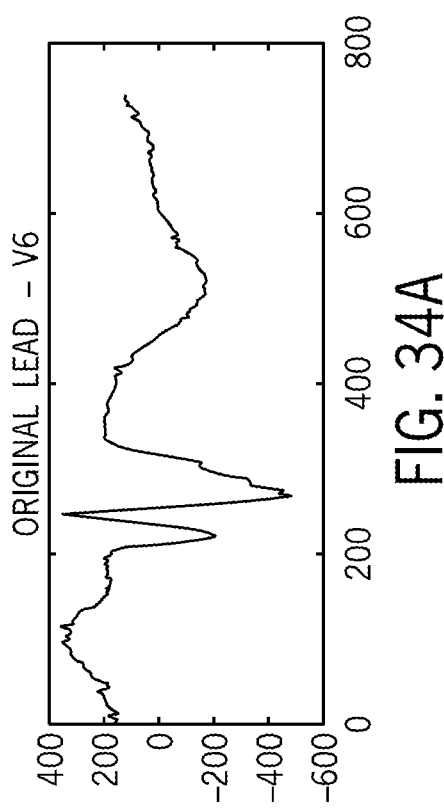
Figure 34D:
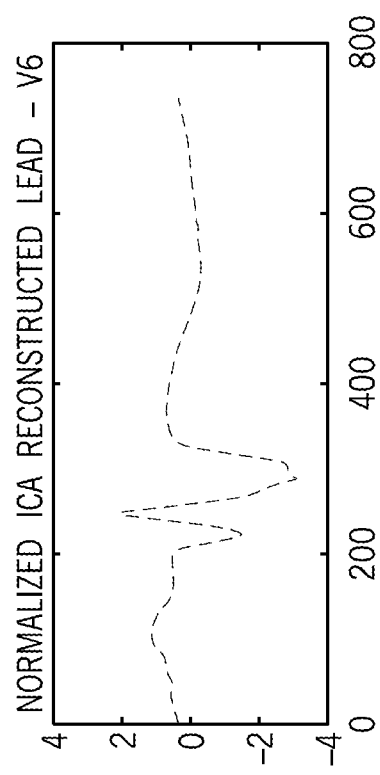
Figure 35:
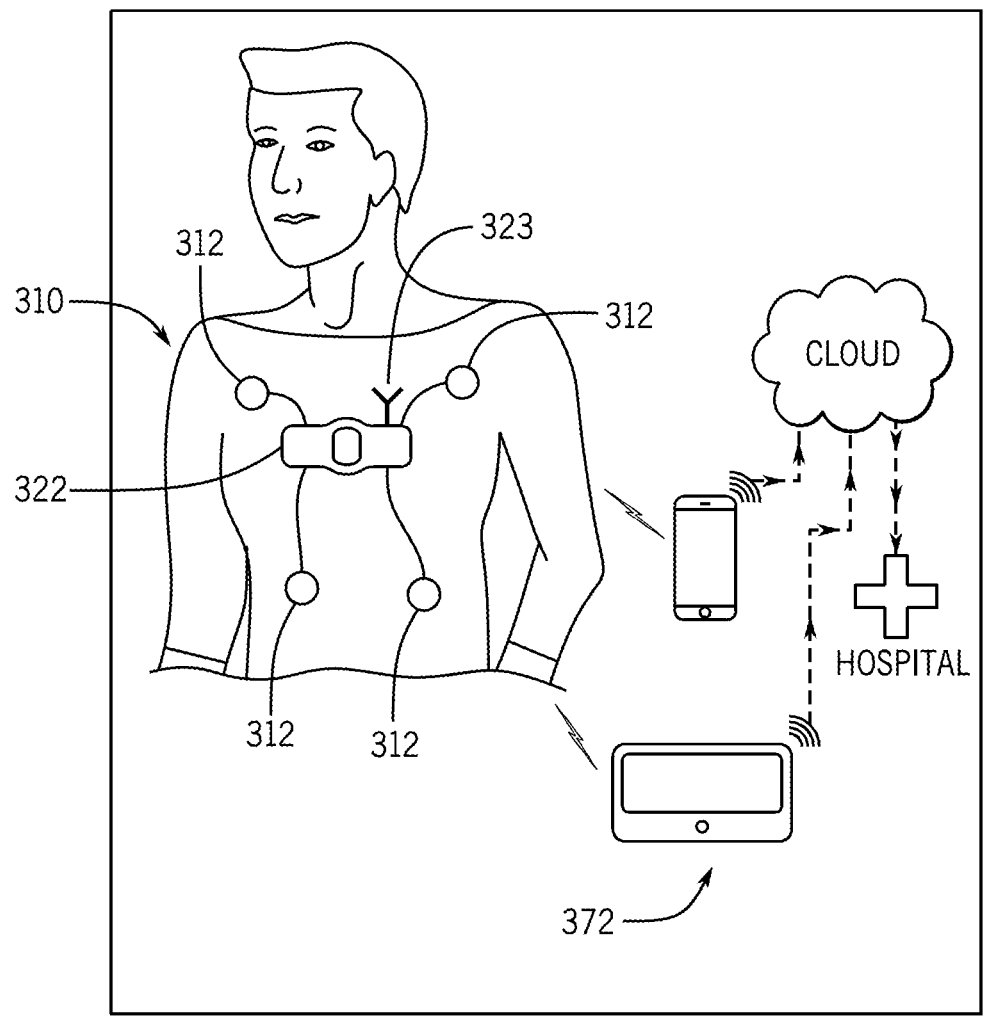
FIG. 35 is an isometric view of a garment according to an exemplary embodiment of the invention.
Figure 36:
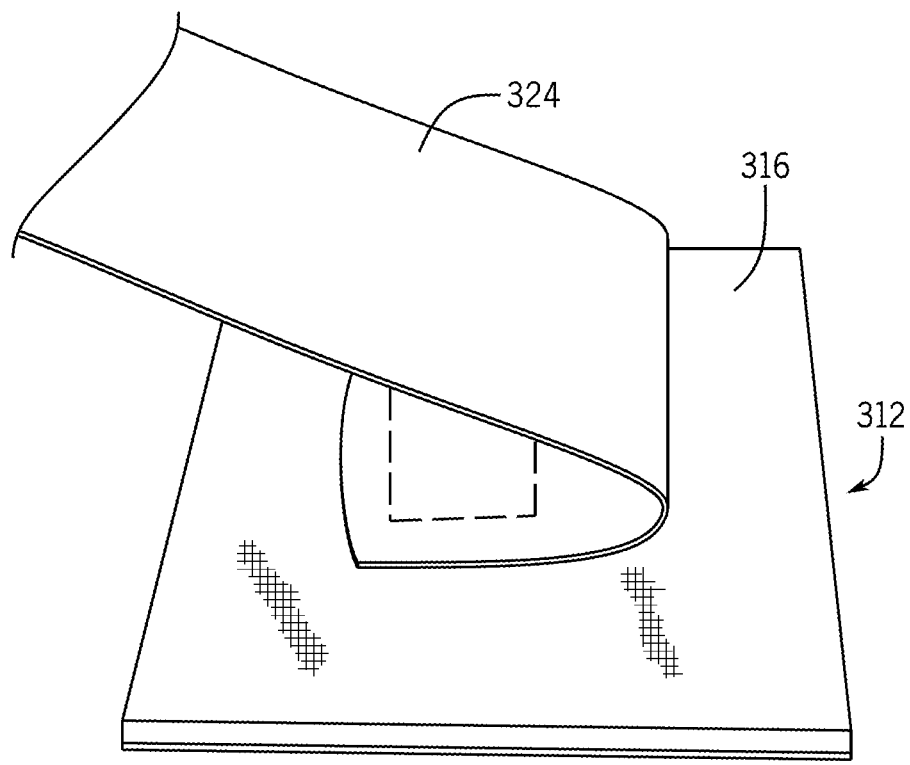
FIG. 36 is a perspective view of a conductive fabric lead secured to a fabric sensor of according to an exemplary embodiment of the invention.

The flow chart in FIG. 23 illustrates the methodology of dynamically co-related 3-lead to 12-lead ECG reconstruction, where the three leads utilized in system 26 can be any suitable leads, such as those leads placed on the extremity of each arm (left and right chest or wrist) and on Chest lead V2, among others. In brief, the ECG signals from the leads 114-118A are filtered using dynamic-correlation filtering method and QRS complements are identified. Further, a training sequence which is based on a sign beat-to-beat analysis creates a patient specific transform from the reduced lead set (Lead I, II, V2—leads 114-118A (FIG. 22)) to the 12 leads to be reconstructed, where the steps of the overall method are illustrated in FIG. 23. Table 1 represents statistics of correlations between actual and reconstructed leads for reconstruction using the reduced lead set in the exemplary embodiment with signals from leads I (114,114A), II (116, 116A), and V2 (118, 118A) and its accuracy compared to existing methodologies.

TABLE 1

Comparison Of Actual and Reconstructed ECG Lead Accuracy

| Matrix | % Accuracy | I | II | III | aVR |
|---|---|---|---|---|---|
| Existing Universal transform | μ | 89.7 | 95.7 | 82.7 | 90.4 |
| DCLT (Dynamic Co-relation based Linear Transforrm | μ | 96.3 | 98 | 96.4 | 97.1 |
| DCICA (Dynamic Co-relation based Independent Component Analysis) | μ | 96 | 97.4 | 95.4 | 98.7 |

| Matrix | % Accuracy | aVL | aVF | V1 | V2 |
|---|---|---|---|---|---|
| Existing Universal transform | μ | 77.9 | 93.5 | 89.8 | 36.7 |
| DCLT (Dynamic Co-relation based Linear Transform | μ | 95.1 | 97.5 | 97.2 | 99.8 |
| DCICA (Dynamic Co-relation based Independent Component Analysis) | μ | 94.7 | 96.9 | 96.9 | 95.8 |

| Matrix | % Accuracy | V3 | V4 | V5 | V6 |
|---|---|---|---|---|---|
| Existing Universal transform | μ | 80.6 | 77.8 | 89.8 | 92.4 |
| DCLT (Dynamic Co-relation based Linear Transform | μ | 97.5 | 97.9 | 98.6 | 98.8 |
| DCICA (Dynamic Co-relation based Independent Component Analysis) | μ | 97 | 97.3 | 97.8 | 98.2 |

More specifically, in the exemplary embodiment of the method illustrated in FIG. 23, initially in block 400 pre-processing of the ECG signals from the leads 114, 114A, 116, 116A, 118, 118A and combinations thereof is performed by reducing noise within the ECG signals, such as according to the process identified previously. This step uses advance filtering which removes any DC offset and 50 Hz/60 Hz line noise. Its combination cascade filters combined with noise reduction methodology described previously and illustrated in the exemplary embodiments of FIGS. 16-22. Specific frequencies for the filtering are selected to comply with American Heart Association (AHA) standards.

The next step in block 402 is to perform detection of the QRS complex within the ECG signals over a number of heartbeats obtained from the leads 114-118A. In this step, a moving average window is utilized to detect the QRS complex. Following this, in block 404 the system produces normalized segments of the ECG signals over multiple heartbeats which are subsequently utilized in block 406 to perform a training or personalized transformation for the particular ECG signal from the patient or individual. In the training transformation, a linear transformation is applied to the normalized ECG signal segment in block 408 and a fast independent component analysis (ICA) is performed on the normalized ECG signal segments in block 410 to reconstruct the signals from missing leads. This training sequence of the training transformation 406 is applied on beat-by-beat basis to the normalized ECG signal segments produced in step 404. The 3 ECG/reduced lead set I (114,114A), II (116, 116A), and V2 (118, 118A) used for the training transform step 406 is also used for the reconstruction of the missing leads in block 412 to generate the reconstructed leads in block 414. In the reconstruction step 412, the independent components (ICs) are generated from the reduced lead set I (114,114A), II (116,116A), and V2 (118, 118A) with an initial guess of mixing matrix formed using and/or of the observations from the reduced lead set, and the set of ICs generated from the reduced lead set using ICA which was generated during the training transform sequence. This helps the algorithms in the training transform sequence to converge to more consistent ordering and orientation of ICs. The adaptability of the transforms in steps 408 and 410 stems from the fact that although the patient specific reconstruction matrix does not change after training, the matrix obtained by the ICA algorithm in step 410 per detected beat does vary. The result is that changes in and/or across detected beats compensate for changes in the reduced lead set observations due to variability in signal propagation conditions.

FIGS. 24A-34D illustrate the nature of the reconstructed signals obtained using the system and method as disclosed in FIG. 23.

Separate from the different methods and accompanying structures for the operation of the system 10, another aspect of the system 10 of the invention is the ability to transmit data between the network 12 and a cloud infrastructure 58, making the recorded healthcare data accessible globally, which can provide the capability to the system 10 for instantaneous review of remote coaches and medical personnel. The integration of the cloud network with the system 10 would not only enhance the data analytics capabilities of the system 10 but also generate a data set of interrelated case studies and/or medical records for the individual being monitored which would be very helpful for advancement of medical science. Another major advantage of our services will be integration of our cloud services with Further these augmented health records for the individual will allow doctors to access patient histories that include a well maintained and detailed patient profile about what is normal physical parameters for the individual are based upon the recorded and stored data.

Figure 8:
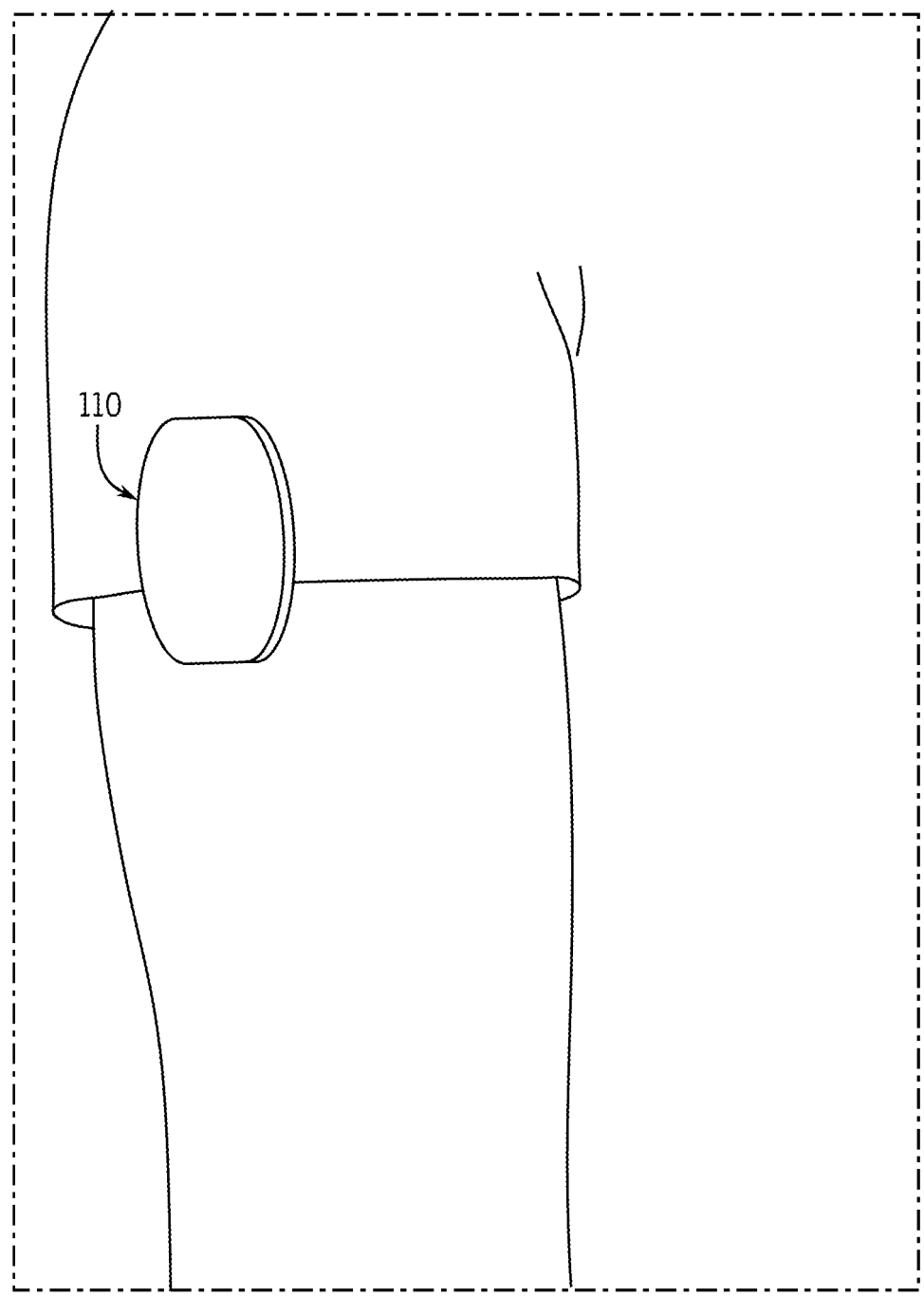
FIG. 8 is a schematic view of a sensor according to an exemplary embodiment of the invention.
Figure 9:
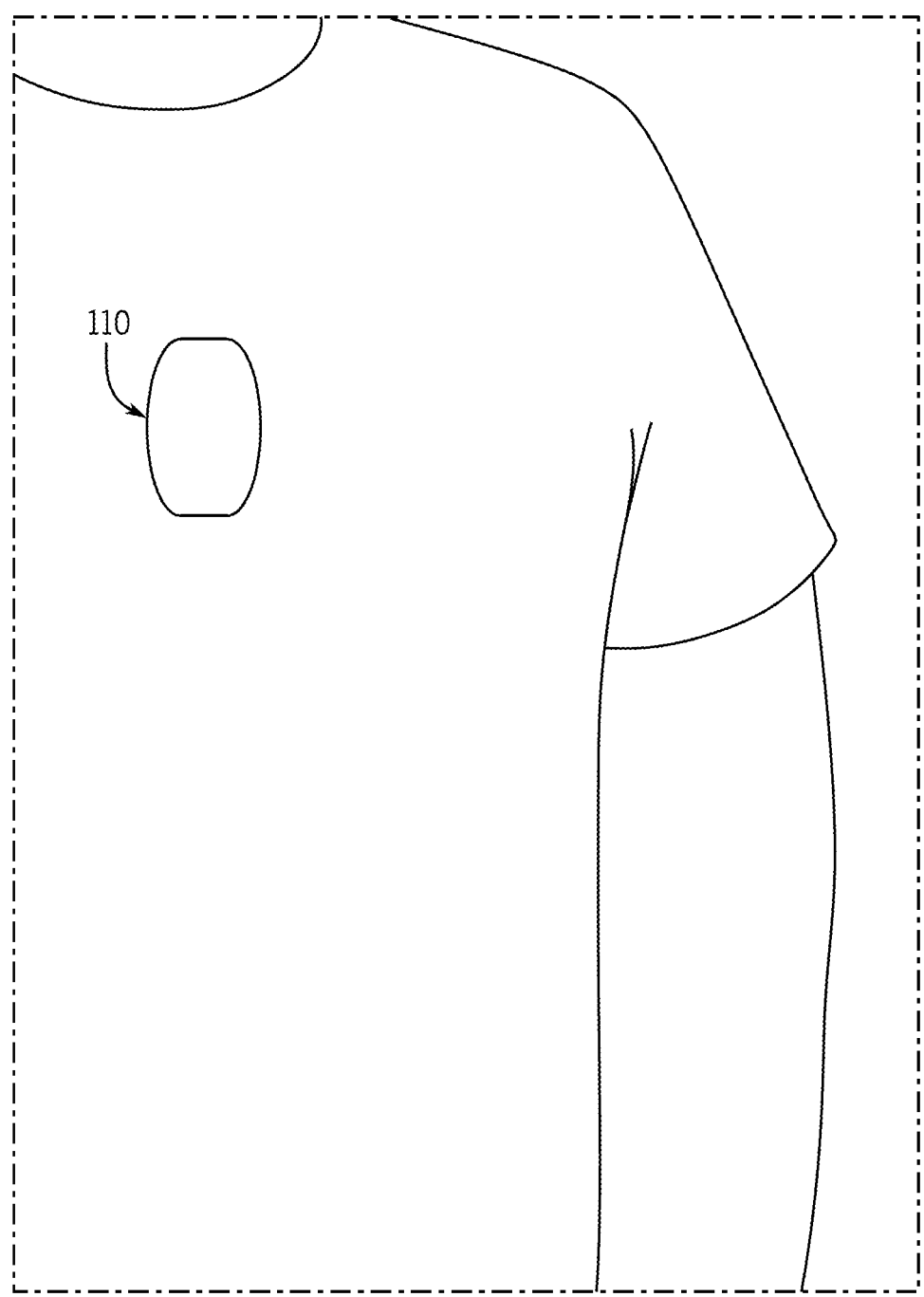
FIG. 9 is a schematic view of a sensor according to another exemplary embodiment of the invention.

Looking now at FIGS. 8 and 9, in another exemplary embodiment of the invention, with particular regard to the blood pressure sensor 32, the sensor 32 can be a photoplethysmography (PPG) sensor capable of using a non-invasive, light-based technology for measuring the rate of blood flow through the skin in order to determine the heart rate of the individual. A portion of the body of the individual can be pressed against the sensor 32 (against skin or through clothing disposed over the skin) and measurements of the heart rate, blood oxygen saturation and blood pressure can be measured. This data can be stored directly within the sensor 32, which can optionally contain a power source 112 and an electronic storage medium 114 in addition to any microcontroller 116 and transceiver 118 present within the sensor 32, similarly to alternative embodiments of the other sensors 20-30 and 34, or when the sensor 32 is formed as a data aggregator 504 (FIGS. 45 and 46) and/or can transmit the sensed data to a central hub 18, cloud network 58 or other network 64. The data obtained by the sensor 32 can be transit time co-related to data obtained by the ECG sensor(s) 30 also associated and/or contained within the system 10, to provide enhanced data on the heart rate, blood oxygen saturation and blood pressure of the individual. Further, sensors 30 and 32 can be combined into a single sensor 110 including the necessary sealed housing and components to obtain measurements utilizing both ECG and PPG to provide separate or combined signals that are stored within the sensor 110 and/or transmitted to a central hub 18, cloud network 58 or other network 64, such as by the use of a smart IoT gateway/device/bridge 15,18 (FIGS. 1, 45, 46) that is not a mobile device, but that operates to effectively connect the hub to a network in order to enable the hub to transmit the data to a remote location from the sensor system. The smart IoT gateway/bridge can be formed integrally with or separately from the sensor system and is capable of aggregating data from multiple hubs, storing the data, processing the data and/or creating local alerts and communicates with our medical device/hub over Bluetooth® protocols, such as a Bluetooth® Low Energy (BLE) protocol, and push the data received over Wi-Fi using an Internet of Things (IoT) network protocols, for example. In one embodiment, the smart IoT gateway/bridge includes BLE and Wi-Fi chips which communicate with each other of protocol stack level to establish communication between two different communication protocols, i.e., BLE and Wi-FI. Data from or to the sensor system is pushed over/through/into a cloud network here it is captured and processed by a suitable software system. The sensor 110 can be utilized within the system 10 or by itself to provide the desired parameter data on the individual, as an alternative to current blood pressure measurement devices that include cuffs positioned around the limb of the individual.

Figure 10:
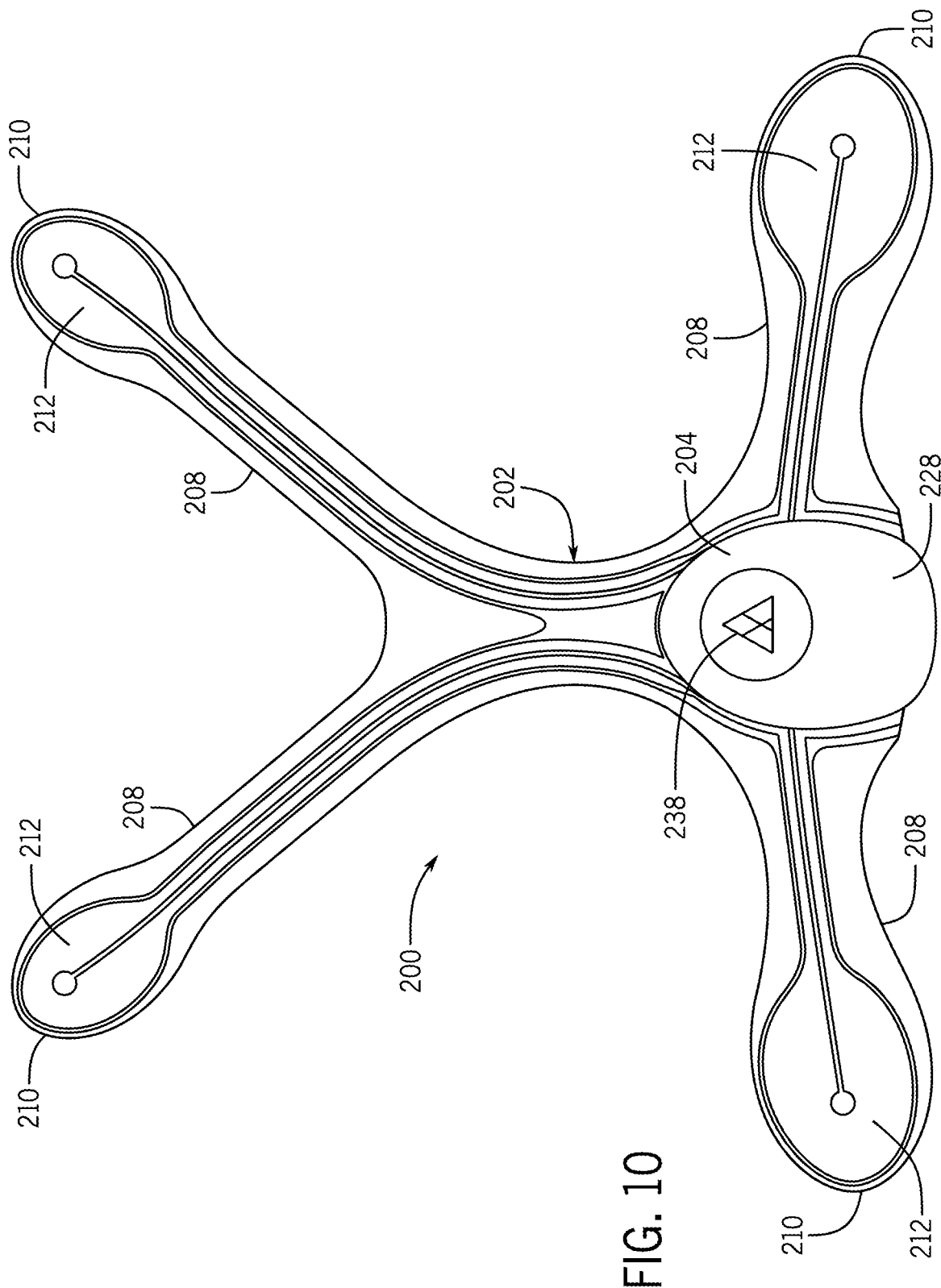
FIG. 10 is an isometric view of a body sensor system according to another exemplary embodiment of the invention.
Figure 15:
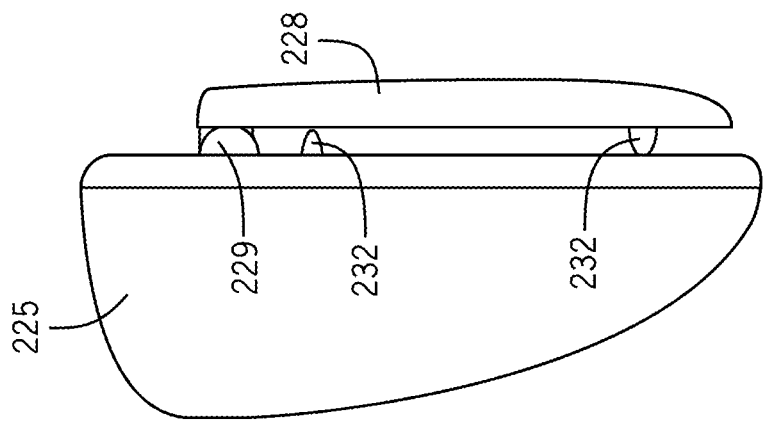
FIG. 15 is a side elevation view of the sensor module of FIG. 12.
Figure 14:
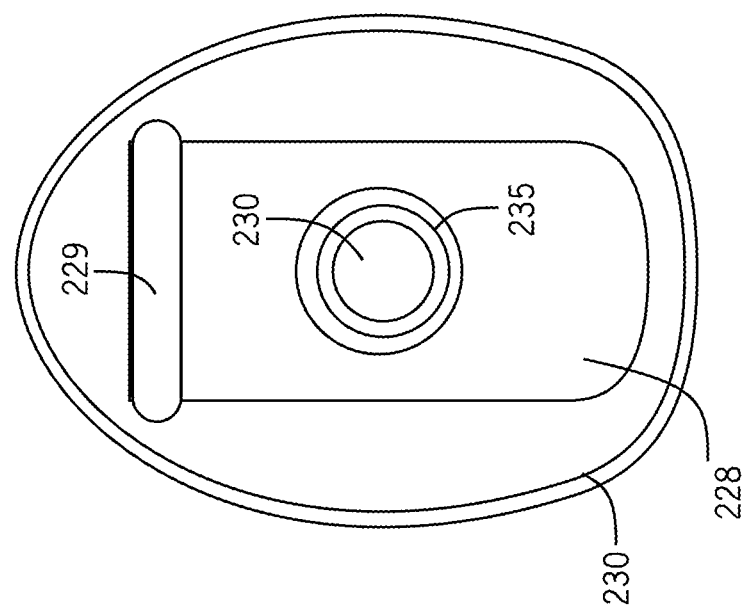
FIG. 14 is a bottom plan view of the sensor module of FIG. 12.
Figure 13:
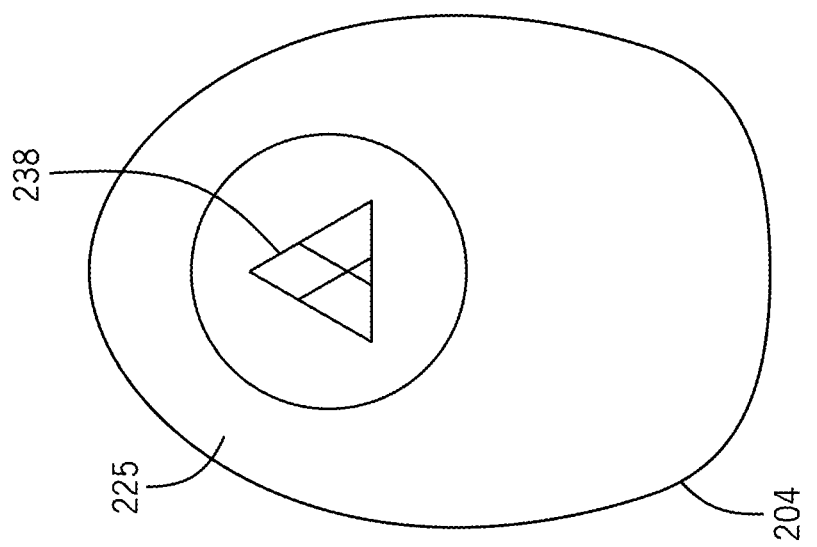
FIG. 13 is a top plan view of the sensor module of FIG. 12.

Looking now at FIGS. 10-12, another exemplary embodiment of a body sensor system 200 is illustrated. The system 200 includes a patch 202 to which is releasably secured a hub/sensor module 204.

As best shown in FIGS. 10 and 11, the patch 202 includes a central portion 206 from which extend a number of arms 208. The arms 208 are disposed relative to the central portion 206 in a manner that position the distal ends 210 of each arm 208 at a location relative to the body of an individual wearing the patch 202 that enables sensors 212 disposed in each distal end 210 to obtain signals capable of being utilized as ECG signals for the individual. The sensors 212 are constructed in a known manner and can be positioned within the distal ends 210 of the arms 208 in any suitable manner, such as by being affixed to or molded within a suitable material forming the patch 202. The sensors 212 are interconnected with a conductive contact 214 disposed at the central portion 206 of the patch 202 by a conductive member 216. The conductive member 216 can be any suitable conductive member, such as a wire embedded within the material forming the patch 202, or by a conductive material that is printed or otherwise applied to the structure of the arms 208 between the sensor 212 and conductive contact 214.

The patch 202 also includes a module cradle 218 formed within the central portion 206. The cradle conforms to the shape of the module 204 such that the module 204 can be readily secured to the central portion 206 of the patch 202. In the illustrated exemplary embodiment, the cradle 218 is formed as a recess 220 in the central portion 206 and includes a first aperture 222 and a second aperture 224.

Referring now to FIGS. 10 and 12-15, the hub/sensor module 204 includes a housing 226 shaped to conform to the configuration of the cradle 218 and a securing clamp 228 attached to the housing 226 by a hinge 229. The clamp 228 can be pivoted away from the housing 226 to enable the housing 226 to be positioned within the cradle 218 on the patch 202. The housing 226 additionally includes a skin or temperature sensor 230 that extends outwardly from the housing 226 and that is insertable within the first aperture 222 formed in the cradle 218. The skin sensor 230 functions to determine the temperature of the individual and to properly locate the housing 226 with regard to the cradle 218 when attaching the sensor module 204 to the patch 202.

Adjacent the skin sensor 230, the housing 226 also include a number of contact pins 232 that are aligned and positioned in contact with the conductive contacts 214 formed on the patch 202. The engagement of the pins 232 with the contacts 214 enables the signals obtained by the sensors 212 to be sent along the conductive members 216 to the contacts 214 where the signals are obtained or passed into the housing 226 via the pins 232.

Opposite the housing 226, the clamp 228 includes one or more friction teeth 234 that engage the patch 202 through the second aperture 224 when the clamp 228 is urges towards the housing 226 when the housing 226 has been positioned within the cradle 218. The clamp 228 also includes an opening 236 that is positioned in alignment with the skin sensor 230 to enable the skin sensor 230 to pass through the clamp 228 and into contact with the skin of the individual without interference from the clamp 228.

In operation, the patch 202 is positioned on the body of an individual, such as by placing the patch 202 in direct contact with the skin of the individual or by attaching the patch 202 to an article of clothing (not shown) that is worn by the individual. When activated, the light 238 (FIGS. 10 and 13) on the housing 226 opposite the clamp 228 illuminates to indicated the state of operation of the module 204. In this manner the sensors 212 in the patch 202 are located where necessary to obtain the signals from the individual necessary of the ECG and EEG analysis. The sensor module 204 can then be secured to the patch 202 by displacing the clamp 228 from the housing 226, placing the housing 226 within the cradle 218 on the patch 202 and urging the clamp 228 towards the housing 226 to engage the clamp 228 with the patch 202. The signals from the sensor module 204 can be stored within a suitable electronic storage medium until downloaded at a later time, or can be transmitted from the module 204 to another device or system for analysis. Further, in another exemplary embodiment, after use, the hub/sensor module 204 can be detached from the patch 202 for re-attachment to a separate patch 202 for further analysis of the individual, while the prior used patch 202 can be discarded.

In certain exemplary embodiments, the invention is comprised of a sensor pad with multiple sensor regions, a conductive element that traverses the sensor pad and delivers all signals to at least one sensor area, a modular sensor hub, and a mechanical feature that helps secure the sensor hub attach to the sensor pad. This feature may include raised contours and a hole to help it lock into place.

In an exemplary embodiment, the sensor hub has a protrusion that passes through a hole of the sensor pad and rotates to a locking closed position, thereby securing it to the pad and also forcing a mechanical contact with electrically conductive elements on or in the sensor pad that carry signal data from the sensing regions of the pad and into the sensor hub. The sensor hub then broadcasts data wirelessly.

In an exemplary embodiment, the data is sent to a wireless device like a smart phone which can give live feedback to the user and/or send data to a cloud-type data service.

In various exemplary embodiments, the invention includes:

a. 1. Body-mounted sensor pad with multiple sensing regions
b. 2. Sensor pad of #1 which is monolithic and joins together several sensing pad locations to eliminate installation errors
c. 3. Sensor pad of #2 which is made from one substrate material
d. 4. Sensor pad of #3 whereby sensing elements share at least one surface
e. 5. Sensor pad of #3 whereby sensing elements share multiple materials that are joined together.
f. 6. Sensor pad of #1 which is sized for different individuals
g. 7. Sensor pad of #1 whereby electric signal from body is carried on or in sensor pad
h. 8. Sensor pad of #7 whereby electric signal is carried by wire mounted to pad
i. 9. Sensor pad of #7 whereby electric signal is screen printed or similarly attached to the surface of the sensor pad
j. 10. Sensor pad of #1 which is configured to receive a sensor hub and conduct an electronic signal to it.
k. 11. Sensor Pad and hub of #10 that includes a nesting area to secure sensor hub
l. 12. Sensor pad and hub of #10 that includes a hole to secure sensor hub
m. 13. Sensor pad and hub of #10 which includes a one time use connection system with a contact area of the pad that conducts electric signals to the hub by means of a pressure or puncturing connection
n. 14. Sensor pad and hub of #10 that includes a multiple use connection system that includes a reusable connector
o. 15. Sensor hub and pad of #10 with locking clip
p. 16. Sensor hub of #15 whereby locking clip has a hole for pass through of wireless sensing signals
q. 17. Sensor hub and pad of #14 whereby locking clip is articulated from one or more ends
r. 18. Sensor hub and pad of #16 with articulating arm that goes through hole in pad to secure it to the sensor pad in at least one location
s. 19. Sensor hub and pad of #17 with a the signal connection area located proximate the locking hole area
t. 20. The sensor hub of #16 where the sensor pad also has a hole to allow a sensor mounted to the hub to read data through the sensor pad and into the body directly.
u. 21. Garment with body sensors built in
v. 22. Sensor garment of #21 which is monolithic and joins together several sensing pad locations to eliminate installation errors
w. 23. Sensor garment of #22 which is made from one substrate material
x. 24. Sensor garment of #23 whereby sensing elements share at least one surface
y. 25. Sensor garment of #23 whereby sensing elements share multiple materials that are joined together.
z. 26. Sensor garment of #21 which is sized for different individuals
aa. 27. Sensor garment of #21 whereby electric signal from body is carried on or in sensor pad
bb. 28. Sensor garment of #27 whereby electric signal is carried by wire mounted to pad
cc. 29. Sensor garment of #27 whereby electric signal is screen printed or similarly attached to the surface of the sensor pad
dd. 30. Sensor garment of #21 which is configured to receive a sensor hub and conduct an electronic signal to it.
ee. 31. Sensor garment and hub of #30 that includes a nesting area to secure sensor hub
ff. 32. Sensor garment and hub of #30 that includes a hole to secure sensor hub
gg. 33. Sensor garment and hub of #30 which includes a one time use connection system with a contact area of the garment that conducts electric signals to the hub by means of a pressure or puncturing connection
hh. 34. Sensor garment and hub of #30 that includes a multiple use connection system that includes a reusable connector
ii. 35. Sensor garment and pad of #30 with locking clip
jj. 36. Sensor garment of #35 whereby locking clip has a hole for pass through of wireless sensing signals.
kk. 37. Sensor garment and pad of #34 whereby locking clip is articulated from one or more ends
ll. 38. Sensor garment and pad of #36 with articulating arm that goes through hole in pad to secure it to the sensor garment in at least one location
mm. 39. Sensor garment and pad of #37 with a the signal connection area located proximate the locking hole area
nn. 40. The sensor garment of #36 where the sensor garment also has a hole to allow a sensor mounted to the garment to read data through the sensor garment and into the body directly.

Referring now to FIGS. 35-44, one exemplary and non-limiting embodiment of a garment of the invention is illustrated at 310. The garment 310 can have any shape and can be employed to be worn on the upper body of an individual, on a lower body of the individual, on one or more extremities, e.g., arm and/or legs of the individual, on the head of the individual or on any other suitable body part or combination of body parts as desired.

Figure 44:
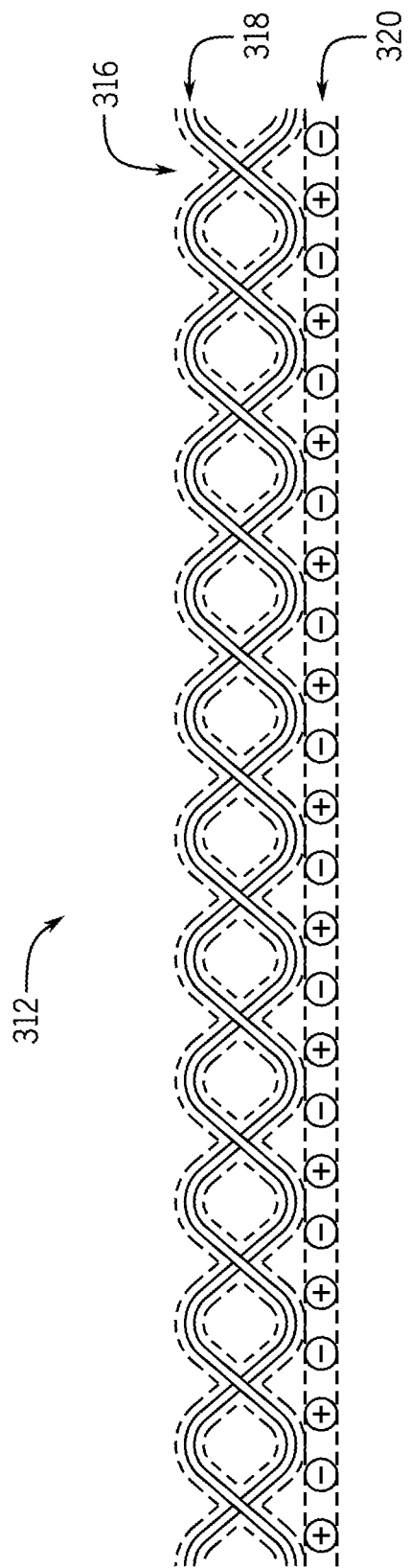
FIG. 44 is a cross-sectional view of the fabric sensor according to an exemplary embodiment of the invention.

In one exemplary embodiment, the garment 310 is formed of with one or more fabric sensors 312 shown in FIG. 44 as having a cloth or film layer 314 on which a conductive coating 316 is placed. The sensor 312 can optionally be formed with the conductive layer or coating 316 covered by a suitable conductive adhesive (not shown) and a release liner (not shown) in order to securely hold the conductive layer 316 in electrical contact with the body of the individual. In other exemplary embodiments, the adhesive layer and the release liner can be omitted, with the form of the garment 310 providing sufficient conformance and contact with the body of the individual. Examples of the fabrics 312 that can be used to form the garment 310 are those disclosed in U.S. Pat. Nos. 7,651,638; 7,713,447; 7,867,611; 7,998,574; 8,673,184; 8,788,009; and 8,792,957, each of which are expressly incorporated herein by reference for all purposes. As shown in FIG. 44, the fabric sensor 312 can include the coating 316 positioned on a woven conductive fabric 318 having an ionic interface 320 disposed on one surface of the fabric 318.

The garment 310 receives the physiological signals from the body of the individual and can transmit them along the conductive layer 316 to a suitable monitoring system 10. The system 10 can be disposed on the garment 310 or can be separate from the garment 310. In the exemplary embodiment where the system 10 is remote from the garment 310, the garment 310 can include a suitable transceiver 323 that is operably connected to the conducive layer 316 in order to transmit the signals from the garment to the system 10.

In either exemplary embodiment, the system 10 can be any suitable monitoring device 22, such as that described previously or disclosed in co-owned and co-pending U.S. Non-Provisional patent application Ser. No. 15/207,503, which is expressly incorporated by reference herein for all purposes. The signals transmitted to the system 10 from the garment 310 can be utilized to monitor the current medical status of the individual for medical review, performance review, such as for improvement of athletic performance, or any other suitable purpose.

The nature of the garment 310 is such that the conductive layer 316 is maintained in close conformance with the body of the individual to create good contact between the garment 310 and the individual. In this manner, the garment 310 can obtain and transmit the necessary signals for monitoring the individual using only the garment 310 and without the need for any bulky or extraneous monitoring device to be worn by the individual. The garment 310 can be form-fitting so as not to restrict the movement of the individual and can be formed into any suitable part of a uniform, such as to enable the monitoring of an athlete performing in a sporting event.

Figure 37:
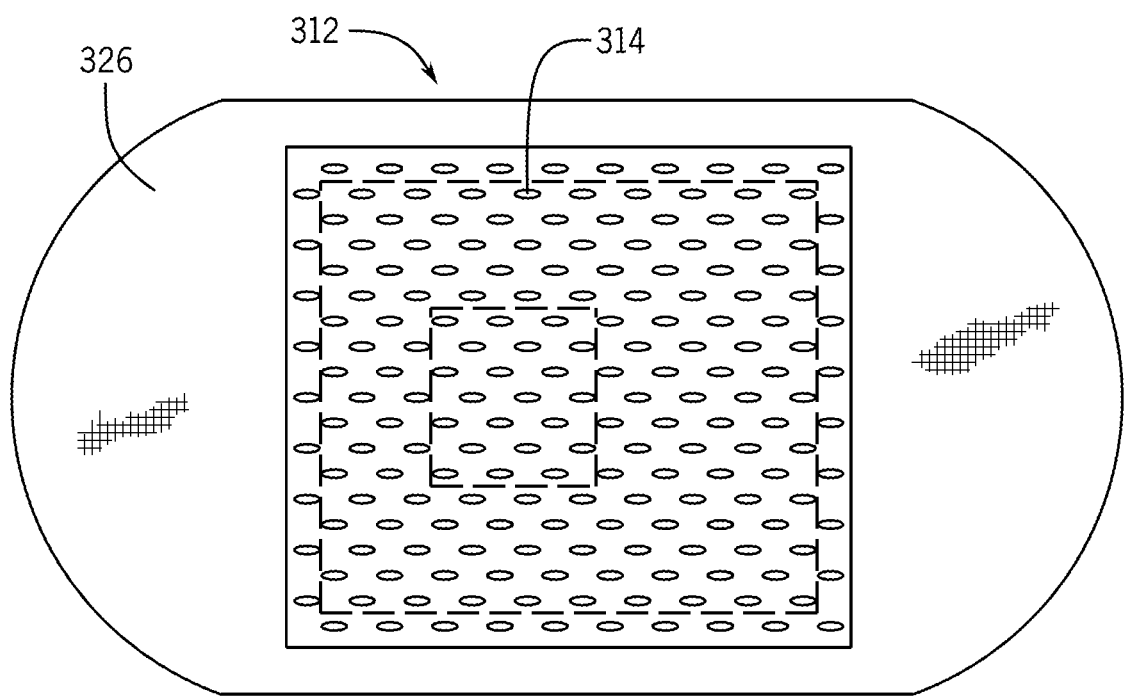
FIG. 37 is a perspective view of the fabric sensor secured to a fabric backing according to an exemplary embodiment of the invention.
Figure 38:
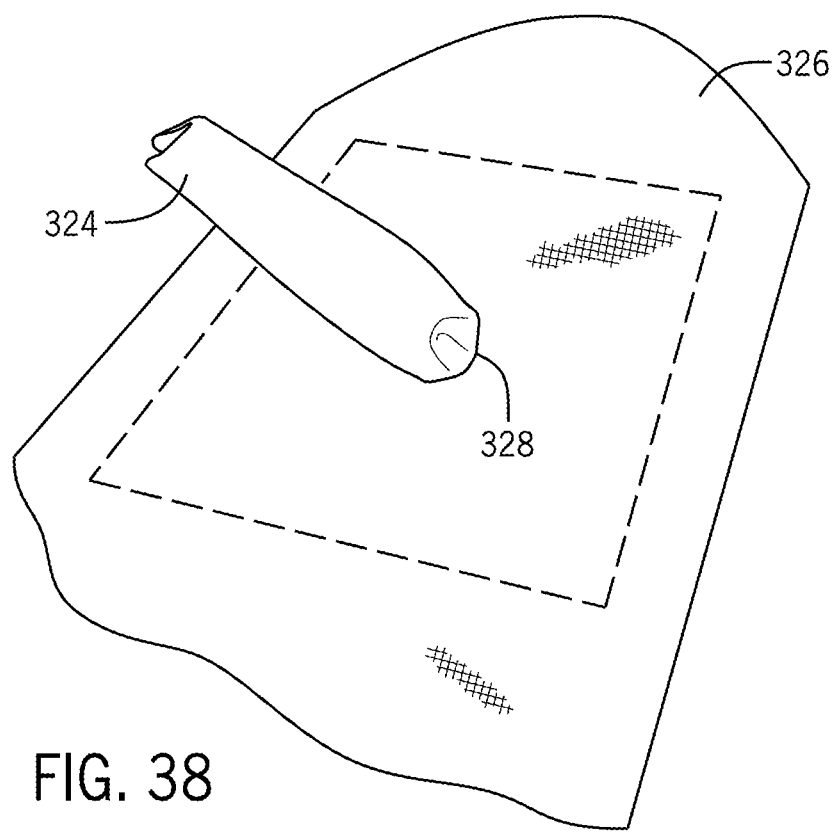
FIG. 38 is a perspective view of the fabric sensor including a connection sleeve extending through the fabric backing of FIG. 37 according to an exemplary embodiment of the invention.
Figure 39:
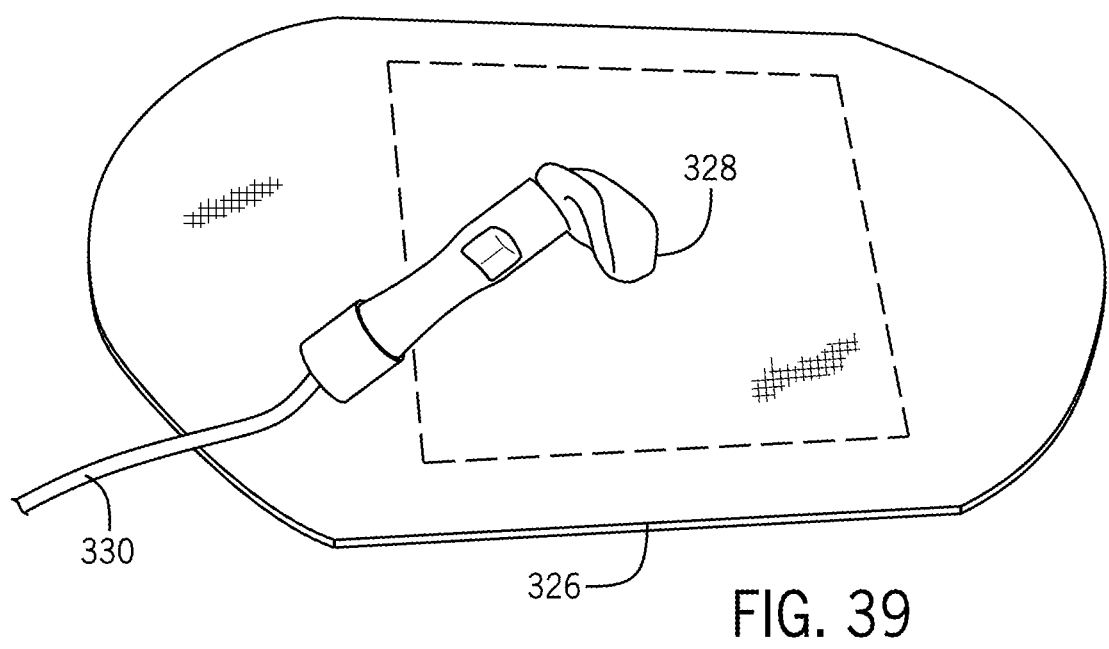
FIG. 39 is a perspective view of a fabric sensor wire lead extending through the fabric backing of FIG. 37 according to an exemplary embodiment of the invention.

With reference now to FIGS. 37-38, in one exemplary embodiment of the invention, the conductive layer 316 of the fabric sensor 312 can be connected to the system 10 via a strip of conductive fabric 324. The conductive fabric 324 is attached to the sensor 312 in any conventional manner such as by an adhesive or stitching, and can be secured to the garment 310 at the conductive fabric 324 extends between the sensor 312 and the system 10. The conductive fabric can be secured directly to the sensor 312, as shown in FIG. 37, or can be attached to one side of a fabric backing member 326, that can be formed of any suitable fabric material, with the fabric sensor 312 attached opposite the conductive fabric 324. The backing member 326 provides a separate base for the attachment of the sensor 312, which can then separately be attached to the garment 310, as opposed to directly securing the sensor 312 to the garment 310. To engage the sensor 312 with the conductive fabric 324, as shown in FIG. 39, the conductive fabric 324 or the material forming the sensor 312 can extend through a suitable opening 328 in the backing member 326.

Figure 40:
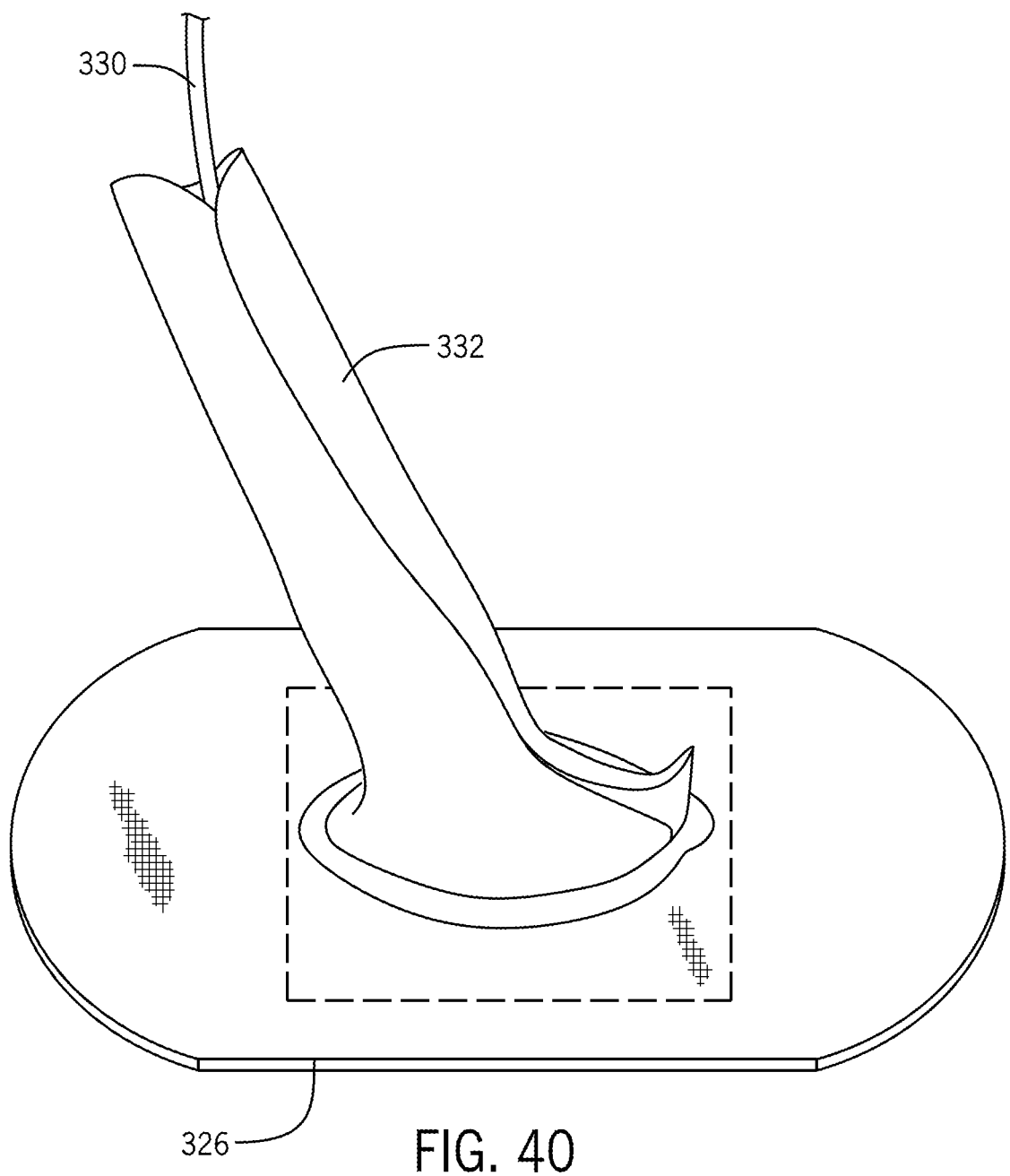
FIG. 40 is a perspective view of insulation disposed around the wire lead of FIG. 39 according to an exemplary embodiment of the invention.
Figure 41:
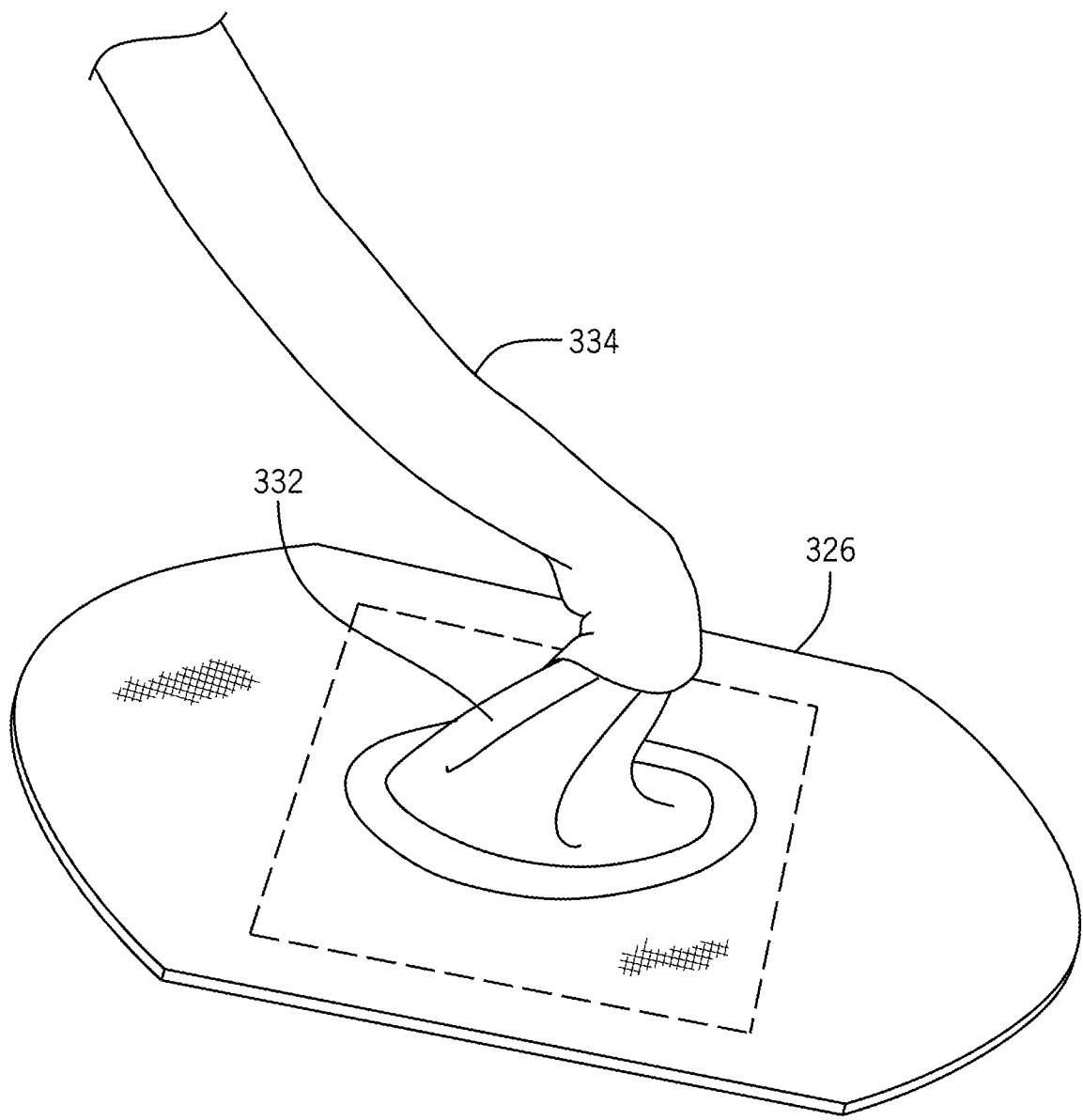
FIG. 41 is a perspective view of a non-conductive shield disposed around the wire lead of FIG. 39 according to an exemplary embodiment of the invention.
Figure 42:
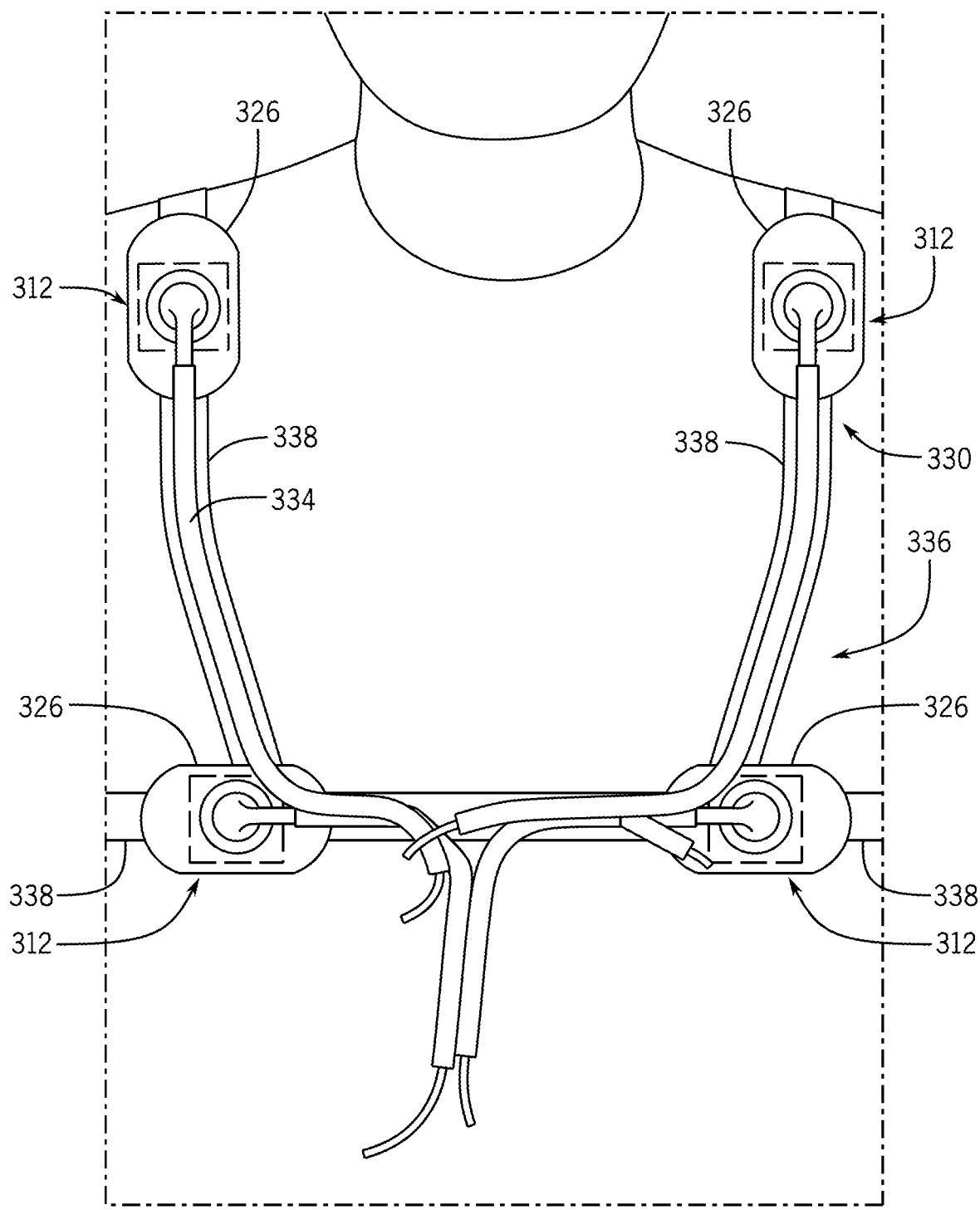
FIG. 42 is a partially broken away view of a sensor harness incorporated within the garment of FIG. 35 according to an exemplary embodiment of the invention.

Looking now at FIGS. 40-42, in another exemplary and non-limiting embodiment, the sensor 312 can be connected to the wire lead 330 that extends through the opening 328. The lead 330 can be formed in a conventional manner and can be engaged with the garment 310 in a suitable manner to extend from the sensor 312 to the system 10. To protect the signals transmitted along the wire lead 330, the lead 330 can include an insulating member 332 wrapped around the lead 330 adjacent the backing member 326, and/or an shielding member 334 disposed on the backing member 326 and extending around the insulating member 332 as it extends away from the backing member 326.

Figure 43:
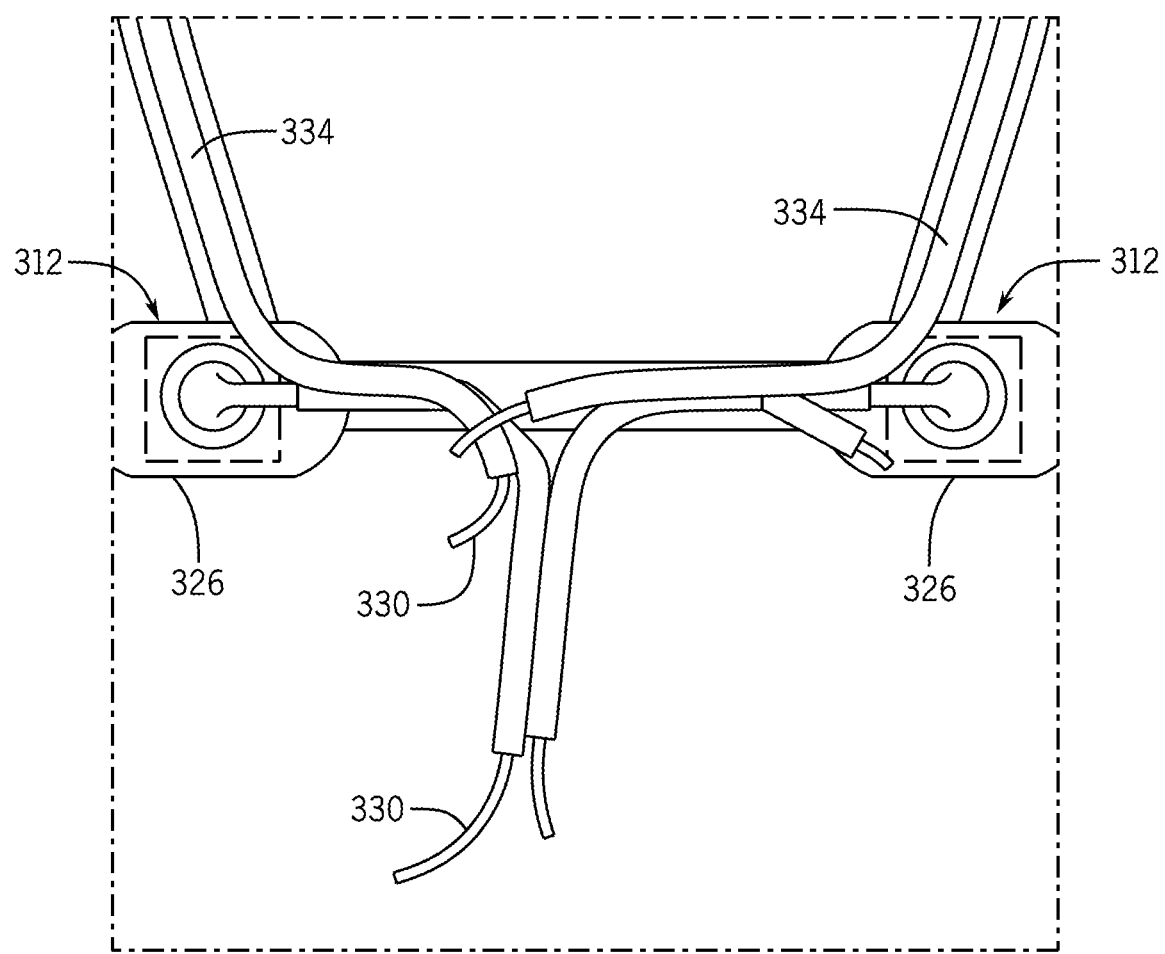
FIG. 43 is a partially broken away view of the wire leads of the sensor harness of FIG. 42 according to an exemplary embodiment of the invention.

Referring now to FIGS. 43 and 44, while the sensors 312 can be integrated directly into or secured directly to the garment 310 in positions where the sensors 312 are positioned in contact with the body of the individual to obtain the physiological signals, the sensors 312 can additionally be utilized with the backing members 326 to form a sensor harness 336, such as described previously. In other exemplary embodiments, the harness 336 includes a number of connecting straps 338 that are formed to extend around the appropriate body portion of the individual. Each strap 338 includes one or more backing members 26 attached thereto, with a sensor 312 secured to the backing member 326, thereby positioning the sensors 312 in the desired locations on the harness 338. The leads 330 extending from the sensors 312 can be routed along the straps 338 and combined at a common location where the leads 330 can be connected directly or indirectly to the system 10. The harness 338 can be incorporated within the structure of the garment 310 to provide a ready-made positioning arrangement for the sensors 312 within the garment 310 that does not affect the ability of the garment 310 to fit the individual and compress the sensors 312 into suitable connection with the body of the individual.

Figure 45A:
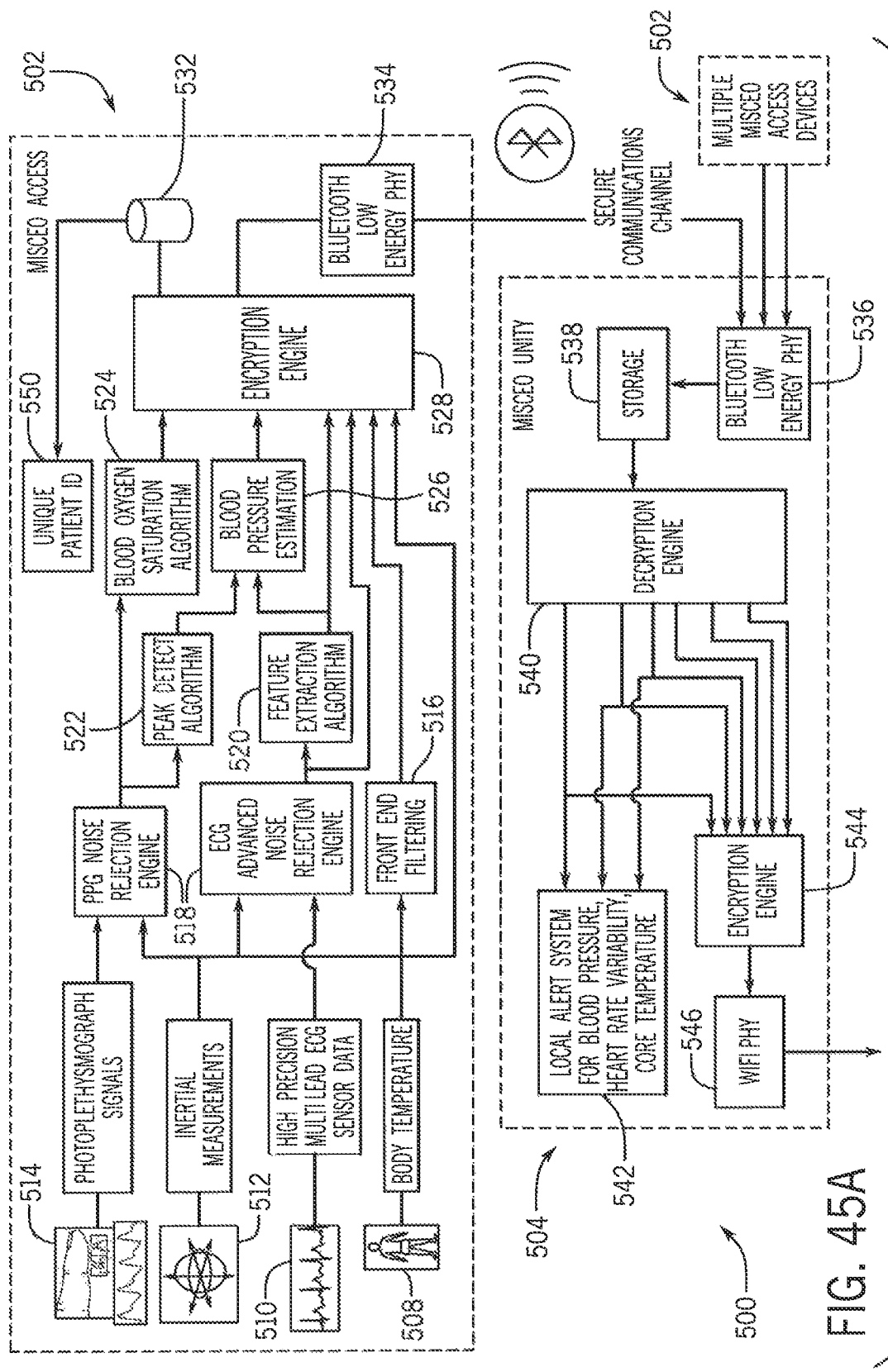
FIG. 45A is a schematic view of one portion of the monitoring system according to another exemplary embodiment of the invention.
Figure 45B:
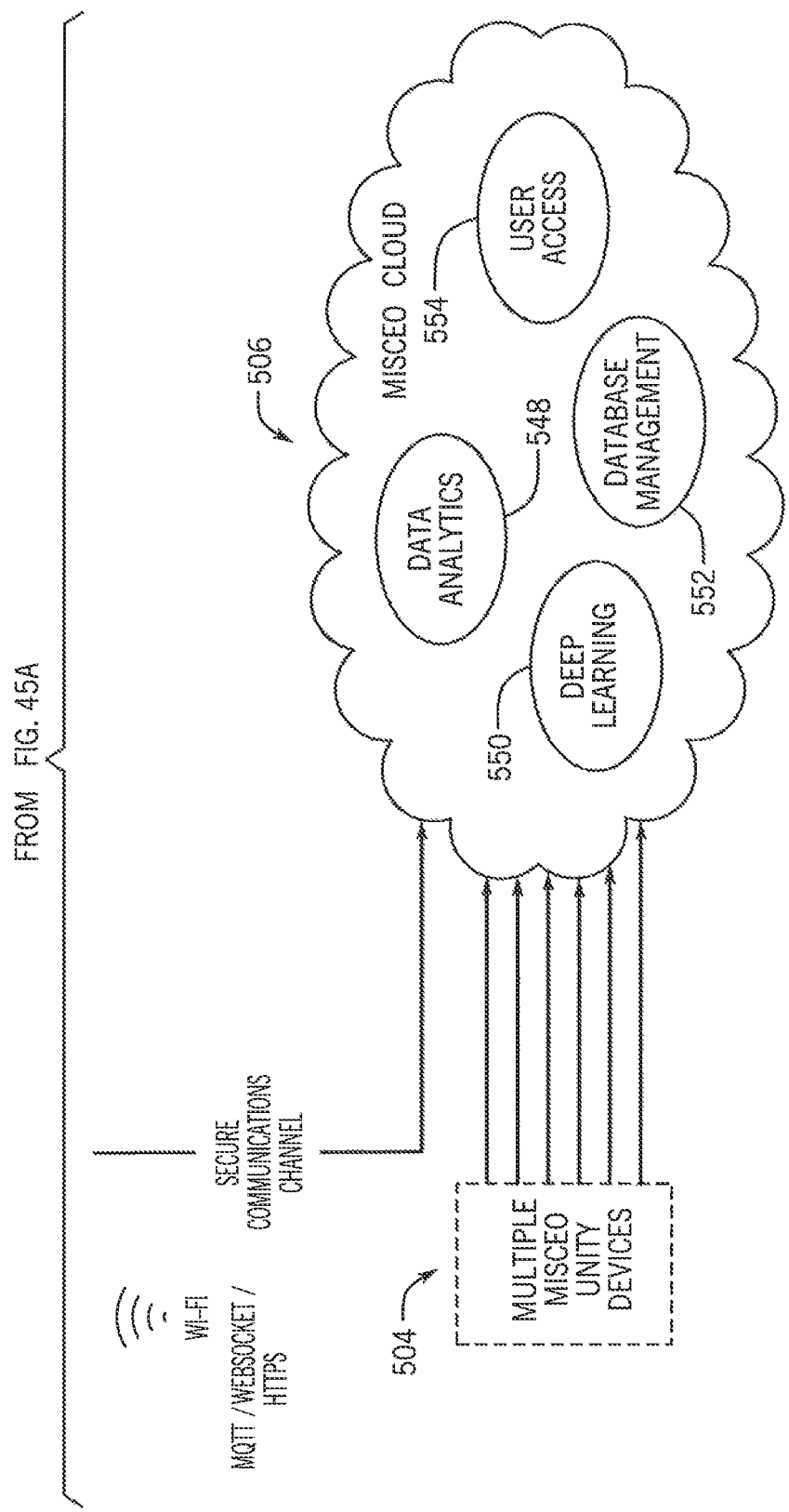
FIG. 45B is a schematic view of a second portion of the monitoring system according to another exemplary embodiment of the invention.

Referring now to FIGS. 45A-45B, in another exemplary embodiment the sensor/monitoring system 500 includes a hardware device 502, a smart IoT gateway/device/data aggregator 504 and a cloud computing platform 506. The hardware device 502 includes multiple sensors 508-514 with data signals from each sensor 508-514 processed using one or more filters 516, one or more noise reduction engines 518, feature extraction algorithms 520, peak detection algorithms 522, saturation algorithms 524, parameter estimators 526, and pattern recognition algorithms, systems or techniques to give desirable results for the various physiological parameters sensed by the sensors 508-514, which can include but are not limited to, six (6) lead ECG, blood oxygen saturation, body temperature, blood pressure and body posture. The data signals from the sensors 508-514 and passed through one or more of the other components 516-526 can be encrypted by an encryption engine 528 in conjunction with a unique patient or individual ID 530, which can be stored in a database 532 along with the encrypted data signals.

Figure 46:
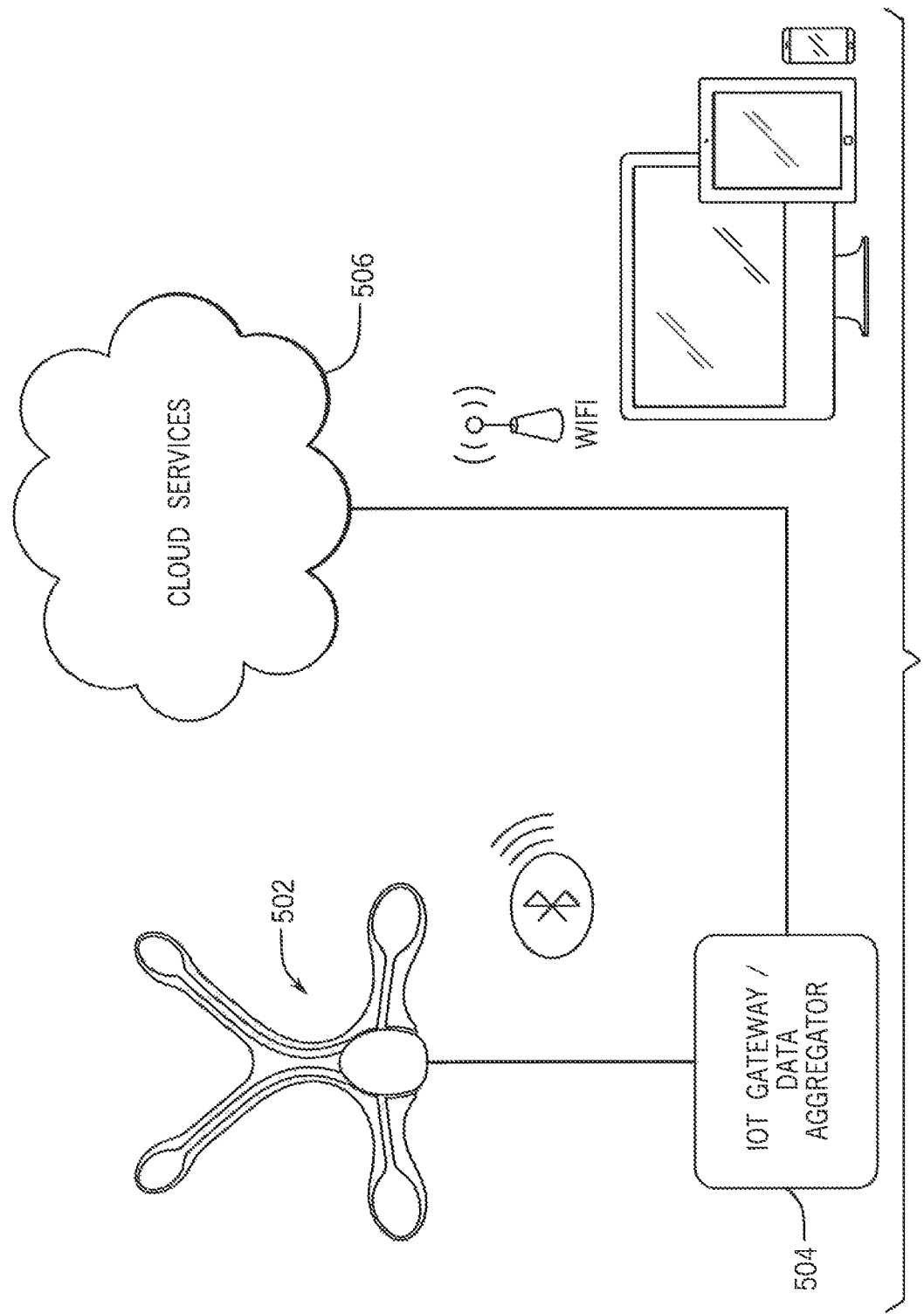
FIG. 46 is a schematic view of the monitoring system according to another exemplary embodiment of the invention.

The encrypted signals and ID can be transmitted from the hardware device 502 over Bluetooth® low energy transceiver 534 to the data aggregator/smart IoT gateway 504, which in an exemplary embodiment is a smart BLE-Wi-Fi bridge, including a transceiver 536 and associated electronic storage media 538. The aggregator 504 also includes a decryption engine 540 capable of decrypting/encrypting the data signals optionally with the ID 530 to facilitate identification of the data signals and device 502, and processing them in a microcontroller 542, such as to analyze the data signals in various manners, such as those described previously, and to create or receive local alerts based on the data signals and analysis thereof. The data signals can be re-encrypted in an encryption engine 544 and sent to the cloud computing platform 506 via a transceiver 546, such as by using IoT protocols over TCP/IP or UDP network. The data aggregator 504 is capable of handling data signals from multiple devices 502 and multiple data aggregators 504 can transmit signal data from multiple device 502 to the cloud computing platform 506 where data is analyzed. In the cloud platform 506, various process are performed to analyze the signal data associated with the unique ID 530 and each device 502 in order to provide insight into the data, including but not limited to advanced data analytics 548, machine learning and/or deep learning 550, database management 552, and user access control listings 554. The data and various analytical results are visualized and presented over cloud platform, with the analytical data represented using web applications which can be accessed using PC, mobile phone or devices and/or tablet devices 560, as shown in FIG. 46.

REFERENCES

The following references are expressly incorporated herein by reference in there entireties for all purposes:
[1] Dawson D et al. Linear Affine Transformations Between 3-lead (Frank XYZ leads) Vectorcardiogram and 12-lead Electrocardiogram Signals. Journal of Electrocardiology, 42: 622-630, 2009.
[2] Gregg R E et al. Limitations on the Re-Use of Patient Specific Coefficients for 12-lead ECG Reconstruction. Computers in Cardiology, 35: 209-212, 2008.
[3] Dower G E, Machado H B, Osborne J A. On Deriving the Electrocardiogram from Vectorcardiographic Leads. Clin Cardiology, 3: 87-95, 1980.
[4] Schijvenaars R J A. Intra-individual Variability of the Electrocardiogram. Ph.D. Thesis: Erasmus University Rotterdam, 2000.
[5] James C J and Hesse C W, Independent Component Analysis for Biomedical Signals. Physiological Measurement, 26: R15-R39, 2005.
[7] Hyvärinen A and Oja E. Independent Component Analysis: Algorithms and Applications. Neural Networks, 13(4-5):411-430, 2000.
[8] He T, Clifford G, and Tarassenko L. Application of independent component analysis in removing artefacts from the electrocardiogram. Neural Comput. And Applic, 15: 105-116, 2006.
[9] Jung T P et al. Independent Component Analysis of Biomedical Signals. Proceedings of $2^{nd}$ International Workshop on ICA and BSS: 633-644, 2000.
[10] de Charzal P and Celler B G. A Critical Review of the Synthesis of the Orthogonal Frank Lead ECGs from 12 Lead Recordings. Proceedings of 16th Annual International Conf of the IEEE Engineering Advances: New Opportunities for Biomedical Engineers: 958-959, 1994.
[11] Man S et al. Individually Improved VCG Synthesis. Computers in Cardiology 36: 277-280, 2009.
[12] Kligfield P et al. Recommendations for the standardization and interpretation of the electrocardiogram, Part I: The electrocardiogram and its technology. Heart Rhythm, 3 (3): 394-412, March 2007.
[13] Field D Q, Zhou S H, Helfenbein E D, Gregg R E, and Lindauer J M. Technical challenges and future directions in lead reconstruction for reduced-lead systems. Journal of Electrocardiology, 41: 466-473, 2008.
[14] Goldberger A L et al. PhysioBank, PhysioToolkit, and PhysioNet: Components of a New Research Resource for Complex Physiologic Signals. Circulation, 101(23): e215-e220, June 2000.
[15] Pan J and Tompkins W J. A Real-Time QRS Detection Algorithm. IEEE Trans. Biomed. Eng., BME-32(3): 230-236, March 1985.
[16] Newlan S P, Kors J A, Meij S H, van Bemmel J H, and Simoons M L. Reconstruction of the 12-lead Electrocardiogram From Reduced Lead Sets. Journal of Electrocardiology, 37(1), 2004.
[17] Horček B M, Warren J W and Wang J J. On designing and testing transformations for derivation of standard 12-lead/18-lead electrocardiograms and vectorcardiograms from reduced lead sets of predictor leads. Journal of Electrocardiology, 41: 220-229, January 2008.
[18] Gregg R E, Zhou S H, Lindauer J M, Field D Q, and Helfenbein E D. Where do derived precordial leads fail? Journal of Electrocardiology, 41: 546-552, July 2008.
[19] Field D Q, Feldman C L, and Horček B M. Improved EASI Coefficients: Their Derivation, Values, and Performance. Journal of Electrocardiology, 35: suppl. 23-33, 2002.
[20] Parks T W and McClellan J H. Chebyshev Approximation for Nonrecursive Digital Filters with Linear Phase. IEEE Trans On Circuit Theory, 19(2): 189-194, March 1972.
[21] Saladin K. Anatomy & Physiology: the Unity of Form and Function. McGraw-Hill, New York, 2007.
[22] Malmivuo J and Plonsey R. Bioelectromagnetism—Principles and Applications of Bioelectric and Biomagnetic Fields. Oxford University Press, New York, 1995.
[23] Plonsey R and Barr R. Bioelectricity—A Quantitative Approach. Springer, New York, 2007.
[24] Gulrajani R M. The Forward and Inverse Problems of Electrocardiography. IEEE Eng in Medicine and Biology, 17: 84-101, 1998.
[25] Geselowitz D B. Dipole Theory in Electrocardiography. The American Journal of Cardiology, 14(3): 301-306, 1964.
[26] Frank E. An Accurate, Clinically Practical System for Spatial Vectorcardiography. Circulation, 13: 737-749, 1956.

The foregoing descriptions of the preferred embodiments are provided to enable any person skilled in the art to make or use the claimed subject matter. Various modifications to these embodiments will be readily apparent to those skilled in the art, and the generic principles defined herein may be applied to other embodiments without the use of the innovative faculty. Thus, the subject matter is not intended to be limited to the embodiments shown herein but is to be accorded the widest scope consistent with the principles and novel features disclosed herein.

I claim:
1. A body sensor system comprising:
 a. a number of sensors adapted to be disposed on the body of an individual and to receive signals concerning one or more physiological parameters of the individual, wherein the number of sensors includes a number of pairs of sensors;
b. a hub operably connected to the number of sensors and including a sensor module for receiving the signals from the number of sensors, wherein the sensor module includes a central processing unit configured to provide noise reduction in the signals obtained from the number of sensors, and wherein the central processing unit is configured to provide noise reduction using signals from the pairs of sensors according to the following equation: $Lead(t)=Lead(t_d+t)+Noise(t)$; and
c. a smart device operably connected to the hub to transmit a information from the number of sensors to a remote location.

2. A method for monitoring and recording physical parameter data on a subject, the method comprising the steps of:
a. providing body sensor system comprising:
  i. a number of sensors adapted to be disposed on a body of an individual to detect and receive signals concerning one or more physiological parameter of the individual, wherein number of sensors comprises a number of pairs of sensors, and the step of providing noise reduction comprises providing noise reduction to signals from the pairs of sensors according to the following equation: $Lead(t)=Lead(t_d+t)+Noise(t)$;
  ii. a hub operably connected to the number of sensors and including a sensor module operably connected to the number of sensors and configured to receive the signals from the number of sensors; and
  iii. a smart device operably connected to the hub to transmit the information from the number of sensors to a remote location;
b. attaching the number of the body of to an individual;
c. detecting signals from the body through the number of sensors system; and
d. analyzing the signals, wherein the step of analyzing signals comprises providing noise reduction to the signals from the number of sensors.

* * * * *